United States Patent [19]

Weier et al.

[11] Patent Number: 5,359,073
[45] Date of Patent: Oct. 25, 1994

[54] SUBSTITUTED-PHENYL (N,N'-CYCLOALKYL/ALKYL CARBOXAMIDE)-1H/3H-IMIDAZO[4,5-B]PYRIDINE COMPOUNDS AS PAF ANTAGONISTS

[75] Inventors: Richard M. Weier, Lake Bluff; Ish K. Khanna, Vernon Hills; Michael A. Stealey, Libertyville; Janet A. Julien, Glenview; Kirk T. Lentz, Niles, all of Ill.

[73] Assignee: G. D. Searle & Co., Chicago, Ill.

[21] Appl. No.: 981,957

[22] Filed: Nov. 24, 1992

[51] Int. Cl.$^5$ .................. C07D 471/04; C07D 471/06
[52] U.S. Cl. ...................... 546/118; 546/14; 544/350
[58] Field of Search ............... 546/118, 14; 514/303, 514/249; 544/350

[56] References Cited

U.S. PATENT DOCUMENTS

| | | | |
|---|---|---|---|
| 4,243,671 | 1/1981 | Harris et al. | 424/273 |
| 4,284,641 | 8/1981 | Thorogood | 424/273 |
| 4,357,340 | 11/1982 | Thorogood | 424/273 |
| 4,416,895 | 11/1983 | Thorogood | 424/273 |
| 4,579,862 | 4/1986 | Manley et al. | 514/399 |
| 4,804,658 | 2/1989 | Manley et al. | 514/234.2 |
| 4,914,108 | 4/1990 | Khanna et al. | 514/303 |

FOREIGN PATENT DOCUMENTS

| | | | |
|---|---|---|---|
| 0142333 | 5/1985 | European Pat. Off. | C07C 93/04 |
| 0142801 | 5/1985 | European Pat. Off. | C07C 143/78 |
| 0400974 | 12/1990 | European Pat. Off. | |
| 0461040 | 12/1991 | European Pat. Off. | |
| 89/08653 | 9/1989 | PCT Int'l Appl. | |
| 90/09997 | 9/1990 | PCT Int'l Appl. | |
| 92/18503 | 10/1992 | PCT Int'l Appl. | |
| 2025946 | 1/1980 | United Kingdom | C07D 233/56 |

OTHER PUBLICATIONS

Kazutoshi Miyake, "Synthesis and Structure . . . ", XIIth International Symposium on Medicinal Chemistry, Sep. 1992.
CA 115: 49685j, "Preparation of N-Benzylbenzimidazole . . . " by Wittaker et al, 1991.

*Primary Examiner*—C. Warren Ivy
*Assistant Examiner*—D. Margaret M. Mach
*Attorney, Agent, or Firm*—J. Timothy Keane

[57] ABSTRACT

A class of N,N'-cycloalkyl/alkyl benzamides of certain 1H-imidazo[4,5-b]pyridine and 3H-imidazo[4,5-b]pyridine compounds is described for treating cardiovascular and immuno-inflammatory related disorders mediated by platelet activating factor (PAF). Compounds of particular interest are those of the formula:

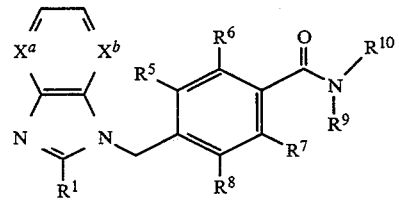

wherein each of $X^a$ and $X^b$ is independently selected from nitrogen atom and —CH—, with the proviso that when one of $X^a$ and $X^b$ is selected as nitrogen atom, then the other of $X^a$ and $X^b$ must be —CH—; wherein $R^1$ is selected from hydrido, alkyl, hydroxyalkyl, alkoxyalkyl, phenyl, halophenyl, alkylsilyloxyalkyl, amino, monoalkylamino, dialkylamino, aminoalkyl, monoalkylaminoalkyl and dialkylaminoalkyl; wherein each of $R^5$, $R^6$, $R^7$ and $R^8$ is independently selected from hydrido, hydroxy, alkyl, alkoxy, fluoro, chloro, bromo, haloalkyl, alkylthio, alkoxyalkyl, hydroxyalkyl, alkylthioalkyl, cyano, amino, monoalkylamino and dialkylamino; wherein each of $R^9$ and $R^{10}$ is independently selected from hydrido, alkyl, cycloalkyl, bicycloalkyl, heteroaryl, aryl, alkenyl and cycloalkenyl, and wherein any of said $R^9$ and $R^{10}$ substituents may be further substituted or a pharmaceutically-acceptable salt thereof.

36 Claims, No Drawings

SUBSTITUTED-PHENYL (N,N'-CYCLOALKYL/ALKYL CARBOXAMIDE)-1H/3H-IMIDAZO[4,5-B]PYRIDINE COMPOUNDS AS PAF ANTAGONISTS

FIELD OF THE INVENTION

This invention is in the field of therapeutics and relates to compounds for treatment of inflammatory and respiratory disorders, such as asthma, vascular disorders, such as cardiovascular and cerebrovascular lo diseases, and related diseases. Of particular interest is a class of novel N,N'-cycloalkyl/alkyl benzamides of certain 1H-imidazo[4,5-b]pyridine and 3H-imidazo[4,5-b]pyridine derivatives wherein the phenyl ring of the benzamide group is substituted with one or more moieties, and which class is useful for treatment of cardiovascular and immuno-inflammatory related disorders mediated by platelet activating factor (PAF).

BACKGROUND OF THE INVENTION

Platelet-activating factor (PAF) has been associated with various biological activities and pathways, thus making it an important mediator responsible for a variety of physiological processes, including activation of platelets, smooth muscle contraction, pathogenesis of immune complex deposition, inflammation, and respiratory, cardiovascular and intravascular alterations. These physiological processes are associated with a large group of diseases, such as cardiovascular disorders, asthma, lung edema, endotoxin shock, adult respiratory distress syndrome and inflammatory diseases.

Various classes of compounds are known for inhibiting platelet activation induced by agents such as arachidonic acid, collagen and platelet activating factor. For example, several classes of imidazole derivatives are known for use in treatment of various cardiovascular and immuno-response diseases related to platelet dysfunction or platelet hyperactivity. U.S. Pat. No. 2,025,946 to Iizuki et al mentions certain classes of imidazoles, namely, N-(ω-substituted alkylphenylalkyl)imidazoles, N-(ω-substituted alkylphenyl)imidazoles and N-(nucleus-substituted phenylakyl)imidazoles which are described as having inhibitory effect on thromboxane synthetase and to be useful for treatment of inflammation, thrombus and asthma. U.S. Pat. Nos. 4,284,641 and 4,416,895 to Thorogood describe certain cycloalkyl/cycloalkenyl imidazoles which inhibit platelet aggregation or reduce the adhesive character of platelets by selective inhibition of thromboxane A2. Also described for the same purpose in U.S. Pat. No. 4,537,340 to Thorogood is a class of 1-arylalkylimidazoles. In U.S. Pat. No. 4,243,671 to Harris et al, the compound 1-(3-phenyl-2-propenyl)1H-imidazole is described as effective in inhibiting thromboxane synthetase, arachidonic acid-induced platelet aggregation and bronchoconstriction.

Compounds are known for use in treating platelet dysfunction or platelet hyperactivity induced specifically by platelet activating factor (PAF). For example, a certain class of glycerol derivatives useful as PAF antagonists is described in EP No. 142,333. A class of indene derivatives is described in EP No. 142,801 as PAF inhibitors. Compounds containing heterocyclic moieties of various types are also known as PAF antagonists. For example, U.S. Pat. No. 4,579,862 to Manley et al describes certain imidazole/pyridinylalkanoic acid derivatives as PAF antagonists. U.S. Pat. No. 4,804,658 to Manley et al describes a class of imidazopyridine derivatives useful as PAF inhibitors and mentions, in particular, the compound N-cyclohexyl-N-methyl-4-(1H-imidazo [4,5-c]pyridin-1-yl-methyl)benzamide as an inhibitor of PAF-induced aggregation in an assay using human platelet-rich plasma. U.S. Pat. No. 4,914,108 to Khanna et al describes a class of 5-substituted(4,5-c) imidazopyridine compounds having PAF antagonist activity, including, in particular, the compound 5-[4{-(N-isopropyl,N-cyclohexyl)carboxamido}-2-methoxybenzyl]imidazo[4,5-c]pyridine.

DESCRIPTION OF THE INVENTION

Treatment of platelet-activiating-factor-related pathologies, such as PAF-stimulated pathologies or platelet-mediated airway hyper-reactivity, is accomplished by administering to a susceptible subject a therapeutically-effective amount of a compound of a class of compounds represented by Formula I:

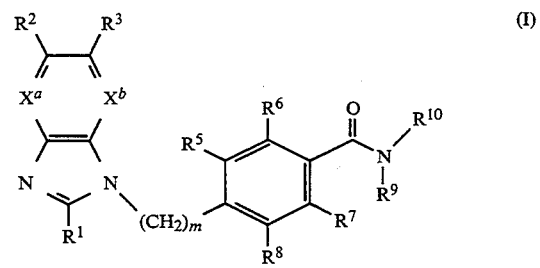

wherein each of $X^a$ and $X^b$ is independently selected from nitrogen atom and $>CR^4$, with the proviso that when one of $X^a$ and $X^b$ is selected as nitrogen atom then the other of $X^a$ and $X^b$ must be selected from $>CR^4$; wherein m is a number selected from one through six, inclusive;

wherein $R^1$ is selected from hydrido, alkyl, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyloxyalkyl, aryl/alkylsilyloxyalkyl, arylsilyloxyalkyl, mercaptoalkyl, alkoxycarbonyloxy, alkylthio, alkylthioalkyl, alkylsulfinylalkyl, alkylsulfonylalkyl, cycloalkylthio, cycloalkylalkylthio, alkylcarbonylthio, arylthio, arylcarbonylthio, aralkylthio and aralkylcarbonylthio;

wherein each of $R^2$, $R^3$ and $R^4$ is independently selected from hydrido, alkyl, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, alkoxyalkyl, alkylcarbonyl, alkylcarbonylalkyl, alkylsilyloxyalkyl, alkoxycarbonyl, cyano, nitro, alkylthio, alkylthioalkyl, alkylsulfinylalkyl, alkylsulfonylalkyl, cycloalkylthio and cycloalkylalkylthio;

wherein each of $R^5$, $R^6$, $R^7$ and $R^8$ is independently selected from hydrido, alkyl, hydroxy, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyoxyalkyl, alkoxycarbonyloxy, alkylthio, alkylthioalkyl, alkylsulfinylalkyl, alkylsulfonylalkyl, cycloalkylthio, cycloalkylalkylthio, alkylcarbonylthio, arylthio, arylcarbonylthio, aralkylthio and aralkylcarbonylthio, with the proviso that at least one of $R^5$, $R^6$, $R^7$ and $R^8$ must be a group other than hydrido;

wherein each of $R^1$, $R^2$, $R^3$, $R^4$, $R^5$, $R^6$, $R^7$ and $R^8$ may be further independently selected from amino and amido radicals of the formulae

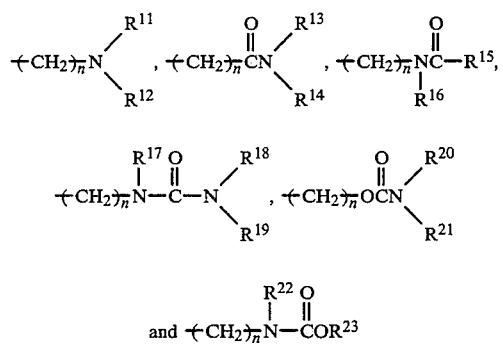

wherein each n is a number independently selected from zero to six, inclusive; wherein each of $R^{11}$ through $R^{23}$ is independently selected from hydrido, alkyl, cycloalkyl, hydroxyalkyl, cycloalkylalkyl, alkoxyalkyl, aralkyl and aryl;

wherein each of $R^9$ and $R^{10}$ is independently selected from hydrido, alkyl, haloalkyl, cycloalkyl, polycycloalkyl, polycycloalkylalkyl, cycloalkylalkyl, aralkyl, aryl, alkenyl, cycloalkenyl, heterocyclic and heterocyclicalkyl having one or more ring atoms selected from oxygen, sulfur and nitrogen atoms; wherein any of said $R^9$ and $R^{10}$ groups may be substituted at one or more substitutable positions by one or more groups selected from alkyl, halo, haloalkyl and alkoxy; or a pharmaceutically-acceptable salt thereof.

A preferred family of compounds consists of those compounds of Formula I as embraced by Formula IA and Formula IB:

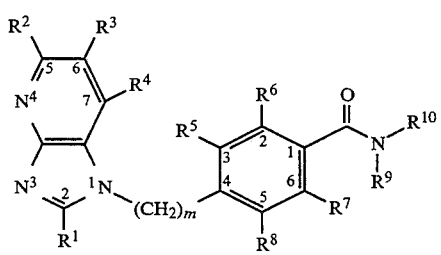

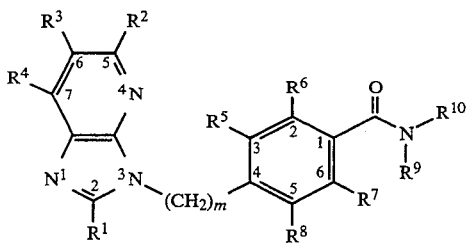

wherein m is a number selected from one through five, inclusive; wherein $R^1$ is selected from hydrido, alkyl, hydroxyalkyl, formyl, halo, haloalkyl, cycloalkyl, alkylcycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, cyano, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyloxyalkyl, aryl/alkylsilyloxyalkyl, arylsilyloxyalkyl, mercaptoalkyl, alkoxycarbonyloxy, alkylthio, alkylthioalkyl, alkylsulfinylalkyl, alkylsulfonylalkyl and arylthio;

wherein each of $R^2$, $R^3$ and $R^4$ is independently selected from hydrido, alkyl, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, alkoxyalkyl, alkylcarbonyl, alkylcarbonylalkyl, alkylsilyloxyalkyl, alkoxycarbonyl, cyano, nitro, alkylthio, alkylthioalkyl, alkylsulfinylalkyl and alkylsulfonylalkyl;

wherein each of $R^5$, $R^6$, $R^7$ and $R^8$ is independently selected from hydrido, alkyl, hydroxy, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyloxyalkyl, alkoxycarbonyloxy, alkylthio, alkylthioalkyl, alkylsulfinylalkyl, alkylsulfonylalkyl and arylthio, with the proviso that at least one of $R^5$, $R^6$, $R^7$ and $R^8$ must be a group other than hydrido;

wherein each of $R^1$, $R^2$, $R^3$, $R^4$, $R^5$, $R^6$, $R^7$ and $R^8$ may be further independently selected from amino and amido radicals of the formulae

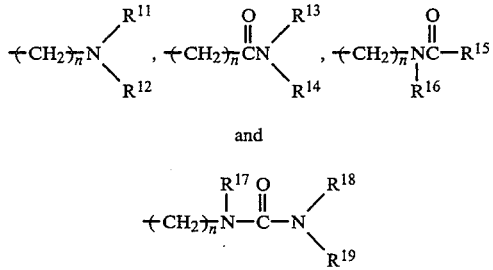

wherein each n is a number independently selected from zero to five, inclusive; wherein each of $R^{11}$ through $R^{19}$ is independently selected from hydrido, alkyl, cycloalkyl, hydroxyalkyl, cycloalkylalkyl, alkoxyalkyl, aralkyl and aryl;

wherein each of $R^9$ and $R^{10}$ is independently selected from hydrido, alkyl, haloalkyl, cycloalkyl, polycycloalkyl, polycycloalkylalkyl, cycloalkylalkyl, aralkyl, aryl, alkenyl, cycloalkenyl, heterocyclic and heterocyclicalkyl having one or more ring atoms selected from oxygen, sulfur and nitrogen atoms, wherein any of said $R^9$ and $R^{10}$ groups may be substituted at one or more substitutable positions by one or more groups selected from alkyl, halo, haloalkyl and alkoxy; or a pharmaceutically-acceptable salt thereof.

A more preferred family of compounds consists of those compounds of Formula I wherein m is a number selected from one through four, inclusive; wherein $R^1$ is selected from hydrido, alkyl, hydroxyalkyl, halo, haloalkyl, cycloalkyl, alkylcycloalkyl, cycloalkylalkyl, cycloalkylhaloalkyl, alkoxy, aralkyl, aralkylhaloalkyl, aryl, haloaryl, aryloxy, aryloxyalkyl, alkoxyalkyl, alkylcarbonylalkyl, cyano, carboxyalkyl, alkylcarbonyloxyalkyl, alkoxycarbonylalkyl, aralkoxycarbonylalkyl, aralkylcarbonyloxyalkyl, alkylsilyloxyalkyl, aryl/alkylsilyloxyalkyl, arylsilyloxyalkyl, mercaptoalkyl, alkylthio, alkylthioalkyl, alkylsulfinylalkyl, alkylsulfonylalkyl and arylthio;

wherein each of $R^2$, $R^3$ and $R^4$ is independently selected from hydrido, alkyl, hydroxyalkyl, halo, haloalkyl, cycloalkyl, alkylcycloalkyl, cycloalkylalkyl, cycloalkylhaloalkyl, alkoxy, aralkyl, aralkylhaloalkyl, alkoxyalkyl, alkylcarbonylalkyl, alkylsilyloxyalkyl, cyano, nitro, alkylthio, alkylthioalkyl, alkylsulfinylalkyl and alkylsulfonylalkyl;

wherein each of $R^5$, $R^6$, $R^7$ and $R^8$ is independently selected from hydrido, alkyl, hydroxy, hydroxyalkyl, halo, haloalkyl, cycloalkyl, alkylcycloalkyl, cycloalkylalkyl, alkoxy, aralkyl, aryl, haloaryl, aryloxy, aryloxyalkyl, aralkoxy, alkoxyalkyl, cyano, nitro, carboxyl, carboxyalkyl, alkylcarbonyloxy, alkylsilyloxyalkyl, alkoxycarbonyloxy, alkylthio, alkylthioalkyl, alkylsulfinylalkyl, alkylsulfonylalkyl and arylthio, with the proviso that at least one of $R^5$, $R^6$, $R^7$ and $R^8$ must be a group other than hydrido;

wherein each of $R^1$, $R^2$, $R^3$, $R^4$, $R^5$, $R^6$, $R^7$ and $R^8$ may be further independently selected from amino and amido radicals of the formulae

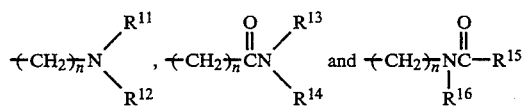

wherein each n is a number independently selected from zero to four, inclusive; wherein each of $R^{11}$ through $R^{16}$ is independently selected from hydrido, alkyl, cycloalkyl, hydroxyalkyl, cycloalkylalkyl, alkoxyalkyl, aralkyl and aryl;

wherein each of $R^9$ and $R^{10}$ is independently selected from hydrido, alkyl, haloalkyl, cycloalkyl, polycycloalkyl, polycycloalkylalkyl, cycloalkylalkyl, aralkyl, aryl, alkenyl, cycloalkenyl, heterocyclic and heterocyclicalkyl having one or more ring atoms selected from oxygen, sulfur and nitrogen atoms, wherein any of said $R^9$ and $R^{10}$ groups may be substituted at one or more substitutable positions by one or more groups selected from alkyl, halo, haloalkyl and alkoxy, with the proviso that when $R^9$ or $R^{10}$ is an alkenyl or a cycloalkenyl group, then the double bond of such group cannot be adjacent to the nitrogen atom of the amido group of Formula I; or a pharmaceutically-acceptable salt thereof.

An even more preferred family of compounds consists of those compounds of Formula I wherein m is a number selected from one through three, inclusive; wherein $R^1$ is selected from hydrido, alkyl, hydroxyalkyl, halo, haloalkyl, cycloalkyl, alkylcycloalkyl, cycloalkylalkyl, cycloalkylhaloalkyl, alkoxy, phenylalkyl, phenyl, halophenyl, phenoxy, phenoxyalkyl, alkoxyalkyl, cyano, alkylsilyloxyalkyl, phenyl/alkylsilyloxyalkyl, phenylsilyloxyalkyl, alkylthio and phenylthio;

wherein each of $R^2$, $R^3$ and $R^4$ is independently selected from hydrido, alkyl, hydroxyalkyl, halo, haloalkyl, cycloalkyl, alkylcycloalkyl, cycloalkylalkyl, alkoxy, phenylalkyl, alkoxyalkyl, alkylcarbonylalkyl, alkylsilyloxyalkyl, cyano, nitro and alkylthio;

wherein each of $R^5$, $R^6$, $R^7$ and $R^8$ is independently selected from hydrido, alkyl, hydroxy, hydroxyalkyl, halo, haloalkyl, cycloalkyl, alkylcycloalkyl, cycloalkylalkyl, alkoxy, phenylalkyl, phenyl, halophenyl, phenyloxy, phenyloxyalkyl, alkoxyalkyl, cyano, nitro, carboxyalkyl, alkylsilyloxyalkyl, alkylthio and phenylthio, with the proviso that at least one of $R^5$, $R^6$, $R^7$ and $R^8$ must be a group other than hydrido;

wherein each of $R^1$, $R^2$, $R^3$, $R^4$, $R^5$, $R^6$, $R^7$ and $R^8$ may be further independently selected from amino and amido radicals of the formulae

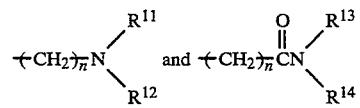

wherein each n is a number independently selected from zero to four, inclusive; wherein each of $R^{11}$ through $R^{14}$ is independently selected from hydrido, alkyl, cycloalkyl, hydroxyalkyl, cycloalkylalkyl, alkoxyalkyl, phenylalkyl and phenyl;

wherein each of $R^9$ and $R^{10}$ is independently selected from hydrido, alkyl, haloalkyl, cycloalkyl, bicycloalkyl, bicycloalkylalkyl, cycloalkylalkyl, phenylalkyl, phenyl, alkenyl, cycloalkenyl, heterocyclic and heterocyclicalkyl having one or more ring atoms selected from oxygen, sulfur and nitrogen atoms, wherein any of said $R^9$ and $R^{10}$ groups may be Substituted at one or more substitutable positions by one or more groups selected from alkyl, halo, haloalkyl and alkoxy, with the proviso that when $R^9$ or $R^{10}$ is an alkenyl or a cycloalkenyl group, then the double bond of such group cannot be adjacent to the nitrogen atom of the amido group of Formula I; or a pharmaceutically-acceptable salt thereof.

A highly preferred family of compound consists of compounds of Formula I wherein m is one or two; wherein $R^1$ is selected from hydrido, alkyl, hydroxyalkyl, halo, haloalkyl, cycloalkyl, alkylcycloalkyl, cycloalkylalkyl, cycloalkylhaloalkyl, alkoxy, benzyl, phenyl, halophenyl, alkoxyalkyl, alkylsilyloxyalkyl, phenyl/alkylsilyloxyalkyl, phenylsilyloxyalkyl and alkylthio;

wherein each of $R^2$, $R^3$ and $R^4$ is independently selected from hydrido, alkyl, hydroxyalkyl, halo, haloalkyl, cycloalkyl, alkylcycloalkyl, cycloalkylalkyl, alkoxy, benzyl, alkoxyalkyl, alkylsilyloxyalkyl and alkylthio;

wherein each of $R^5$, $R^6$, $R^7$ and $R^8$ is independently selected from hydrido, alkyl, hydroxy, hydroxyalkyl, formyl, halo, haloalkyl, cycloalkyl, alkylcycloalkyl, cycloalkylalkyl, alkoxy, alkoxyalkyl, alkylsilyloxyalkyl and alkylthio, with the proviso that at least one of $R^5$, $R^6$, $R^7$ and $R^8$ must be a group other than hydrido;

wherein each of $R^1$, $R^2$, $R^3$, $R^4$, $R^5$, $R^6$, $R^7$ and $R^8$ may be further independently selected from amino radicals of the formula

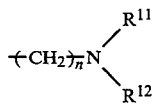

wherein each n is a number independently selected from zero to four, inclusive; wherein each of $R^{11}$ and $R^{12}$ is independently selected from hydrido, alkyl, cycloalkyl, hydroxyalkyl, cycloalkylalkyl, alkoxyalkyl, benzyl and phenyl;

wherein each of $R^9$ and $R^{10}$ is independently selected from hydrido, alkyl, haloalkyl, cycloalkyl, bicycloalkyl, bicycloalkylalkyl, cycloalkylalkyl, phenylalkyl, phenyl, alkenyl, cycloalkenyl, heterocyclic and heterocyclicalkyl having one or more ring atoms selected from oxygen, sulfur and nitrogen atoms, wherein any of said $R^9$ and $R^{10}$ groups may be substituted at one or more substitutable positions by one or more groups selected from alkyl, halo, haloalkyl and alkoxy, with the proviso that when $R^9$ or $R^{10}$ is an alkenyl or a cycloalkenyl group, then the double bond of such group cannot be adjacent to the nitrogen atom of the amido group of Formula I; or a pharmaceutically-acceptable salt thereof.

A more highly preferred family of compounds consists of those compounds of Formula I wherein m is one; wherein $R^1$ is selected from hydrido, alkyl, hydroxyalkyl, alkoxyalkyl, phenyl, halophenyl, alkylsilyloxyalkyl, amino, monoalkylamino, dialkylamino, aminoalkyl, monoalkylaminoalkyl and dialkylaminoalkyl, wherein when $R^1$ is alkyl or is a group containing alkyl, then such alkyl has one to about six carbon atoms and may have a linear or branched configuration;

wherein each of $R^2$, $R^3$ and $R^4$ is hydrido;

wherein each of $R^5$, $R^6$, $R^7$ and $R^8$ is independently selected from hydrido, hydroxy, alkyl, alkoxy, fluoro, chloro, bromo, haloalkyl, alkylthio, alkoxyalkyl, hydroxyalkyl, alkylthioalkyl, cyano, amino, monoalkylamino, dialkylamino, aminoalkyl, monoalkylaminoalkyl and dialkylaminoalkyl, with the proviso that at least one of $R^5$, $R^6$, $R^7$ and $R^8$ must be a group other than hydrido; wherein when any of the foregoing $R^5$, $R^6$, $R^7$ and $R^8$ is alkyl or is a group containing alkyl, such alkyl has one to about six carbon atoms and may have a linear or branched configuration;

wherein each of $R^9$ and $R^{10}$ is independently selected from hydrido, linear or branched chain alkyl having 1 to about 15 carbon atoms, cycloalkyl having 3 to about 8 carbon atoms, bicycloalkyl having 3 to about 8 carbon atoms in each ring, saturated or partially saturated heterocyclicalkyl having 4 to 8 ring atoms, heteroaryl having 5 or 6 ring atoms, phenyl, linear or branched alkenyl having 3 to about 15 carbon atoms with the proviso that the double bond of the alkenyl group cannot be adjacent to the nitrogen, cycloalkenyl having 5 to about 8 carbon atoms with the proviso that the double bond cannot be adjacent to the nitrogen of the amido group of Formula I, and wherein any of said $R^9$ and $R^{10}$ substituents may be further substituted with one or more groups selected from linear or branched lower alkyl, loweralkoxy, chloro and bromo; or a pharmaceutically-acceptable salt thereof.

An even more highly preferred family of compounds consists of those compounds of Formula I wherein m is one; wherein $R^1$ is selected from hydrido, methyl, ethyl, n-propyl, isopropyl, n-butyl, isobutyl, sec-butyl, tert-butyl, n-pentyl, isopentyl, neopentyl, hexyl, hydroxymethyl, hydroxyethyl, hydroxypropyl, hydroxybutyl, methoxymethyl, ethoxymethyl, propoxymethyl, butoxymethyl, methoxyethyl, methoxypropyl, methoxybutyl, ethoxyethyl, ethoxypropyl, ethoxybutyl, propoxymethyl, propoxyethyl, propoxypropyl, propoxybutyl, butoxymethyl, butoxyethyl, butoxypropyl, butoxybutyl, phenyl, monofluorophenyl, difluorophenyl, monochlorophenyl, dichlorophenyl, monobromophenyl, dibromophenyl, trimethylsilyloxymethyl, trimethylsilyloxyethyl, trimethylsilyloxypropyl, trimethylsilyloxybutyl, triethylsilyloxymethyl, triethylsilyloxyethyl, triethylsilyloxypropyl, triethylsilyloxybutyl, tripropylsilyloxymethyl, tripropylsilyloxyethyl, tripropylsilyloxypropyl, tripropylsilyloxybutyl, tert-butyl (dimethyl) silyloxymethyl, tert-butyl (dimethyl) silyloxyethyl, tert-butyl (dimethyl) silyloxypropyl, tert-butyl (dimethyl) silyloxybutyl, amino, N-methylamino, N,N'-dimethylamino, N-ethylamino, N,N'-diethylamino, N-propylamino, N,N'-dipropylamino, N-butylamino, N-N'-dibutylamino, N-methylaminomethyl, N-methylaminoethyl, N-methylaminopropyl, N-methylaminobutyl, N,N'-dimethylaminomethyl, N,N'-dimethylaminoethyl, N,N'-dimethylaminopropyl, N,N'-dimethylaminobutyl, N,N'-diethylaminomethyl, N,N'-diethylaminoethyl, N,N'-diethylaminopropyl, N,N'-diethylaminobutyl, N,N'-dipropylaminomethyl, N,N'-dipropylaminoethyl, N,N'-dipropylaminopropyl, N,N'-dipropylaminobutyl, N,N'-dibutylaminomethyl, N,N'-dibutylaminoethyl, N,N'-dibutylaminopropyl and N,N'-dibutylaminobutyl, wherein when $R^1$ is alkyl group or is one of the foregoing groups containing an alkyl group, such alkyl group may be linear or branched in configuration;

wherein each of $R^2$, $R^3$ and $R^4$ is hydrido;

wherein each of $R^5$, $R^6$, $R^7$ and $R^8$ is independently selected from hydrido, methyl, ethyl, n-propyl, isopropyl, n-butyl, isobutyl, sec-butyl, tert-butyl, n-pentyl, isopentyl, neopentyl, hexyl, fluoro, chloro, bromo, hydroxy, methoxy, ethoxy, propoxy, butoxy, pentoxy, trifluoromethyl, perfluoroethyl, dichloromethyl, methylthio, ethylthio, propylthio, butylthio, pentylthio, hydroxymethyl, hydroxyethyl, hydroxypropyl, hydroxybutyl, methoxymethyl, ethoxymethyl, propoxymethyl, butoxymethyl, methoxyethyl, methoxypropyl, methoxybutyl, ethoxyethyl, ethoxypropyl, ethoxybutyl, propoxymethyl, propoxyethyl, propoxypropyl, propoxybutyl, butoxymethyl, butoxyethyl, butoxypropyl, butoxybutyl, methylthiomethyl, methylthioethyl, methylthiopropyl, methylthiobutyl, ethylthiomethyl, ethylthioethyl, ethylthiopropyl, ethylthiobutyl, propylthiomethyl, propylthioethyl, propylthiopropyl, propylthiobutyl, butylthiomethyl, butylthioethyl, butylthiopropyl, butylthiobutyl, cyano, amino, N-methylamino, N,N'-dimethylamino, N-ethylamino, N,N'-diethylamino, N-propylamino, N,N'-dipropylamino, N-butylamino, N-N'-dibutylamino, N-methylaminomethyl, N-methylaminoethyl, N-methylaminopropyl, N-methylaminobutyl, N,N'-dimethylaminomethyl, N,N'-dimethylaminoethyl, N,N'-dimethylaminopropyl, N,N'-dimethylaminobutyl, N,N'-diethylaminomethyl, N,N'-diethylaminoethyl, N,N'-diethylaminopropyl, N,N'-diethylaminobutyl, N,N,-dipropylaminomethyl, N,N'-dipropylaminoethyl, N,N'-dipropylaminopropyl, N,N'-dipropylaminobutyl, N,N'-dibutylaminomethyl, N,N'-dibutylaminoethyl, N,N'-dibutylaminopropyl and N,N'-dibutylaminobutyl, with the proviso that at least one of $R^5$, $R^6$, $R^7$ and $R^8$ must be a group other than hydrido; wherein when any of $R^5$, $R^6$, $R^7$ and $R^8$ is alkyl or is a group containing alkyl, such alkyl group may be linear or branched in configuration;

wherein each of $R^9$ and $R^{10}$ is independently selected from hydrido, methyl, ethyl, n-propyl, isopropyl, isobutyl, sec-butyl, tert-butyl, n-pentyl, isopentyl, neopentyl, n-hexyl, n-heptyl, n-octyl, n-nonyl, n-decyl, 1,1,3,3-tetramethylbutyl, 2,2-dimethylethyl, 1,1-diethylmethyl, cyclopropyl, cyclobutyl, cyclohexyl, cycloheptyl, cyclooctyl, methylcyclopentyl, ethylcyclopentyl, 2-methylcyclohexyl, 3-methylcyclohexyl, 4-methylcyclohexyl, 3,5-dimethylcyclohexyl, ethylcyclohexyl, 3,5-diethylcyclohexyl, decalin, norbornyl, 2,2,1-bicycloheptyl, 2,2,1-bicycloheptylmethyl, phenyl, furanyl, pyranyl, oxetanyl, pyrrolidinyl, piperidinyl, tetrahydrothiophenyl, thiopyranyl, morpholino, piperazinyl, furanylmethyl, pyranylmethyl, oxetanylmethyl, pyrrolidinylmethyl, piperidinylmethyl, tetrahydrothiophenylmethyl, thiopyranylmethyl, morpholinomethyl, piperazinylmethyl, pyrrole, pyrrolemethyl, pyrazole, pyrazolemethyl, imidazole, imidazolemethyl, triazole, triazolemethyl, tetrazole, tetrazolemethyl, pyrazinyl, pyrazinylmethyl, thiazole, thiazolemethyl, oxazole, oxazolemethyl, pyridinyl and pyridinylmethyl; or a pharmaceutically-acceptable salt thereof.

The term "hydrido" denotes a single hydrogen atom (H). This hydrido group may be attached, for example, to an oxygen atom to form a hydroxyl group; or, as another example, one hydrido group may be attached to a carbon atom to form a >CH—group; or, as another example, two hydrido groups may be attached to a carbon atom to form a —CH$_2$— group. Where the term "alkyl" is used, either alone or within other terms such as "haloalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. The term "cycloalkyl" embraces mono-carbocyclic saturated radicals having three to about ten ring carbon atoms, preferably three to about six carbon atoms, such as cyclopropyl, cyclobutyl, cyclopentyl and cyclohexyl. The term "cycloalkylalkyl" denotes a cycloalkyl radical attached to an alkyl radical which is attachable to a substitutable position of Formula I. Examples of "cycloalkylalkyl" radicals are cyclopentylmethyl and cyclohexylethyl. The term "polycycloalkyl" denotes a ring system radical formed by two, or by three, or by more, cycloalkyl radicals joined together through one common carbon atom, or through two common adjacent carbon atoms to form a two-ring fused ring system, or formed by an alkylene bridge across a cycloalkyl ring. Such polycycloalkyl ring systems may contain from four to about twenty carbon atoms, and more preferably from eight to about ten carbon atoms. An example of a "polycycloalkyl" radical is adamantyl, also known as tricyclodecyl radical. The term "polycycloalkylalkyl" denotes a polycycloalkyl radical attached to an alkyl radical which is attachable to a substitutable position of Formula I. Examples of "polycycloalkylalkyl" radicals are adamantylmethyl and adamantylethyl. Included within the term "polycycloalkyl" is the term "bicycloalkyl" which denotes a fused ring system having two fused cycloalkyl rings collectively composed of seven to about twelve carbon atoms. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group, such as monofluoromethyl. Dihaloalkyl and polyhaloalkyl groups may be substituted with two or more of the same halo groups, or may have a combination of different halo groups. A dihaloalkyl group, for example, may have two fluoro atoms, such as difluoromethyl and difluorobutyl groups, or two chloro atoms, such as a dichloromethyl group, or one fluoro atom and one chloro atom, such as a fluorochloromethyl group. Examples of a polyhaloalkyl are trifluoromethyl, 1,1-difluoroethyl, 2,2,2-trifluoroethyl, perfluoroethyl, 2,2,3,3-tetrafluoropropyl and perfluoropropyl groups. The term "difluoroalkyl" embraces alkyl groups having two fluoro atoms substituted on any one or two of the alkyl group carbon atoms. The terms "alkylol" and "hydroxyalkyl" embrace linear or branched alkyl groups having one to about ten carbon atoms any one of which may be substituted with one or more hydroxyl groups. The term "alkylsilyloxyalkyl" embraces a silyloxyalkylene group wherein such group is attached to the nucleus of Formula I through its alkylene moiety and which group has three terminal alkyl moieties attached to the silyl portion of such group. Similarly, the term "aryl/alkylsilyloxyalkyl" embraces a silyloxyalkylene group wherein such group is attached to the nucleus of Formula I through its alkylene moiety and which group has three terminal moieties selected from alkyl and aryl, which three moieties are attached to the silyl portion of such group. Similarly, the term "arylsilyloxyalkyl" embraces a silyloxyalkylene group wherein such group is attached to the nucleus of Formula I through its alkylene moiety and which group has three terminal aryl moieties attached to the silyl portion of such group. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety, relative to groups substituted on the double-bonded carbons. The term "alkynyl" embraces linear or branched radicals having two to about twenty carbon atoms, preferably two to about ten carbon atoms, and containing at least one Carbon-carbon triple bond. The term "cycloalkenyl" embraces cyclic radicals having three to about ten ring carbon atoms including one or more double bonds involving adjacent ring carbons. The terms "alkoxy" and "alkoxyalkyl" embrace linear or branched oxy-containing radicals each having alkyl portions of one to about ten carbon atoms. An example of alkoxy is methoxy group. The term "alkoxyalkyl" also embraces alkyl radicals having two or more alkoxy groups attached to an alkyl radical. The term "dialkoxyalkyl" is exemplified by dimethoxymethyl and 2,2-diethoxyethyl. The "alkoxy" or "alkoxyalkyl" radicals may be further substituted with one or more halo atoms, such as fluoro, chloro or bromo, to provide haloalkoxy or haloalkoxyalkyl groups. The term "alkylthio" embraces radicals containing a linear or branched alkyl group, of one to about ten carbon atoms attached to a divalent sulfur atom, such as a methythio group. The terms "sulfinyl" and "sulfonyl" whether used alone or linked to other terms such as "alkyl", denote —SO— and —SO$_2$—, respectively. The term "aryl" denotes a carbocyclic aromatic ring system composed of one or more aromatic rings. Preferred aryl groups are those consisting of one, two, or three benzene rings. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "aryloxy" and "arylthio" denote, respectively, aryl groups having an oxygen or sulfur atom through which the radical is attached to a nucleus, examples of which are phenoxy and phenylthio. The term "aralkoxy", alone or within another term, embraces an aryl group attached to an alkoxy group to form, for example, benzyloxy. The term "acyl" whether used alone, or within terms such as acyloxy and acylaminoalkyl, denotes a radical provided by the residue after removal of hydroxyl from an organic acid, examples of such radical being acetyl and benzoyl. "Lower alkanoyl" is an example of a more prefered sub-class of acyl. The term "amido" denotes a radical consisting of nitrogen atom attached to a carbonyl group, which radical may be further substituted in the manner described herein. The amido radical can be attached to the nucleus of a compound of the invention through the carbonyl moiety or through the nitrogen atom of the amido radical. The term "alkenylalkyl" denotes a radical having a double-bond unsaturation site between two carbons, and which radical is further substituted with alkyl groups which may optionally contain additional double-bond unsaturation.

The terms "heterocyclic" and "heterocyclicalkyl" embrace ring systems of four to ten ring members with at least one ring member being a hetero atom selected from oxygen, sulfur and nitrogen atom, wherein said ring system may be monocyclic or bicyclic and may be fully saturated or partially saturated or fully unsaturated, and may be fused to a benzene or cyclohexane ring, wherein the point of attachment of the ring system to the backbone of the structure of Formula I may be through a bond to any substitutable position on said heterocyclic ring system or through an alkyl group interposed between the ring system and the point of attachment to Formula I, and wherein any substitutable position of the ring system may be optionally substituted with one or more radicals selected from alkyl, alkoxy, alkenyl, alkynyl, halo, trifluoromethyl, oxo, cyano and phenyl, and wherein the said heterocyclic ring nitrogen atom may be combined with oxygen to form an N-oxide. Within the term "heterocyclic" ring system are the subset terms "heteroaryl" and "heteroarylalkyl". The term "heteroaryl" embraces aromatic ring systems containing one or two hetero atoms selected from oxygen, nitrogen and sulfur in a ring system having five or six ring members, examples of which are thienyl, furanyl, imidazolyl, pyrazolyl, triazolyl, tetrazolyl, pyridinyl, thiazolyl, pyrimidyl and isoxazolyl. Such heteroaryl may be attached as a substituent through a carbon atom of the heteroaryl ring system, or may be attached through a carbon atom of a moiety substituted on a heteroaryl ring-member carbon atom, for example, through the methylene substituent of imidazolemethyl moiety.

For any of the foregoing defined radicals, preferred radicals are those containing from one to about twelve carbon atoms.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl, neopentyl and hexyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Included within the family of compounds of Formula I are the tautomeric forms of the described compounds, as well as the stereoisomers including diastereoisomers and enantiomers, and pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxy, butyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

Compounds of Formula I or their physiologically-acceptable or pharmaceutically-acceptable salts have a potential PAF-antagonistic activity and are of potential value therapeutically as active components in pharmaceutical compositions. Platelet activating factor (PAF) is the phospholipid "1-0-alkyl-2-acetyl-sn-glycero-3-phosphocholine" (AGEPC) which is known as a potent lipid mediator released by animal and human proinflammatory cells. These cells include primarily basophilic and neutrophilic granulocytes, endothelial cells, fibroblasts, epithelial brain cells, macrophages (from blood and tissue) and thrombocytes which are involved in inflammatory reactions.

In pharmacological trials, PAF may cause bronchoconstriction, a lowering of blood pressure, the triggering of thrombocyte aggregation and a proinflammatory activity. Thus PAF is indicated, directly or indirectly, as a mediator in anaphylaxis, in the pathophysiology of allergic conditions, bronchial asthma and in inflammations in general. Compounds of Formula I are therefore suitable for treating patients affected by diseases in which PAF is implicated, including inflammatory or allergic processes or autoimmune diseases. Examples of indications for a PAF antagonist include inflammatory processes of the tracheobronchial tree (acute and chronic bronchitis, bronchial asthma) or of the kidneys (glomerulonephritis), the joints (rheumatic complaints), anaphylactic conditions, allergies and inflammation in the mucous membranes (rhinitis, conjunctivitis) and the skin (e.g. psoriasis, atopic eczema, cold-induced urticaria) and shock caused by sepsis, endotoxins, trauma or burns.

Other important indications for a PAF antagonist include the following: lesions and inflammation in the gastric and intestinal linings, such as shock ulcers, ulcerative colitis, Crohn's disease, ischemic bowel necrosis, stress ulcers and peptic ulcers in general, but particularly ventricular and duodenal ulcers; obstructive lung diseases such as bronchial hyper-reactivity; inflammatory diseases of the pulmonary passages, such as chronic bronchitis; cardio/circulatory diseases such as polytrauma, anaphylaxis and arterioschlerosis; inflammatory intestinal diseases, EPH gestosis (edema-proteinuria hypertension); diseases of extracorporeal circulation, e.g. heart insufficiency, cardiac infarct, organ damage caused by high blood pressure, ischaemic diseases, inflammatory and immunological diseases; immune modulation in the transplanting of foreign tissues, e.g. the rejection of kidney, liver an other transplants; immune modulation in leukemia; propagation of metastasis, e.g. in bronchial neoplasia; diseases of the CNS, such as migraine, multiple schlerosis, endogenic depression and agarophobia (panic disorder). Compounds of Formula I could also be effective as follows: as cyto- and organoprotective agents, e.g. for neuroprotection; to treat DIC (disseminated intravascular coagulation); to treat side effects of drug therapy, e.g. anaphylactoid circulatory reactions; to treat incidents caused by contrast media and other side effects in tumor therapy; to diminish incompatibilities in blood transfusions; to prevent fulminant liver failure (CCl intoxication); to treat amanita phalloides intoxication (mushroom poisoning); to treat symptoms of parasitic diseases (e.g. worms); to treat autoimmune diseases (e.g. Werlhof's disease); to treat autoimmune hemolytic anemia, autoimmunologically induced glomerulonephritis, thyroids Hashimoto, primary myxoedema, pernicious anemia, autoimmune atrophic gastritis, Addison's disease, juvenile diabetes, Goodpasture syndrome, idiopathic leucopenia, primary biliary cirrhosis, active or chronically aggressive hepatitis (HBsAg-neg.), ulcerative colitis and systemic lupus erythematodes (SLE), ideopathic thrombocytopenic purpura (ITP); to treat diabetes, juvenile diabetes, diabetic retinopathy, polytraumatic shock, haemorrhagic shock; and to treat PAF-associated interaction with tissue hormones (autocoid hormones), lymphokines and other mediators.

Compounds of the invention may also be used in combinations for which PAF-antagonists are suitable, with $\beta$-adrenergics, parasympatholytics, corticosteroids, antiallergic agents and secretolytics. When compounds of Formula I are combined with TNF (tumor necrosis factor), the TNF is likely to be better tolerated (elimination of disturbing side effects). Thus, TNF may be used in higher dosages than when it is administered alone. The term "combination" here also includes the administration of the two active substances in separate preparations simultaneously or in sequence over a time period. When compounds are administered in combination with $\beta$-adrenergics, a synergistic effect may be achieved.

A family of specific compounds of particular interest within Formula IA consists of compounds, and their pharmaceutically-acceptable salts, of the following group:

4-(1H-imidazo[4,5-b]pyridin-1-ylmethyl)-3-methoxybenzoic acid, N-cyclobutyl-N-cyclohexyl amide;

4-(1H-imidazo[4,5-b]pyridin-1-ylmethyl)-3-methoxybenzoic acid, N-cyclopropyl-N-cyclohexyl amide;

4-(1H-imidazo[4,5-b]pyridin-1-ylmethyl)-3-ethoxybenzoic acid, N-cyclopentyl-N-cyclopentyl amide;

4-(1H-imidazo[4,5-b]pyridin-1-ylmethyl)-3-methoxybenzoic acid, N-isopropyl-N-cyclopentyl amide;

4-(1H-imidazo[4,5-b]pyridin-1-ylmethyl)-3-methoxybenzoic acid, N-cyclohexyl-N-cyclohexyl amide;

4-(1H-imidazo[4,5-b]pyridin-1-ylmethyl)-3-methoxybenzoic acid, N-2-butyl-N-cyclohexyl amide;

4-(1H-imidazo[4,5-b]pyridin-1-ylmethyl)-3-methoxybenzoic acid, N-phenyl-N-cyclohexyl amide;

4-(1H-imidazo[4,5-b]pyridin-1-ylmethyl)-3-methoxybenzoic acid, N-3-pentyl-N-cyclohexyl amide;

4-(1H-imidazo[4,5-b]pyridin-1-ylmethyl)-3-methoxybenzoic acid, N-3-methylcyclohexyl-N-cyclopentyl amide;

4-(1H-imidazo[4,5-b]pyridin-1-ylmethyl)-3-methoxybenzoic acid, N-4-methylcyclohexyl-N-cyclopentyl amide;

4-(1H-imidazo[4,5-b]pyridin-1-ylmethyl)-3-methoxybenzoic acid, N-2-methylcyclohexyl-N-cyclopentyl amide;

4-(1H-imidazo[4,5-b]pyridin-1-ylmethyl)-3-methoxybenzoic acid, N-2-methylcyclohexyl-N-isopropyl amide;

4-(1H-imidazo[4,5-b]pyridin-1-ylmethyl)-3-methoxybenzoic acid, N-3-methylcyclohexyl-N-isopropyl amide;

4-(1H-imidazo[4,5-b]pyridin-1-ylmethyl)-3-methoxybenzoic acid, N-3,5-dimethylcyclohexyl-N-isopropyl amide;

4-(1H-imidazo[4,5-b]pyridin-1-ylmethyl)-2-methoxybenzoic acid, N-cyclobutyl-N-cyclohexyl amide;

4-(1H-imidazo[4,5-b]pyridin-1-ylmethyl)-2-methoxybenzoic acid, N-cyclopropyl-N-cyclohexyl amide;

4-(1H-imidazo[4,5-b]pyridin-1-ylmethyl)-2-methoxybenzoic acid, N-cyclopentyl-N-cyclopentyl amide;
4-(1H-imidazo[4,5-b]pyridin-1-ylmethyl)-2-methoxybenzoic acid, N-isopropyl-N-cyclopentyl amide;
4-(1H-imidazo[4,5-b]pyridin-1-ylmethyl)-2-methoxybenzoic acid, N-cyclohexyl-N-cyclohexyl amide;
4-(1H-imidazo[4,5-b]pyridin-1-ylmethyl)-2-methoxybenzoic acid, N-2-butyl-N-cyclohexyl amide;
4-(1H-imidazo[4,5-b]pyridin-1-ylmethyl)-2-methoxybenzoic acid, N-phenyl-N-cyclohexyl amide;
4-(1H-imidazo[4,5-b]pyridin-1-ylmethyl)-2-methoxybenzoic acid, N-3-pentyl-N-cyclohexyl amide;
4-(1H-imidazo[4,5-b]pyridin-1-ylmethyl)-2-methoxybenzoic acid, N-3-methylcyclohexyl-N-cyclopentyl amide;
4-(1H-imidazo[4,5-b]pyridin-1-ylmethyl)-2-methoxybenzoic acid, N-4-methylcyclohexyl-N-cyclopentyl amide;
4-(1H-imidazo[4,5-b]pyridin-1-ylmethyl)-2-methoxybenzoic acid, N-2-methylcyclohexyl-N-cyclopentyl amide;
4-(1H-imidazo[4,5-b]pyridin-1-ylmethyl)-2-methoxybenzoic acid, N-2-methylcyclohexyl-N-isopropyl amide;
4-(1H-imidazo[4,5-b]pyridin-1-ylmethyl)-2-methoxybenzoic acid, N-3-methylcyclohexyl-N-isopropyl amide;
4-(1H-imidazo[4,5-b]pyridin-1-ylmethyl)-2-methoxybenzoic acid, N-3,5-dimethylcyclohexyl-N-isopropyl amide;
4-[(2-methyl-1H-imidazo[4,5-b]pyridin-1-yl)methyl]-3-methoxybenzoic acid, N-cyclobutyl-N-cyclohexyl amide;
4-[(2-methyl-1H-imidazo[4,5-b]pyridin-1-yl)methyl]-3-methoxybenzoic acid, N-cyclopropyl-N-cyclohexyl amide;
4-[(2-methyl-1H-imidazo[4,5-b]pyridin-1-yl)methyl]-3-methoxybenzoic acid, N-cyclopentyl-N-cyclopentyl amide;
4-[(2-methyl-1H-imidazo[4,5-b]pyridin-1-yl)methyl]-3-methoxybenzoic acid, N-isopropyl-N-cyclopentyl amide;
4-[(2-methyl-1H-imidazo[4,5-b]pyridin-1-yl)methyl]-3-methoxybenzoic acid, N-cyclohexyl-N-cyclohexyl amide;
4-[(2-methyl-1H-imidazo[4,5-b]pyridin-1-yl)methyl]-3-methoxybenzoic acid, N-2-butyl-N-cyclohexyl amide;
4-[(2-methyl-1H-imidazo[4,5-b]pyridin-1-yl)methyl]-3-methoxybenzoic acid, N-phenyl-N-cyclohexyl amide;
4-[(2-methyl-1H-imidazo[4,5-b]pyridin-1-yl)methyl]-3-methoxybenzoic acid, N-3-pentyl-N-cyclohexyl amide;
4-[(2-methyl-1H-imidazo[4,5-b]pyridin-1-yl)methyl]-3-methoxybenzoic acid, N-3-methylcyclohexyl-N-cyclopentyl amide;
4-[(2-methyl-1H-imidazo[4,5-b]pyridin-1-yl)methyl]-3-methoxybenzoic acid, N-4-methylcyclohexyl-N-cyclopentyl amide;
4-[(2-methyl-1H-imidazo[4,5-b]pyridin-1-yl)methyl]-3-methoxybenzoic acid, N-2-methylcyclohexyl-N-cyclopentyl amide;
4-[(2-methyl-1H-imidazo[4,5-b]pyridin-1-yl)methyl]-3-methoxybenzoic acid, N-2-methylcyclohexyl-N-isopropyl amide;
4-[(2-methyl-1H-imidazo[4,5-b]pyridin-1-yl)methyl]-3-methoxybenzoic acid, N-3-methylcyclohexyl-N-isopropyl amide;
4-[(2-methyl-1H-imidazo[4,5-b]pyridin-1-yl)methyl]-3-methoxybenzoic acid, N-3,5-dimethylcyclohexyl-N-isopropyl amide;
4-[(2-(hydroxymethyl)-1H-imidazo[4,5-b]pyridin-1-yl)methyl]-3-methoxybenzoic acid, N-cyclobutyl-N-cyclohexyl amide;
4-[(2-(hydroxymethyl)-1H-imidazo[4,5-b]pyridin-1-yl)methyl]-3-methoxybenzoic acid, N-cyclopropyl-N-cyclohexyl amide;
4-[(2-(hydroxymethyl)-1H-imidazo[4,5-b]pyridin-1-yl)methyl]-3-methoxybenzoic acid, N-cyclopentyl-N-cyclopentyl amide;
4-[(2-(hydroxymethyl)-1H-imidazo[4,5-b]pyridin-1-yl)methyl]-3-methoxybenzoic acid, N-isopropyl-N-cyclopentyl amide;
4-[(2-(hydroxymethyl)-1H-imidazo[4,5-b]pyridin-1-yl)methyl]-3-methoxybenzoic acid, N-cyclohexyl-N-cyclohexyl amide;
4-[(2-(hydroxymethyl)-1H-imidazo[4,5-b]pyridin-1-yl)methyl]-3-methoxybenzoic acid, N-2-butyl-N-cyclohexyl amide;
4-[(2-(hydroxymethyl)-1H-imidazo[4,5-b]pyridin-1-yl)methyl]-3-methoxybenzoic acid, N-phenyl-N-cyclohexyl amide;
4-[(2-(hydroxymethyl)-1H-imidazo[4,5-b]pyridin-1-yl)methyl]-3-methoxybenzoic acid, N-3-pentyl-N-cyclohexyl amide;
4-[(2-(hydroxymethyl)-1H-imidazo[4,5-b]pyridin-1-yl)methyl]-3-methoxybenzoic acid, N-3-methylcyclohexyl-N-cyclopentyl amide;
4-[(2-(hydroxymethyl)-1H-imidazo[4,5-b]pyridin-1-yl)methyl]-3-methoxybenzoic acid, N-4-methylcyclohexyl-N-cyclopentyl amide;
4-[(2-(hydroxymethyl)-1H-imidazo[4,5-b]pyridin-1-yl)methyl]-3-methoxybenzoic acid, N-2-methylcyclohexyl-N-cyclopentyl amide;
4-[(2-(hydroxymethyl)-1H-imidazo[4,5-b]pyridin-1-yl)methyl]-3-methoxybenzoic acid, N-2-methylcyclohexyl-N-isopropyl amide;
4-[(2-(hydroxymethyl)-1H-imidazo[4,5-b]pyridin-1-yl)methyl]-3-methoxybenzoic acid, N-3-methylcyclohexyl-N-isopropyl amide;
4-[(2-(hydroxymethyl)-1H-imidazo[4,5-b]pyridin-1-yl)methyl]-3-methoxybenzoic acid, N-3,5-dimethylcyclohexyl-N-isopropyl amide;
4-[(2-(methoxyoxymethyl)-1H-imidazo[4,5-b]pyridin-1-yl) methyl]-3-methoxybenzoic acid, N-cyclobutyl-N-cyclohexyl amide;
4-[(2-(methoxyoxymethyl)-1H-imidazo[4,5-b]pyridin-1-yl) methyl]-3-methoxybenzoic acid, N-cyclopropyl-N-cyclohexyl amide;
4-[(2-(methoxyoxymethyl)-1H-imidazo[4,5-b]pyridin-1-yl) methyl]-3-methoxybenzoic acid, N-cyclopentyl-N-cyclopentyl amide;
4-[(2-(methoxyoxymethyl)-1H-imidazo[4,5-b]pyridin-1-yl) methyl]-3-methoxybenzoic acid, N-isopropyl-N-cyclopentyl amide;
4-[(2-(methoxyoxymethyl)-1H-imidazo[4,5-b]pyridin-1-yl) methyl]-3-methoxybenzoic acid, N-cyclohexyl-N-cyclohexyl amide;
4-[(2-(methoxyoxymethyl)-1H-imidazo[4,5-b]pyridin-1-yl) methyl]-3-methoxybenzoic acid, N-2-butyl-N-cyclohexyl amide;

4-[(2-(methoxyoxymethyl)-1H-imidazo[4,5-b]pyridin-1-yl) methyl]-3-methoxybenzoic acid, N-phenyl-N-cyclohexyl amide;

4-[(2-(methoxyoxymethyl)-1H-imidazo[4,5-b]pyridin-1-yl) methyl]-3-methoxybenzoic acid, N-3-pentyl-N-cyclohexyl amide;

4-[(2-(methoxyoxymethyl)-1H-imidazo[4,5-b]pyridin-1-yl) methyl]-3-methoxybenzoic acid, N-3-methylcyclohexyl-N-cyclopentyl amide;

4-[(2-(methoxyoxymethyl)-1H-imidazo[4,5-b]pyridin-1-yl) methyl]-3-methoxybenzoic acid, N-4-methylcyclohexyl-N-cyclopentyl amide;

4-[(2-(methoxyoxymethyl)-1H-imidazo[4,5-b]pyridin-1-yl) methyl]-3-methoxybenzoic acid, N-2-methylcyclohexyl-N-cyclopentyl amide;

4-[(2-(methoxyoxymethyl)-1H-imidazo[4,5-b]pyridin-1-yl) methyl]-3-methoxybenzoic acid, N-2-methylcyclohexyl-N-isopropyl amide;

4-[(2-(methoxyoxymethyl)-1H-imidazo[4,5-b]pyridin-1-yl) methyl]-3-methoxybenzoic acid, N-3-methylcyclohexyl-N-isopropyl amide;

4-[(2-(methoxyoxymethyl)-1H-imidazo[4,5-b]pyridin-1-yl) methyl]-3-methoxybenzoic acid, N-3,5-dimethylcyclohexyl-N-isopropyl amide;

4-[(2-(dimethylaminomethyl)-1H-imidazo[4,5-b]pyridin-1-yl) methyl]-3-methoxybenzoic acid, N-cyclobutyl-N-cyclohexyl amide;

4-[(2-(dimethylaminomethyl)-1H-imidazo[4, 5-b]pyridin-1-yl) methyl]-3-methoxybenzoic acid, N-cyclopropyl-N-cyclohexyl amide;

4-[(2-(dimethylaminomethyl)-1H-imidazo[4,5-b]pyridin-1-yl) methyl]-3-methoxybenzoic acid, N-cyclopentyl-N-cyclopentyl amide;

4-[(2-(dimethylaminomethyl)-1H-imidazo[4,5-b]pyridin-1-yl) methyl]-3-methoxybenzoic acid, N-isopropyl-N-cyclopentyl amide;

4-[(2-(dimethylaminomethyl)-1H-imidazo[4,5-b]pyridin-1-yl) methyl]-3-methoxybenzoic acid, N-cyclohexyl-N-cyclohexyl amide;

4-[(2-(dimethylaminomethyl)-1H-imidazo[4,5-b]pyridin-1-yl) methyl]-3-methoxybenzoic acid, N-2-butyl-N-cyclohexyl amide;

4-[(2-(dimethylaminomethyl)-1H-imidazo[4,5-b]pyridin-1-yl) methyl]-3-methoxybenzoic acid, N-phenyl-N-cyclohexyl amide;

4-[(2-(dimethylaminomethyl)-1H-imidazo[4,5-b]pyridin-1-yl) methyl]-3-methoxybenzoic acid, N-3-pentyl-N-cyclohexyl amide;

4-[(2-(dimethylaminomethyl)-1H-imidazo[4,5-b]pyridin-1-yl) methyl]-3-methoxybenzoic acid, N-3-methylcyclohexyl-N-cyclopentyl amide;

4-[(2-(dimethylaminomethyl)-1H-imidazo[4,5-b]pyridin-1-yl) methyl]-3-methoxybenzoic acid, N-4-methylcyclohexyl-N-cyclopentyl amide;

4-[(2-(dimethylaminomethyl)-1H-imidazo[4,5-b]pyridin-1-yl) methyl]-3-methoxybenzoic acid, N-2-methylcyclohexyl-N-cyclopentyl amide;

4-[(2-(dimethylaminomethyl)-1H-imidazo[4,5-b]pyridin-1-yl) methyl]-3-methoxybenzoic acid, N-2-methylcyclohexyl-N-isopropyl amide;

4-[(2-(dimethylaminomethyl)-1H-imidazo[4,5-b]pyridin-1-yl) methyl]-3-methoxybenzoic acid, N-3-methylcyclohexyl-N-isopropyl amide;

4-[(2-(dimethylaminomethyl)-1H-imidazo[4,5-b]pyridin-1-yl) methyl]-3-methoxybenzoic acid, N-3,5-dimethylcyclohexyl-N-isopropyl amide;

4-[(2-(dimethylamino)-1H-imidazo[4,5-b]pyridin-1-yl) methyl]-3-methoxybenzoic acid, N-cyclobutyl-N-cyclohexyl amide;

4-[(2-(dimethylamino)-1H-imidazo[4,5-b]pyridin-1-yl) methyl]-3-methoxybenzoic acid, N-cyclopropyl-N-cyclohexyl amide;

4-[(2-(dimethylamino)-1H-imidazo[4,5-b]pyridin-1-yl) methyl]-3-methoxybenzoic acid, N-cyclopentyl-N-cyclopentyl amide;

4-[(2-(dimethylamino)-1H-imidazo[4,5-b]pyridin-1-yl) methyl]-3-methoxybenzoic acid, N-isopropyl-N-cyclopentyl amide;

4-[(2-(dimethylamino)-1H-imidazo[4,5-b]pyridin-1-yl) methyl]-3-methoxybenzoic acid, N-cyclohexyl-N-cyclohexyl amide;

4-[(2-(dimethylamino)-1H-imidazo[4,5-b]pyridin-1-yl) methyl]-3-methoxybenzoic acid, N-2-butyl-N-cyclohexyl amide;

4-[(2-(dimethylamino)-1H-imidazo[4,5-b]pyridin-1-yl) methyl]-3-methoxybenzoic acid, N-phenyl-N-cyclohexyl amide;

4-[(2-(dimethylamino)-1H-imidazo[4,5-b]pyridin-1-yl) methyl]-3-methoxybenzoic acid, N-3-pentyl-N-cyclohexyl amide;

4-[(2-(dimethylamino)-1H-imidazo[4,5-b]pyridin-1-yl) methyl]-3-methoxybenzoic acid, N-3-methylcyclohexyl-N-cyclopentyl amide;

4-[(2-(dimethylamino)-1H-imidazo[4,5-b]pyridin-1-yl) methyl]-3-methoxybenzoic acid, N-4-methylcyclohexyl-N-cyclopentyl amide;

4-[(2-(dimethylamino)-1H-imidazo[4,5-b]pyridin-1-yl) methyl]-3-methoxybenzoic acid, N-2-methylcyclohexyl-N-cyclopentyl amide;

4-[(2-(dimethylamino)-1H-imidazo[4,5-b]pyridin-1-yl) methyl]-3-methoxybenzoic acid, N-2-methylcyclohexyl-N-isopropyl amide;

4-[(2-(dimethylamino)-1H-imidazo[4,5-b]pyridin-1-yl) methyl]-3-methoxybenzoic acid, N-3-methylcyclohexyl-N-isopropyl amide;

4-[(2-(dimethylamino)-1H-imidazo[4,5-b]pyridin-1-yl) methyl]-3-methoxybenzoic acid, N-3,5-dimethylcyclohexyl-N-isopropyl amide;

4-[(2-(hydroxymethyl)-1H-imidazo[4, 5-b]pyridin-1-yl) methyl]-2-methoxybenzoic acid, N-cyclobutyl-N-cyclohexyl amide;

4-[(2-(hydroxymethyl)-1H-imidazo[4,5-b]pyridin-1-yl) methyl]-2-methoxybenzoic acid, N-cyclopropyl-N-cyclohexyl amide;

4-[(2-(hydroxymethyl)-1H-imidazo[4,5-b]pyridin-1-yl) methyl]-2-methoxybenzoic acid, N-cyclopentyl-N-cyclopentyl amide;

4-[(2-(hydroxymethyl)-1H-imidazo[4,5-b]pyridin-1-yl) methyl]-2-methoxybenzoic acid, N-isopropyl-N-cyclopentyl amide;

4-[(2-(hydroxymethyl)-1H-imidazo[4,5-b]pyridin-1-yl) methyl]-2-methoxybenzoic acid, N-cyclohexyl-N-cyclohexyl amide;

4-[(2-(hydroxymethyl)-1H-imidazo[4,5-b]pyridin-1-yl) methyl]-2-methoxybenzoic acid, N-2-butyl-N-cyclohexyl amide;

4-[(2-(hydroxymethyl)-1H-imidazo[4,5-b]pyridin-1-yl) methyl]-2-methoxybenzoic acid, N-phenyl-N-cyclohexyl amide;

4-[(2-(hydroxymethyl)-1H-imidazo[4,5-b]pyridin-1-yl) methyl]-2-methoxybenzoic acid, N-3-pentyl-N-cyclohexyl amide;

4-[(2-(hydroxymethyl)-1H-imidazo[4,5-b]pyridin-1-yl) methyl]-2-methoxybenzoic acid, N-3-methylcyclohexyl-N-cyclopentyl amide;

4-[(2-(hydroxymethyl)-1H-imidazo[4,5-b]pyridin-1-yl) methyl]-2-methoxybenzoic acid, N-4-methylcyclohexyl-N-cyclopentyl amide;

4-[(2-(hydroxymethyl)-1H-imidazo[4,5-b]pyridin-1-yl) methyl]-2-methoxybenzoic acid, N-2-methylcyclohexyl-N-cyclopentyl amide;

4-[(2-(hydroxymethyl)-1H-imidazo[4,5-b]pyridin-1-yl) methyl]-2-methoxybenzoic acid, N-2-methylcyclohexyl-N-isopropyl amide;

4-[(2-(hydroxymethyl)-1H-imidazo[4,5-b]pyridin-1-yl) methyl]-2-methoxybenzoic acid, N-3-methylcyclohexyl-N-isopropyl amide;

4-[(2-(hydroxymethyl)-1H-imidazo[4,5-b]pyridin-1-yl) methyl]-2-methoxybenzoic acid, N-3,5-dimethylcyclohexyl-N-isopropyl amide;

4-[(2-(methoxyoxymethyl)-1H-imidazo[4,5-b]pyridin-1-yl) methyl]-2-methoxybenzoic acid, N-cyclobutyl-N-cyclohexyl amide;

4-[(2-(methoxyoxymethyl)-1H-imidazo[4,5-b]pyridin-1-yl) methyl]-2-methoxybenzoic acid, N-cyclopropyl-N-cyclohexyl amide;

4-[(2-(methoxyoxymethyl)-1H-imidazo[4,5-b]pyridin-1-yl) methyl]-2-methoxybenzoic acid, N-cyclopentyl-N-cyclopentyl amide;

4-[(2-(methoxyoxymethyl)-1H-imidazo[4,5-b]pyridin-1-yl) methyl]-2-methoxybenzoic acid, N-isopropyl-N-cyclopentyl amide;

4-[(2-(methoxyoxymethyl)-1H-imidazo[4,5-b]pyridin-1-yl) methyl]-2-methoxybenzoic acid, N-cyclohexyl-N-cyclohexyl amide;

4-[(2-(methoxyoxymethyl)-1H-imidazo[4,5-b]pyridin-1-yl) methyl]-2-methoxybenzoic acid, N-2-butyl-N-cyclohexyl amide;

4-[(2-(methoxyoxymethyl)-1H-imidazo[4,5-b]pyridin-1-yl) methyl]-2-methoxybenzoic acid, N-phenyl-N-cyclohexyl amide;

4-[(2-(methoxyoxymethyl)-1H-imidazo[4,5-b]pyridin-1-yl) methyl]-2-methoxybenzoic acid, N-3-pentyl-N-cyclohexyl amide;

4-[(2-(methoxyoxymethyl)-1H-imidazo[4,5-b]pyridin-1-yl) methyl]-2-methoxybenzoic acid, N-3-methylcyclohexyl-N-cyclopentyl amide;

4-[(2-(methoxyoxymethyl)-1H-imidazo[4,5-b]pyridin-1-yl) methyl]-2-methoxybenzoic acid, N-4-methylcyclohexyl-N-cyclopentyl amide;

4-[(2-(methoxyoxymethyl)-1H-imidazo[4,5-b]pyridin-1-yl) methyl]-2-methoxybenzoic acid, N-2-methylcyclohexyl-N-cyclopentyl amide;

4-[(2-(methoxyoxymethyl)-1H-imidazo[4,5-b]pyridin-1-yl) methyl]-2-methoxybenzoic acid, N-2-methylcyclohexyl-N-isopropyl amide;

4-[(2-(methoxyoxymethyl)-1H-imidazo[4,5-b]pyridin-1-yl) methyl]-2-methoxybenzoic acid, N-3-methylcyclohexyl-N-isopropyl amide;

4-[(2-(methoxyoxymethyl)-1H-imidazo[4,5-b]pyridin-1-yl) methyl]-2-methoxybenzoic acid, N-3,5-dimethylcyclohexyl-N-isopropyl amide;

4-[(2-(dimethylaminomethyl)-1H-imidazo[4,5-b]pyridin-1-yl) methyl]-2-methoxybenzoic acid, N-cyclobutyl-N-cyclohexyl amide;

4-[(2-(dimethylaminomethyl)-1H-imidazo[4,5-b]pyridin-1-yl) methyl]-2-methoxybenzoic acid, N-cyclopropyl-N-cyclohexyl amide;

4-[(2-(dimethylaminomethyl)-1H-imidazo[4,5-b]pyridin-1-yl) methyl]-2-methoxybenzoic acid, N-cyclopentyl-N-cyclopentyl amide;

4-[(2-(dimethylaminomethyl)-1H-imidazo[4,5-b]pyridin-1-yl) methyl]-2-methoxybenzoic acid, N-isopropyl-N-cyclopentyl amide;

4-[(2-(dimethylaminomethyl)-1H-imidazo[4,5-b]pyridin-1-yl) methyl]-2-methoxybenzoic acid, N-cyclohexyl-N-cyclohexyl amide;

4-[(2-(dimethylaminomethyl)-1H-imidazo[4,5-b]pyridin-1-yl) methyl]-2-methoxybenzoic acid, N-2-butyl-N-cyclohexyl amide;

4-[(2-(dimethylaminomethyl)-1H-imidazo[4,5-b]pyridin-1-yl) methyl]-2-methoxybenzoic acid, N-phenyl-N-cyclohexyl amide;

4-[(2-(dimethylaminomethyl)-1H-imidazo[4,5-b]pyridin-1-yl) methyl]-2-methoxybenzoic acid, N-3-phenyl-N-cyclohexyl amide;

4-[(2-(dimethylaminomethyl)-1H-imidazo[4,5-b]pyridin-1-yl) methyl]-2-methoxybenzoic acid, N-3-methylcyclohexyl-N-cyclopentyl amide;

4-[(2-(dimethylaminomethyl)-1H-imidazo[4,5-b]pyridin-1-yl) methyl]-2-methoxybenzoic acid, N-4-methylcyclohexyl-N-cyclopentyl amide;

4-[(2-(dimethylaminomethyl)-1H-imidazo[4,5-b]pyridin-1-yl) methyl]-2-methoxybenzoic acid, N-2-methylcyclohexyl-N-cyclopentyl amide;

4-[(2-(dimethylaminomethyl)-1H-imidazo[4,5-b]pyridin-1-yl) methyl]-2-methoxybenzoic acid, N-2-methylcyclohexyl-N-isopropyl amide;

4-[(2-(dimethylaminomethyl)-1H-imidazo[4,5-b]pyridin-1-yl) methyl]-2-methoxybenzoic acid, N-3-methylcyclohexyl-N-isopropyl amide;

4-[(2-(dimethylaminomethyl)-1H-imidazo[4,5-b]pyridin-1-yl) methyl]-2-methoxybenzoic acid, N-3,5-dimethylcyclohexyl-N-isopropyl amide;

4-[(2-(dimethylamino)-1H-imidazo[4,5-b]pyridin-1-yl) methyl]-2-methoxybenzoic acid, N-cyclobutyl-N-cyclohexyl amide;

4-[(2-(dimethylamino)-1H-imidazo[4,5-b]pyridin-1-yl) methyl]-2-methoxybenzoic acid, N-cyclopropyl-N-cyclohexyl amide;

4-[(2-(dimethylamino)-1H-imidazo[4,5-b]pyridin-1-yl) methyl]-2-methoxybenzoic acid, N-cyclopentyl-N-cyclopentyl amide;

4-[(2-(dimethylamino)-1H-imidazo[4,5-b]pyridin-1-yl) methyl]-2-methoxybenzoic acid, N-isopropyl-N-cyclopentyl amide;

4-[(2-(dimethylamino)-1H-imidazo[4,5-b]pyridin-1-yl) methyl]-2-methoxybenzoic acid, N-cyclohexyl-N-cyclohexyl amide;

4-[(2-(dimethylamino)-1H-imidazo[4,5-b]pyridin-1-yl) methyl]-2-methoxybenzoic acid, N-2-butyl-N-cyclohexyl amide;

4-[(2-(dimethylamino)-1H-imidazo[4,5-b]pyridin-1-yl) methyl]-2-methoxybenzoic acid, N-phenyl-N-cyclohexyl amide;

4-[(2-(dimethylamino)-1H-imidazo[4,5-b]pyridin-1-yl) methyl]-2-methoxybenzoic acid, N-3-pentyl-N-cyclohexyl amide;

4-[(2-(dimethylamino)-1H-imidazo[4,5-b]pyridin-1-yl) methyl]-2-methoxybenzoic acid, N-3-methylcyclohexyl-N-cyclopentyl amide;

4-[(2-(dimethylamino)-1H-imidazo[4,5-b]pyridin-1-yl) methyl]-2-methoxybenzoic acid, N-4-methylcyclohexyl-N-cyclopentyl amide;

4-[(2-(dimethylamino)-1H-imidazo[4,5-b]pyridin-1-yl)methyl]-2-methoxybenzoic acid, N-2-methylcyclohexyl-N-cyclopentyl amide;

4-[(2-(dimethylamino)-1H-imidazo[4,5-b]pyridin-1-yl)methyl]-2-methoxybenzoic acid, N-2-methylcyclohexyl-N-isopropyl amide;

4-[(2-(dimethylamino)-1H-imidazo[4,5-b]pyridin-1-yl)methyl]-2-methoxybenzoic acid, N-3-methylcyclohexyl-N-isopropyl amide; and 4-[(2-(dimethylamino)-1H-imidazo[4,5-b]pyridin-1-yl)methyl]-2-methoxybenzoic acid, N-3,5-dimethylcyclohexyl-N-isopropyl amide.

A family of specific compounds of particular interest within Formula IB Consists of compounds, and their pharmaceutically-acceptable salts, of the following group:

4-(3H-imidazo[4,5-b]pyridin-1-ylmethyl)-3-methoxybenzoic acid, N-cyclobutyl-N-cyclohexyl amide;

4-(3H-imidazo[4,5-b]pyridin-1-ylmethyl)-3-methoxybenzoic acid, N-cyclopropyl-N-cyclohexyl amide;

4-(3H-imidazo[4,5-b]pyridin-1-ylmethyl)-3-ethoxybenzoic acid, N-cyclopentyl-N-cyclopentyl amide;

4-(3H-imidazo[4,5-b]pyridin-1-ylmethyl)-3-methoxybenzoic acid, N-isopropyl-N-cyclopentyl amide;

4-(3H-imidazo[4,5-b]pyridin-1-ylmethyl)-3-methoxybenzoic acid, N-cyclohexyl-N-cyclohexyl amide;

4-(3H-imidazo[4,5-b]pyridin-1-ylmethyl)-3-methoxybenzoic acid, N-2-butyl-N-cyclohexyl amide;

4-(3H-imidazo[4,5-b]pyridin-1-ylmethyl)-3-methoxybenzoic acid, N-phenyl-N-cyclohexyl amide;

4-(3H-imidazo[4,5-b]pyridin-1-ylmethyl)-3-methoxybenzoic acid, N-3-pentyl-N-cyclohexyl amide;

4-(3H-imidazo[4,5-b]pyridin-1-ylmethyl)-3-methoxybenzoic acid, N-3-methylcyclohexyl-N-cyclopentyl amide;

4-(3H-imidazo[4,5-b]pyridin-1-ylmethyl)-3-methoxybenzoic acid, N-4-methylcyclohexyl-N-cyclopentyl amide;

4-(3H-imidazo[4,5-b]pyridin-1-ylmethyl)-3-methoxybenzoic acid, N-2-methylcyclohexyl-N-cyclopentyl amide;

4-(3H-imidazo[4,5-b]pyridin-1-ylmethyl)-3-methoxybenzoic acid, N-2-methylcyclohexyl-N-isopropyl amide;

4-(3H-imidazo[4,5-b]pyridin-1-ylmethyl)-3-methoxybenzoic acid, N-3-methylcyclohexyl-N-isopropyl amide;

4-(3H-imidazo[4,5-b]pyridin-1-ylmethyl)-3-methoxybenzoic acid, N-3,5-dimethylcyclohexyl-N-isopropyl amide;

4-(3H-imidazo[4,5-b]pyridin-1-ylmethyl)-2-methoxybenzoic acid, N-cyclobutyl-N-cyclohexyl amide;

4-(3H-imidazo[4,5-b]pyridin-1-ylmethyl)-2-methoxybenzoic acid, N-cyclopropyl-N-cyclohexyl amide;

4-(3H-imidazo[4,5-b]pyridin-1-ylmethyl)-2-methoxybenzoic acid, N-cyclopentyl-N-cyclopentyl amide;

4-(3H-imidazo[4,5-b]pyridin-1-ylmethyl)-2-methoxybenzoic acid, N-isopropyl-N-cyclopentyl amide;

4-(3H-imidazo[4,5-b]pyridin-1-ylmethyl)-2-methoxybenzoic acid, N-cyclohexyl-N-cyclohexyl amide;

4-(3H-imidazo[4,5-b]pyridin-1-ylmethyl)-2-methoxybenzoic acid, N-2-butyl-N-cyclohexyl amide;

4-(3H-imidazo[4,5-b]pyridin-1-ylmethyl)-2-methoxybenzoic acid, N-phenyl-N-cyclohexyl amide;

4-(3H-imidazo[4,5-b]pyridin-1-ylmethyl)-2-methoxybenzoic acid, N-3-pentyl-N-cyclohexyl amide;

4-(3H-imidazo[4,5-b]pyridin-1-ylmethyl)-2-methoxybenzoic acid, N-3-methylcyclohexyl-N-cyclopentyl amide;

4-(3H-imidazo[4,5-b]pyridin-1-ylmethyl)-2-methoxybenzoic acid, N-4-methylcyclohexyl-N-cyclopentyl amide;

4-(3H-imidazo[4,5-b]pyridin-1-ylmethyl)-2-methoxybenzoic acid, N-2-methylcyclohexyl-N-cyclopentyl amide;

4-(3H-imidazo[4,5-b]pyridin-1-ylmethyl)-2-methoxybenzoic acid, N-2-methylcyclohexyl-N-isopropyl amide;

4-(3H-imidazo[4,5-b]pyridin-1-ylmethyl)-2-methoxybenzoic acid, N-3-methylcyclohexyl-N-isopropyl amide;

4-(3H-imidazo[4,5-b]pyridin-1-ylmethy)2-methoxybenzoic acid, N-3,5-dimethylcyclohexyl-N-isopropyl amide;

4-[(2-methyl-3H-imidazo[4,5-b]pyridin-1-yl)methyl]-3-methoxybenzoic acid, N-cyclobutyl-N-cyclohexyl amide;

4-[(2-methyl-3H-imidazo[4, 5-b]pyridin-1-yl)methyl]-3-methoxybenzoic acid, N-cyclopropyl-N-cyclohexyl amide;

4-[(2 -methyl-3H-imidazo[4,5-b]pyridin-1-yl)methyl]-3-methoxybenzoic acid, N-cyclopentyl-N-cyclopentyl amide;

4-[(2 -methyl-3H-imidazo[4,5-b]pyridin-1-yl)methyl]-3-methoxybenzoic acid, N-isopropyl-N-cyclopentyl amide;

4-[(2-methyl-3H-imidazo[4,5-b]pyridin-1-yl)methyl]-3-methoxybenzoic acid, N-cyclohexyl-N-cyclohexyl amide;

4-[(2-methyl-3H-imidazo[4,5-b]pyridin-1-yl)methyl]-3-methoxybenzoic acid, N-2-butyl-N-cyclohexyl amide;

4-[(2-methyl-3H-imidazo[4,5-b]pyridin-1-yl)methyl]-3-methoxybenzoic acid, N-phenyl-N-cyclohexyl amide;

4-[(2-methyl-3H-imidazo[4,5-b]pyridin-1-yl)methyl]-3-methoxybenzoic acid, N-3-pentyl-N-cyclohexyl amide;

4-[(2-methyl-3H-imidazo[4,5-b]pyridin-1-yl)methyl]-3-methoxybenzoic acid, N-3-methylcyclohexyl-N-cyclopentyl amide;

4-[(2-methyl-3H-imidazo[4,5-b]pyridin-1-yl)methyl]-3-methoxybenzoic acid, N-4-methylcyclohexyl-N-cyclopentyl amide;

4-[(2-methyl-3H-imidazo[4,5-b]pyridin-1-yl)methyl]-3-methoxybenzoic acid, N-2-methylcyclohexyl-N-cyclopentyl amide;

4-[(2-methyl-3H-imidazo[4,5-b]pyridin-1-yl)methyl]-3-methoxybenzoic acid, N-2-methylcyclohexyl-N-isopropyl amide;

4-[(2-methyl-3H-imidazo[4,5-b]pyridin-1-yl)methyl]-3-methoxybenzoic acid, N-3-methylcyclohexyl-N-isopropyl amide;

4-[(2-methyl-3H-imidazo[4,5-b]pyridin-1-yl)methyl]-3-methoxybenzoic acid, N-3,5-dimethylcyclohexyl-N-isopropyl amide;

4-[(2-(hydroxymethyl)-3H-imidazo[4,5-b]pyridin-1-yl)methyl]-3-methoxybenzoic acid, N-cyclobutyl-N-cyclohexyl amide;

4-[(2-(hydroxymethyl)-3H-imidazo[4,5-b]pyridin-1-yl)methyl]-3-methoxybenzoic acid, N-cyclopropyl-N-cyclohexyl amide;

4-[(2-(hydroxymethyl)-3H-imidazo[4,5-b]pyridin-1-yl)methyl]-3-methoxybenzoic acid, N-cyclopentyl-N-cyclopentyl amide;

4-[(2-(hydroxymethyl)-3H-imidazo[4,5-b]pyridin-1-yl)methyl]-3-methoxybenzoic acid, N-isopropyl-N-cyclopentyl amide;

4-[(2-(hydroxymethyl)-3H-imidazo[4,5-b]pyridin-1-yl)methyl]-3-methoxybenzoic acid, N-cyclohexyl-N-cyclohexyl amide;

4-[(2-(hydroxymethyl)-3H-imidazo[4,5-b]pyridin-1-yl)methyl]-3-methoxybenzoic acid, N-2-butyl-N-cyclohexyl amide;

4-[(2-(hydroxymethyl)-3H-imidazo[4,5-b]pyridin-1-yl)methyl]-3-methoxybenzoic acid, N-phenyl-N-cyclohexyl amide;

4-[(2-(hydroxymethyl)-3H-imidazo[4,5-b]pyridin-1-yl)methyl]-3-methoxybenzoic acid, N-3-pentyl-N-cyclohexyl amide;

4-[(2-(hydroxymethyl)-3H-imidazo[4,5-b]pyridin-1-yl)methyl]-3-methoxybenzoic acid, N-3-methylcyclohexyl-N-cyclopentyl amide;

4-[(2-(hydroxymethyl)-3H-imidazo[4,5-b]pyridin-1-yl)methyl]-3-methoxybenzoic acid, N-4methylcyclohexyl-N-cyclopentyl amide;

4-[(2-(hydroxymethyl)-3H-imidazo[4,5-b]pyridin-1-yl)methyl]-3-methoxybenzoic acid, N-2-methylcyclohexyl-N-cyclopentyl amide;

4-[(2-(hydroxymethyl)-3H-imidazo[4,5-b]pyridin-1-yl)methyl]-3-methoxybenzoic acid, N-2-methylcyclohexyl-N-isopropyl amide;

4-[(2-(hydroxymethyl)-3H-imidazo[4,5-b]pyridin-1-yl)methyl]-3-methoxybenzoic acid, N-3-methylcyclohexyl-N-isopropyl amide;

4-[(2-(hydroxymethyl)-3H-imidazo[4,5-b]pyridin-1-yl)methyl]-3-methoxybenzoic acid, N-3,5-dimethylcyclohexyl-N-isopropyl amide;

4-[(2-(methoxyoxymethyl)-3H-imidazo[4,5-b]pyridin-1-yl)methyl]-3-methoxybenzoic acid, N-cyclobutyl-N-cyclohexyl amide;

4-[(2-(methoxyoxymethyl)-3H-imidazo[4,5-b]pyridin-1-yl)methyl]-3-methoxybenzoic acid, N-cyclopropyl-N-cyclohexyl amide;

4-[(2-(methoxyoxymethyl)-3H-imidazo[4,5-b]pyridin-1-yl)methyl]-3-methoxybenzoic acid, N-cyclopentyl amide;

4-[(2-(methoxyoxymethyl)-3H-imidazo[4,5-b]pyridin-1-yl)methyl]-3-methoxybenzoic acid, N-isopropyl-N-cyclopentyl amide;

4-[(2-(methoxyoxymethyl)-3H-imidazo[4,5-b]pyridin-1-yl)methyl]-3-methoxybenzoic acid, N-cyclohexyl-N-cyclohexyl amide;

4-[(2-(methoxyoxymethyl)-3H-imidazo[4,5-b]pyridin-1-yl)methyl]-3-methoxybenzoic acid, N-2-butyl-N-cyclohexyl amide;

4-[(2-(methoxyoxymethyl)-3H-imidazo[4,5-b]pyridin-1-yl)methyl]-3-methoxybenzoic acid, N-phenyl-N-cyclohexyl amide;

4-[(2-(methoxyoxymethyl)-3H-imidazo[4,5-b]pyridin-1-yl)methyl]-3-methoxybenzoic acid, N-3-pentyl-N-cyclohexyl amide;

4-[(2-(methoxyoxymethyl)-3H-imidazo[4,5-b]pyridin-1-yl)methyl]-3-methoxybenzoic acid, N-3-methylcyclohexyl-N-cyclopentyl amide;

4-[(2-(methoxyoxymethyl)-3H-imidazo[4,5-b]pyridin-1-yl)methyl]-3-methoxybenzoic acid, N-4-methylcyclohexyl-N-cyclopentyl amide;

4-[(2-(methoxyoxymethyl)-3H-imidazo[4,5-b]pyridin-1-yl)methyl]-3-methoxybenzoic acid, N-2-methylcyclohexyl-N-cyclopentyl amide;

4-[(2-(methoxyoxymethyl)-3H-imidazo[4,5-b]pyridin-1-yl)methyl]-3-methoxybenzoic acid, N-2-methylcyclohexyl-N-isopropyl amide;

4-[(2-(methoxyoxymethyl)-3H-imidazo[4,5-b]pyridin-1-yl)methyl]-3-methoxybenzoic acid, N-3-methylcylohexyl-N-isopropyl amide;

4-[(2-(methoxyoxymethyl)-3H-imidazo[4,5-b]pyridin-1-yl)methyl]-3-methoxybenzoic acid, N-3,5-dimethylcyclohexyl-N-isopropyl amide;

4-[(2-(dimethylaminomethyl)-3H-imidazo[4,5-b]pyridin-1-yl)methyl]-3-methoxybenzoic acid, N-cyclobutyl-N-cyclohexyl amide;

4-[(2-(dimethylaminomethyl)-3H-imidazo[4,5-b]pyridin-1-yl)methyl]-3-methoxybenzoic acid, N-cyclopropyl-N-cyclohexyl amide;

4-[(2-(dimethylaminomethyl)-3H-imidazo[4,5-b]pyridin-1-yl)methyl]-3-methoxybenzoic acid, N-cyclopentyl-N-cyclopentyl amide;

4-[(2-(dimethylaminomethyl)-3H-imidazo[4,5-b]pyridin-1-yl)methyl]-3-methoxybenzoic acid, N-isopropyl-N-cyclopentyl amide;

4-[(2-(dimethylaminomethyl)-3H-imidazo[4,5-b]pyridin-1-yl)methyl]-3-methoxybenzoic acid, N-cyclohexyl-N-cyclohexyl amide;

4-[(2-(dimethylaminomethyl)-3H-imidazo[4,5-b]pyridin-1-yl)methyl]-3-methoxybenzoic acid, N-2-butyl-N-cyclohexyl amide;

4-[(2-(dimethylaminomethyl)-3H-imidazo[4,5-b]pyridin-1-yl)methyl]-3-methoxybenzoic acid, N-phenyl-N-cyclohexyl amide;

4-[(2-(dimethylaminomethyl)-3H-imidazo[4,5-b]pyridin-1-yl)methyl]-3-methoxybenzoic acid, N-3-pentyl-N-cyclohexyl amide;

4-[(2-(dimethylaminomethyl)-3H-imidazo[4,5-b]pyridin-1-yl)methyl]-3-methoxybenzoic acid, N-3-methylcyclohexyl-N-cyclopentyl amide;

4-[(2-(dimethylaminomethyl)-3H-imidazo[4,5-b]pyridin-1-yl)methyl]-3-methoxybenzoic acid, N-4-methylcyclohexyl-N-cyclopentyl amide;

4-[(2-(dimethylaminomethyl)-3H-imidazo[4,5-b]pyridin-1-yl)methyl]-3-methoxybenzoic acid, N-2-methylcyclohexyl-N-cyclopentyl amide;

4-[(2-(dimethylaminomethyl)-3H-imidazo[4,5-b]pyridin-1-yl)methyl]-3-methoxybenzoic acid, N-2-methylcyclohexyl-N-isopropyl amide;

4-[(2-(dimethylaminomethyl)-3H-imidazo[4,5-b]pyridin-1-yl)methyl]-3-methoxybenzoic acid, N-3-methylcyclohexyl-N-isopropyl amide;

4-[(2-(dimethylaminomethyl)-3H-imidazo[4,5-b]pyridin-1-yl)methyl]-3-methoxybenzoic acid, N-3,5-dimethylcyclohexyl-N-isopropyl amide;

4-[(2-(dimethylamino)-3H-imidazo[4,5-b]pyridin-1-yl)methyl]-3-methoxybenzoic acid, N-cyclobutyl-N-cyclohexyl amide;

4-[(2-(dimethylamino)-3H-imidazo[4,5-b]pyridin-1-yl)methyl]-3-methoxybenzoic acid, N-cyclopropyl-N-cyclohexyl amide;

4-[(2-(dimethylamino)-3H-imidazo[4,5-b]pyridin-1-yl)methyl]-3-methoxybenzoic acid, N-cyclopentyl-N-cyclopentyl amide;

4-[(2-(dimethylamino)-3H-imidazo[4,5-b]pyridin-1-yl)methyl]-3-methoxybenzoic acid, N-isopropyl-N-cyclopentyl amide;

4-[(2-(dimethylamino)-3H-imidazo[4,5-b]pyridin-1-yl)methyl]-3-methoxybenzoic acid, N-cyclohexyl-N-cyclohexyl amide;

4-[(2-(dimethylamino)-3H-imidazo[4,5-b]pyridin-1-yl)methyl]-3-methoxybenzoic acid, N-2-butyl-N-cyclohexyl amide;

4-[(2-(dimethylamino)-3H-imidazo[4,5-b]pyridin-1-yl)methyl]-3-methoxybenzoic acid, N-phenyl-N-cyclohexyl amide;

4-[(2-(dimethylamino)-3H-imidazo[4,5-b]pyridin-1-yl)methyl]-3-methoxybenzoic acid, N-3-pentyl-N-cyclohexyl amide;

4-[(2-(dimethylamino)-3H-imidazo[4,5-b]pyridin-1-yl)methyl]-3-methoxybenzoic acid, N-3-methylcyclohexyl-N-cyclopentyl amide;

4-[(2-(dimethylamino)-3H-imidazo[4,5-b]pyridin-1-yl)methyl]-3-methoxybenzoic acid, N-4-methylcyclohexyl-N-cyclopentyl amide;

4-[(2-(dimethylamino)-3H-imidazo[4,5-b]pyridin-1-yl)methyl]-3-methoxybenzoic acid, N-2-methylcyclohexyl-N-cyclopentyl amide;

4-[(2-(dimethylamino)-3H-imidazo[4,5-b]pyridin-1-yl)methyl]-3-methoxybenzoic acid, N-2-methylcyclohexyl-N-isopropyl amide;

4-[(2-(dimethylamino)-3H-imidazo[4,5-b]pyridin-1-yl)methyl]-3-methoxybenzoic acid, N-3-methylcyclohexyl-N-isopropyl amide;

4-[(2-(dimethylamino)-3H-imidazo[4,5-b]pyridin-1-yl)methyl]-3-methoxybenzoic acid, N-3,5-dimethylcyclohexyl-N-isopropyl amide;

4-[(2-(hydroxymethyl)-3H-imidazo[4,5-b]pyridin-1-yl)methyl]-2-methoxybenzoic acid, N-cyclobutyl-N-cyclohexyl amide;

4-[(2-(hydroxymethyl)-3H-imidazo[4,5-b]pyridin-1-yl)methyl]-2-methoxybenzoic acid, N-cyclopropyl-N-cyclohexyl amide;

4-[(2-(hydroxymethyl)-3H-imidazo[4,5-b]pyridin-1-yl)methyl]-2-methoxybenzoic acid, N-cyclopentyl-N-cyclopentyl amide;

4-[(2-(hydroxymethyl)-3H-imidazo[4,5-b]pyridin-1-yl)methyl]-2-methoxybenzoic acid, N-isopropyl-N-cyclopentyl amide;

4-[(2-(hydroxymethyl)-3H-imidazo[4,5-b]pyridin-1-yl)methyl]-2-methoxybenzoic acid, N-cyclohexyl-N-cyclohexyl amide;

4-[(2-(hydroxymethyl)-3H-imidazo[4,5-b]pyridin-1-yl)methyl]-2-methoxybenzoic acid, N-2-butyl-N-cyclohexyl amide;

4-[(2-(hydroxymethyl)-3H-imidazo[4,5-b]pyridin-1-yl)methyl]-2-methoxybenzoic acid, N-phenyl-N-cyclohexyl amide;

4-[(2-(hydroxymethyl)-3H-imidazo[4,5-b]pyridin-1-yl)methyl]-2-methoxybenzoic acid, N-3-pentyl-N-cyclohexyl amide;

4-[(2-(hydroxymethyl)-3H-imidazo[4,5-b]pyridin-1-yl)methyl]-2-methoxybenzoic acid, N-3-methylcyclohexyl-N-cyclopentyl amide;

4-[(2-(hydroxymethyl)-3H-imidazo[4,5-b]pyridin-1-yl)methyl]-2-methoxybenzoic acid, N-4-methylcyclohexyl-N-cyclopentyl amide;

4-[(2-(hydroxymethyl)-3H-imidazo[4,5-b]pyridin-1-yl)methyl]-2-methoxybenzoic acid, N-2-methylcyclohexyl-N-cyclopentyl amide;

4-[(2-(hydroxymethyl)-3H-imidazo[4,5-b]pyridin-1-yl)methyl]-2-methoxybenzoic acid, N-2-methylcyclohexyl-N-isopropyl amide;

4-[(2-(hydroxymethyl)-3H-imidazo[4,5-b]pyridin-1-yl)methyl]-2-methoxybenzoic acid, N-3-methylcyclohexyl-N-isopropyl amide;

4-[(2-(hydroxymethyl)-3H-imidazo[4,5-b]pyridin-1-yl)methyl]-2-methoxybenzoic acid, N-3,5-dimethylcyclohexyl-N-isopropyl amide;

4-[(2-(methoxyoxymethyl)-3H-imidazo[4,5-b]pyridin-1-yl)methyl]-2-methoxybenzoic acid, N-cyclobutyl-N-cyclohexyl amide;

4-[(2-(methoxyoxymethyl)-3H-imidazo[4,5-b]pyridin-1-yl)methyl]-2-methoxybenzoic acid, N-cyclopropyl-N-cyclohexyl amide;

4-[(2-(methoxyoxymethyl)-3H-imidazo[4,5-b]pyridin-1-yl)methyl]-2-methoxybenzoic acid, N-cyclopentyl-N-cyclopentyl amide;

4-[(2-(methoxyoxymethyl)-3H-imidazo[4,5-b]pyridin-1-yl)methyl]-2-methoxybenzoic acid, N-isopropyl-N-cyclopentyl amide;

4-[(2-(methoxyoxymethyl)-3H-imidazo[4,5-b]pyridin-1-yl)methyl]-2-methoxybenzoic acid, N-cyclohexyl-N-cyclohexyl amide;

4-[(2-(methoxyoxymethyl)-3H-imidazo[4,5-b]pyridin-1-yl)methyl]-2-methoxybenzoic acid, N-2-butyl-N-cyclohexyl amide;

4-[(2-(methoxyoxymethyl)-3H-imidazo[4,5-b]pyridin-1-yl)methyl]-2-methoxybenzoic acid, N-phenyl-N-cyclohexyl amide;

4-[(2-(methoxyoxymethyl)-3H-imidazo[4,5-b]pyridin-1-yl)methyl]-2-methoxybenzoic acid, N-3-pentyl-N-cyclohexyl amide;

4-[(2-(methoxyoxymethyl)-3H-imidazo[4,5-b]pyridin-1-yl)methyl]-2-methoxybenzoic acid, N-3-methylcyclohexyl-N-cyclopentyl amide;

4-[(2-(methoxyoxymethyl)-3H-imidazo[4,5-b]pyridin-1-yl)methyl]-2-methoxybenzoic acid, N-4-methylcyclohexyl-N-cyclopentyl amide;

4-[(2-(methoxyoxymethyl)-3H-imidazo[4,5-b]pyridin-1-yl)methyl]-2-methoxybenzoic acid, N-2-methylcyclohexyl-N-cyclopentyl amide;

4-[(2-(methoxyoxymethyl)-3H-imidazo[4,5-b]pyridin-1-yl)methyl]-2-methoxybenzoic acid, N-2-methylcyclohexyl-N-isopropyl amide;

4-[(2-(methoxyoxymethyl)-3H-imidazo[4,5-b]pyridin-1-yl)methyl]-2-methoxybenzoic acid, N-3-methylcyclohexyl-N-isopropyl amide;

4-[(2-(methoxyoxymethyl)-3H-imidazo[4,5-b]pyridin-1-yl)methyl]-2-methoxybenzoic acid, N-3,5-dimethylcyclohexyl-N-isopropyl amide;

4-[(2-(dimethylaminomethyl)-3H-imidazo[4,5-b]pyridin-1-yl)methyl]-2-methoxybenzoic acid, N-cyclobutyl-N-cyclohexyl amide;

4-[(2-(dimethylaminomethyl)-3H-imidazo[4,5-b]pyridin-1-yl)methyl]-2-methoxybenzoic acid, N-cyclopropyl-N-cyclohexyl amide;

4-[(2-(dimethylaminomethyl)-3H-imidazo[4,5-b]pyridin-1-yl)methyl]-2-methoxybenzoic acid, N-cyclopentyl-N-cyclopentyl amide;

4-[(2-(dimethylaminomethyl)-3H-imidazo[4,5-b]pyridin-1-yl)methyl]-2-methoxybenzoic acid, N-isopropyl-N-cyclopentyl amide;

4-[(2-(dimethylaminomethyl)-3H-imidazo[4,5-b]pyridin-1-yl)methyl]-2-methoxybenzoic acid, N-cyclohexyl-N-cyclohexyl amide;

4-[(2-(dimethylaminomethyl)-3H-imidazo[4,5-b]pyridin-1-yl)methyl]-2-methoxybenzoic acid, N-2-butyl-N-cyclohexyl amide;

4-[(2-(dimethylaminomethyl)-3H-imidazo[4,5-b]pyridin-1-yl)methyl]-2-methoxybenzoic acid, N-phenyl-N-cyclohexyl amide;

4-[(2-(dimethylaminomethyl)-3H-imidazo[4,5-b]pyridin-1-yl)methyl]-2-methoxybenzoic acid, N-3-phenyl-N-cyclohexyl amide;

4-[(2-(dimethylaminomethyl)-3H-imidazo[4,5-b]pyridin-1-yl)methyl]-2-methoxybenzoic acid, N-3-methylcyclohexyl-N-cyclopentyl amide;

4-[(2-(dimethylaminomethyl)-3H-imidazo[4,5-b]pyridin-1-yl)methyl]-2-methoxybenzoic acid, N-4-methylcyclohexyl-N-cyclopentyl amide;

4-[(2-(dimethylaminomethyl)-3H-imidazo[4,5-b]pyridin-1-yl)methyl]-2-methoxybenzoic acid, N-2-methylcyclohexyl-N-cyclopentyl amide;

4-[(2-(dimethylaminomethyl)-3H-imidazo[4,5-b]pyridin-1-yl)methyl]-2-methoxybenzoic acid, N-2-methylcyclohexyl-N-isopropyl amide;

4-[(2-(dimethylaminomethyl)-3H-imidazo[4,5-b]pyridin-1-yl)methyl]-2-methoxybenzoic acid, N-3-methylcyclohexyl-N-isopropyl amide;

4-[(2-(dimethylaminomethyl)-3H-imidazo[4,5-b]pyridin-1-yl)methyl]-2-methoxybenzoic acid, N-3,5-dimethycyclohexyl-N-isopropyl amide;

4-[(2-(dimethylamino)-3H-imidazo[4,5-b]pyridin-1-yl)methyl]-2-methoxybenzoic acid, N-cyclobutyl-N-cyclohexyl amide;

4-[(2-(dimethylamino)-3H-imidazo[4,5-b]pyridin-1-yl)methyl]-2-methoxybenzoic acid, N-cyclopropyl-N-cyclohexyl amide;

4-[(2-(dimethylamino)-3H-imidazo[4,5-b]pyridin-1-yl)methyl]-2-methoxybenzoic acid, N-cyclopentyl-N-cyclopentyl amide;

4-[(2-(dimethylamino)-3H-imidazo[4,5-b]pyridin-1-yl)methyl]-2-methoxybenzoic acid, N-isopropyl-N-cyclopentyl amide;

4-[(2-(dimethylamino)-3H-imidazo[4,5-b]pyridin-1-yl)methyl]-2-methoxybenzoic acid, N-cyclohexyl-N-cyclohexyl amide;

4-[(2-(dimethylamino)-3H-imidazo[4,5-b]pyridin-1-yl)methyl]-2-methoxybenzoic acid, N-2-butyl-N-cyclohexyl amide;

4-[(2-(dimethylamino)-3H-imidazo[4,5-b]pyridin-1-yl)methyl]-2-methoxybenzoic acid, N-phenyl-N-cyclohexyl amide;

4-[(2-(dimethylamino)-3H-imidazo[4,5-b]pyridin-1-yl)methyl]-2-methoxybenzoic acid, N-3-pentyl-N-cyclohexyl amide;

4-[(2-(dimethylamino)-3H-imidazo[4,5-b]pyridin-1-yl)methyl]-2-methoxybenzoic acid, N-3-methylcyclohexyl-N-cyclopentyl amide;

4-[(2-(dimethylamino)-3H-imidazo[4,5-b]pyridin-1-yl)methyl]-2-methoxybenzoic acid, N-4-methylcyclohexyl-N-cyclopentyl amide;

4-[(2-(dimethylamino)-3H-imidazo[4,5-b]pyridin-1-yl)methyl]-2-methoxybenzoic acid, N-2-methylcyclohexyl-N-cyclopentyl amide;

4-[(2-(dimethylamino)-3H-imidazo[4,5-b]pyridin-1-yl)methyl]-2-methoxybenzoic acid, N-2-methylcyclohexyl-N-isopropyl amide;

4-[(2-(dimethylamino)-3H-imidazo[4,5-b]pyridin-1-yl)methyl]-2-methoxybenzoic acid, N-3-methylcyclohexyl-N-isopropyl amide; and 4-[(2-(dimethylamino)-3H-imidazo[4,5-b]pyridin-1-yl)methyl]-2-methoxybenzoic acid, N-3,5-dimethylcyclohexyl-N-isopropyl amide.

SYNTHETIC PROCEDURES

Compounds of Formula I may be prepared in accordance with five general procedures, as shown in General Procedures A through E, below:

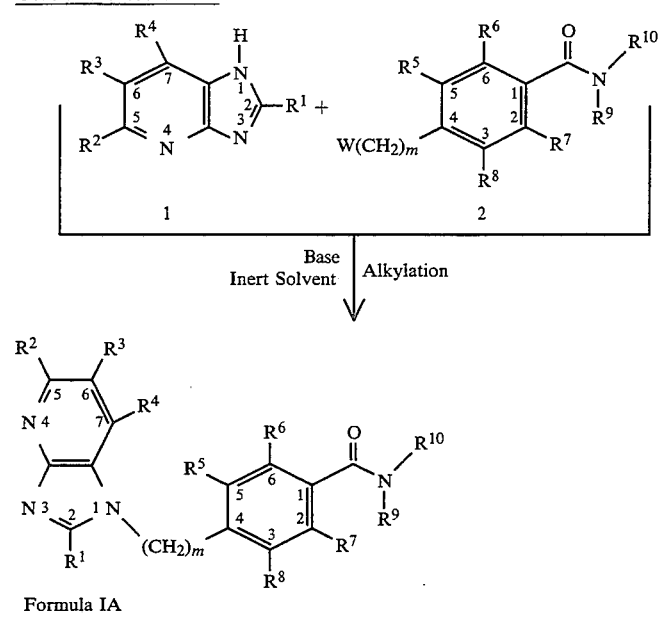

Formula IA

General Procedure A:

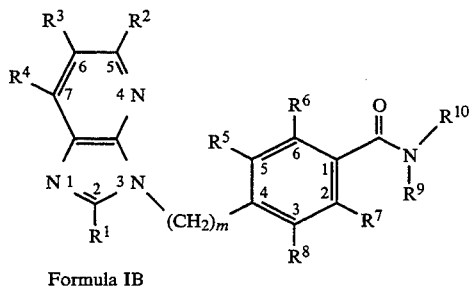

Formula IB wherein m, $R^1$–$R^{10}$ are defined above and W is selected from halo, alkylsulfonyloxy and arylsulfonyloxy.

General Procedure A shows a general method for synthesizing compounds of Formula I, including 1H-imidazole[4,5-b]pyridine compounds of Formula IA and 3H-imidazole[4,5-b]pyridine compounds of Formula IB. Imidazopyridines 1 are accessible, for example, by heating the appropriately substituted 2,3-diaminopyridine with the appropriate carboxylic acid ($R^1CO_2H$). For example, 1(H)-imidazo[4,5-b]pyridine (1: $R^1$, $R^2$, $R^3$ and $R^4$=H) is synthesized by refluxing a solution of 2,3-diaminopyridine in formic acid, as described in U.S. Pat. No. 4,962,106. An appropriate alkyl halide 2 may be synthesized by the methods shown in U.S. Pat. No. 5,019,581. Conversion to target 1H-compounds of Formula IA and 3H-compounds of Formula IB is carried out by reacting imidazopyridine 1 with the appropriate benzylic bromide 2 in the presence of a base, such as sodium or potassium hydride or cesium carbonate, in an inert solvent such as dimethylformamide, dimethylacetamide, acetonitrile, tetrahydrofuran, or dimethoxyethane. Separation of the various regioisomers is carried out by chromatography on a suitable adsorbent, such as silica gel, using mixtures of methylene chloride, methanol and ammonium hydroxide as eluents.

General Procedure B:

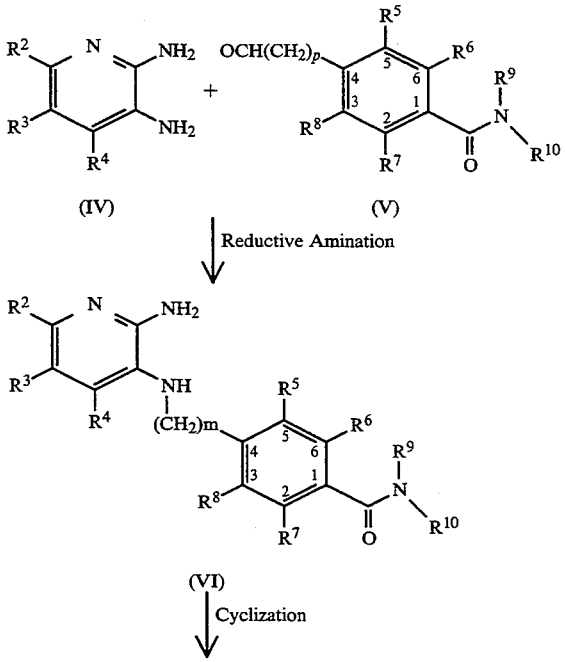

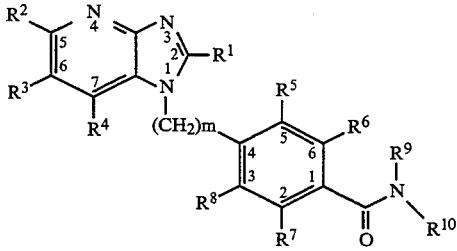

Formula IA wherein m and $R^1$–$R^{10}$ are as defined above, and p is a number from zero to five, inclusive.

General Procedure B shows a general method for synthesizing 1H-regioisomer compounds of Formula IA. The target compounds may be prepared by starting with substituted 2,3-diaminopyridine (IV). The reductive amination of substituted 2,3-diaminopyridine (IV) with aldehyde (V), using reducing agents such as sodium borohydride or sodium cyanoborohydride in the presence of acid, gives the 3-alkylamino derivative (VI). Appropriate solvents for this type of transformation are, for example, ethanol and iso-propanol, with or without the presence of water. The reductive amination may also be carried out in two steps by first forming a Schiff base followed by reduction. The Schiff base formation can take place in non-polar solvents such as benzene, toluene, tetrahydrofuran, ether and dioxane, whereas the reduction of Schiff base can be carried out by using the reducing agents mentioned above. The cyclization of (VI) to the target compounds of Formula IA can be carried out by reacting with substituted carboxylic acids ($R^1CO_2H$) or the carboxylic equivalents such as trialkyl orthoformates [$R^1C(OR)_3$]. The reaction of (VI) with carboxylic acid derivatives may be carried out by heating at higher temperature with or without the presence of acids such as polyphosphoric acid. The reaction of (V) with trialkyl orthoformate may be carried out in the presence of acid catalysts such as p-toluenesulfonic acid.

General Procedure C:

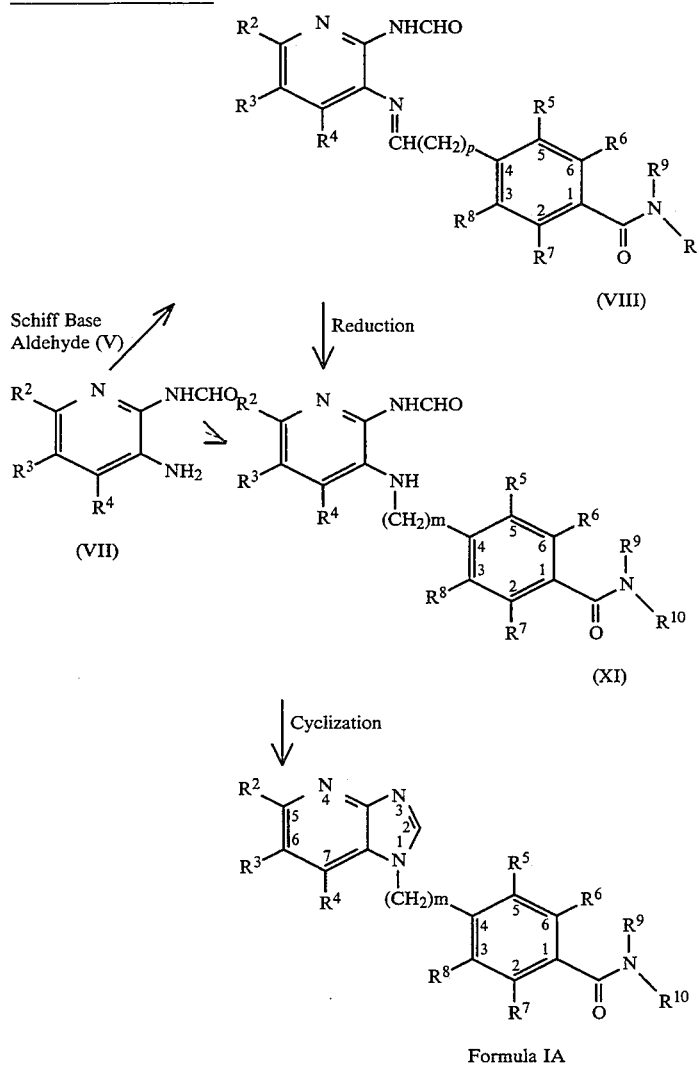

Formula IA wherein m, p and $R^1$–$R^{10}$ are as defined above.

General Procedure C shows another method for synthesizing 1H-regioisomer compounds of Formula IA. The target compounds may be prepared by starting with substituted 2-formamido-3-aminopyridines (VII). The reaction of VII with aldehyde (V) using catalyst such as Ti(O-iPr)$_4$ or Pt on carbon gives the Schiff base (VIII). The reduction of Schiff base (VIII) gives the 3-amino derivative (XI). The reduction of imine (VIII) may be carried out under hydrogenation at pressure of (50–200 psi) using catalysts such as Pt on carbon or palladium. The compound (XI) can be cyclized to the desired compounds of Formula IA by treating with a nonnucleophilic base in the presence of a polar solvent such as N,N-dimethylformamide, N,N-dimethylacetamide, dimethylsulfoxide, N-methylpyrrolidinone and the like. Suitable bases for this reaction are, for example, cesium carbonate, potassium carbonate, sodium carbonate, 1,8-diazabicyclo[5.4.0]undecane-7-ene (DBU), N,N-diisopropylethylamine and the like. The cyclization reaction may be carried out at temperature in a range from about 15° C. to about 120° C.

General Procedure D:

Within the scope of the present invention, there is provided another regio-selective method for making compounds of Formula IA. This method, as shown in General Procedure D, provides a "one-step" synthesis of compounds of Formula IA. In addition to the benefits of less material handling/transfer and fewer process-step manipulations, this method provides a reaction product containing only one isomer, namely, the 1H-regioisomer of compounds embraced by general Formula IA.

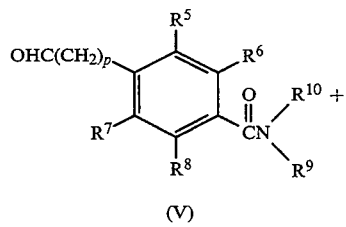

(V)

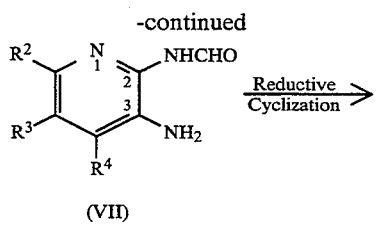

(VII)

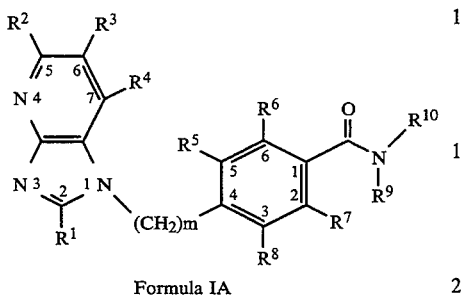

Formula IA wherein m, $R^1$–$R^{10}$ are as defined above, and p is a number from zero to five, inclusive.

In this "one-step" method, an appropriately-substituted aldehyde V is condensed with an appropriately-substituted 3-amino-2-formamidopyridine (VII) to form an intermediate containing an imine moiety. The resulting imine-containing intermediate is not isolated but reacted further in situ. In the presence of a borane·pyridine complex, the imine bond is reduced and the formyl group is cyclized to a 5-member imidazole ring, with consequent loss of water. The reaction is carried out in a polar organic aprotic solvent, e.g., methylene chloride, and a mild organic acid, e.g., acetic acid, at a temperature in a range from about 15° C. to about 45° C. The reaction solution is stirred in this temperature range from about one hour to about 18 hours, after which the reaction is quenched and neutralized to a pH in a range from about 5 to about 9 with a dilute base, e.g., ammonium hydroxide. The product compound of Formula IA is extracted and purified by conventional techniques. The pyridine reactant (VII) may be prepared from substituted-2-amino-3-nitro-pyridine derivatives by formylation using, for example, acetic anhydride and formic acid, followed by catalytic hydrogenation using catalysts such as Raney-nickel or palladium on carbon. The aldehyde reactant (V) may be synthesized by conventional methods, and one such method is shown below for aldehyde reactant 1, which is a sub-generic description of aldehyde (V).

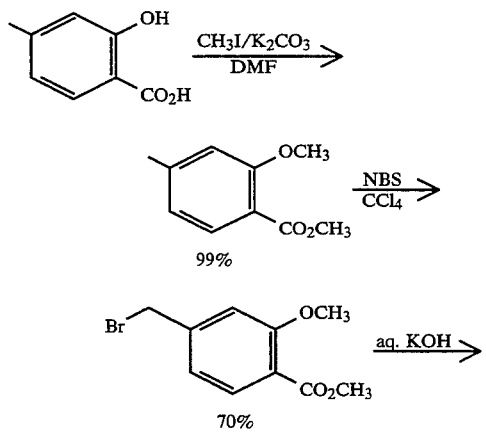

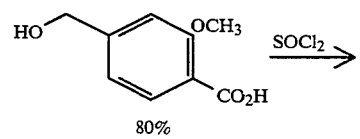

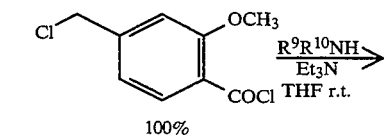

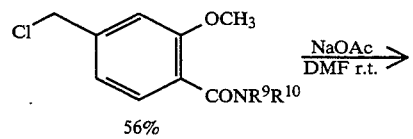

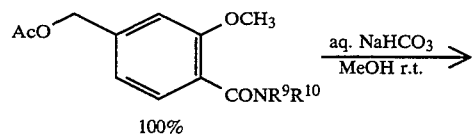

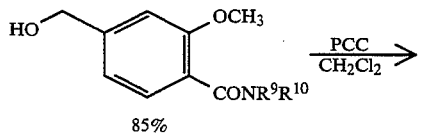

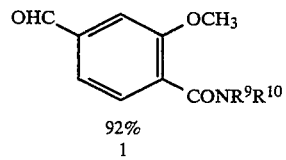

The yields shown above are for reactants wherein $R^9$ is isopropyl and $R^{10}$ is cyclohexyl. The starting 4-methylsalicylic acid may be alkylated by treatment with an alkylating agent, such as methyl iodide, in the presence of a base, such as $K_2CO_3$, in a solvent such as dimethylformamide. In so doing, the carboxylic acid ester is also formed. The 4-methyl group is then functionalized by, for example, free radical halogenation with reagents such as N-bromosuccinimide, in the presence of an initiator such as light and/or bisazoisobutyronitrile in a suitable solvent such as carbon tetrachloride. Saponification of the ester to the carboxylic acid may be achieved by treatment with a base such as potassium hydroxide in water. Saponification under these conditions normally replaces the benzylic halogen with a hydroxyl group. The amide may be prepared by first, conversion to the activated carboxylic acid using a halogenating agent such as thionyl chloride, and then treatment of the resulting acid chloride with the appropriate amine $R^9R^{10}NH$. This reaction normally replaces the benzylic hydroxyl group with a halogen. If thionyl chloride is used as the halogenating agent, the halogen is chloride. To convert the halomethyl group to an aldehyde, the benzylic halogen is replaced by a displacement reaction using an oxygen nucleophile. An example of such an agent is sodium acetate. This displacement is carried out in a suitable solvent such as dimethylformamide at a temperature in a range from about 50° C. to about 100° C. The acetate is saponified to the benzylic alcohol by treatment with a mild base such as NaHCO3 in an aqueous solvent such as aqueous methanol. Oxidation of the alcohol to the aldehyde is achieved using an oxidizing agent such as pyridinium chlorochromate in an appropriate solvent such as methylene chloride.

General Scheme E:

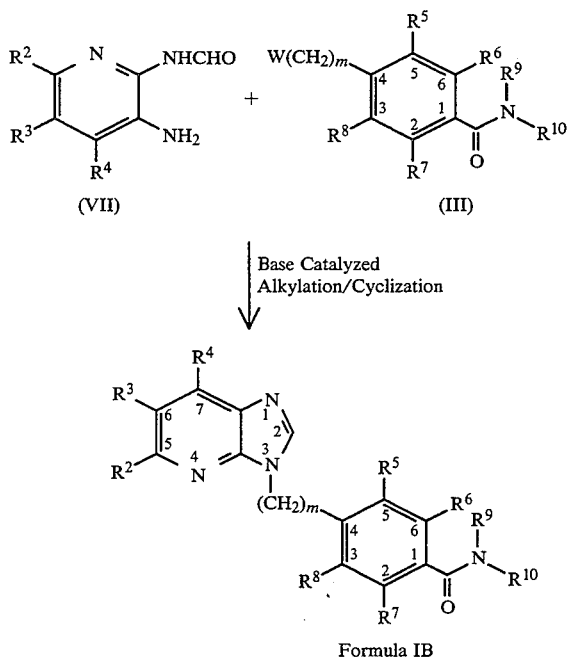

Formula IB wherein m, R¹–R¹⁰ and W are as defined above.

General Procedure E shows a method for synthesizing 3H-regioisomer compounds of Formula IB. N-3 substituted imidazo[4,5-b]pyridine derivatives may be prepared by starting with appropriately substituted 2-formamido-3-aminopyridine compound (VII). The reaction of (VII) with compound (III) in the presence of a base gives mainly the N-3 substituted imidazo[4,5-b]pyridine derivative. This reaction may be carried out in a polar solvent such as N,N-dimethylformamide, N,N-dimethylacetamide, dimethylsulfoxide, N-methylpyrrolidinone, acetonitrile, tetrahydrofuran and the like. Suitable bases for this reaction are, for example, cesium carbonate, potassium carbonate, sodium carbonate, 1,8-diazabicyclo[5.4.0]-undecane-7-ene (DBU), N, N-diisopropylethylamine, triethylamine and the like.

The following Examples 1–23 are detailed descriptions of the synthetic steps for preparing compounds of the invention. These detailed preparations fall within the scope of, and serve to exemplify, the more generally described procedures above. These Examples 1–23 are presented for illustrative purposes only and are not intended as a restriction on the scope of the invention. Most of the commercially-available materials were obtained from Alderich Chemical Co., Milwaukee, Wis.

EXAMPLE 1

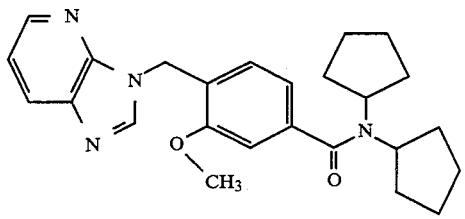

N, N-dicyclopentyl-4-(3H-imidazo[4,5-b]pyridin-1-ylmethyl)-3-methoxybenzamide

To a stirred solution of imidazo[4,5-b]pyridine (350 mg, 2.94 mmol) in N,N-dimethylformamide (25 mL), sodium hydride (118 mg, 60% dispersion in mineral oil, 2.94 mmol) was added. After stirring for 2 hr, 4-bromomethyl-3-methoxy-N,N-dicyclopentyl benzamide (1.4 g, 3.57 mmol) was added in small installments over 10 min. The reaction mixture was stirred under argon at 25° C. After 18 h, the reaction was quenched by adding acetic acid (0.5 mL) and the solvent was removed under reduced pressure at <45° C. The crude mixture (2 g) was chromatographed (silica gel, CH2Cl2-MeOH-NH4OH 90-10-1) to give the title compound. (320 mg, 26%) DSC 185° C.; Anal calcd. for $C_{25}H_{30}N_4O_2 \cdot 0.6H_2O$: C, 69.94; H, 7.32; N, 13.05. Found C, 69.96; H, 7.58; N, 12.68.

EXAMPLE 2

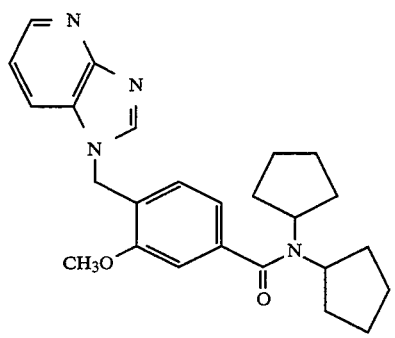

N, N-dicyclopentyl-4-(1H-imidazo[4,5-b]pyridin-1-ylmethyl)-3-methoxybenzamide

To a stirred solution of imidazo[4,5-b]pyridine (350 mg, 2.94 mmol) in N,N-dimethylformamide (25 mL), sodium hydride (118 mg, 60% dispersion in mineral oil, 2.94 mmol) was added. After stirring for 2 hr, 4-bromomethyl-3-methoxy-N,N-dicyclopentyl benzamide (1.4 g, 3.57 mmol) was added in small installments over 10 min. The reaction mixture was stirred under argon at 25° C. After 18 h, the reaction was quenched by adding acetic acid (0.5 mL) and the solvent was removed under reduced pressure at <45° C. The crude mixture (2 g) was chromatographed (silica gel, CH2Cl2-MeOH-NH4OH 90-10-1) to give the title compound. (160 mg, 13%) DSC 198° C.; Anal calcd. for $C_{25}H_{30}N_4O_2 \cdot 0.7H_2O$: C, 69.65; H, 7.34; N, 12.99. Found C, 69.72; H, 7.39; N, 12.63.

EXAMPLE 3

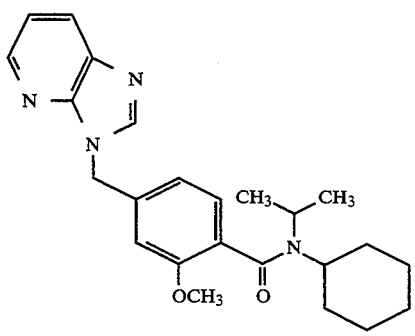

N-cyclohexyl-4-(3H-imidazo[4,5-b]pyridin-3-ylmethyl)-2-methoxy-N-(1-methylethyl)benzamide To a stirred solution of imidazo[4,5-b]pyridine (350 mg, 2.94 mmol) in N,N-dimethylformamide (25 mL), sodium hydride (118 mg, 60% dispersion in mineral oil, 2.94 mmol) was added. After stirring for 2 hr, 4-bromomethyl-2-methoxy-N-isopropyl,N-cyclohexyl benzamide (1.07 g, 2.94 mmol) was added over 10 min. The reaction mixture was stirred under argon at 25° C. After 18 h, the reaction was quenched by adding acetic acid (0.5 mL) and the solvent was removed under reduced pressure at <45° C. The crude mixture (1.6 g) was chromatographed (silica gel, $CH_2Cl_2$-MeOH-$NH_4OH$ 90-10-1) to give the title compound. (268 mg, 23%) mp 96–98° C.; Anal calcd. for $C_{24}H_{30}N_4O_2 \cdot 0.9 \cdot H_2O$: C, 68.19; H, 7.58; N, 13.25. Found C, 68.18; H, 7.42; N, 13.13.

EXAMPLE 4

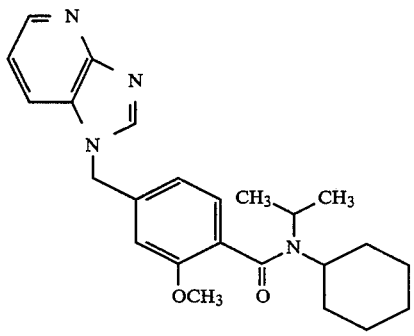

N-cyclohexyl-4-(1H-imidazo[4,5-b]pyridin-1-ylmethyl)-2-methoxy-N-(1-methylethyl)benzamide

Preparation A

To a stirred solution of imidazo[4,5-b]pyridine (350 mg, 2.94 mmol) in N,N-dimethylformamide (25 mL), sodium hydride (118 mg, 60% dispersion in mineral oil, 2.94 mmol) was added. After stirring for 2 hr, 4-bromomethyl-2-methoxy-N-isopropyl, N-cyclohexyl benzamide (1.07 g, 2.94 mmol) was added over 10 min. The reaction mixture was stirred under argon at 25° C. After 18 h, the reaction was quenched by adding acetic acid (0.5 mL) and the solvent was removed under reduced pressure at <45 ° C. The crude mixture (1.6 g) was chromatographed (silica gel, $CH_2Cl_2$-MeOH-$NH_4OH$ 90-10-1) to give the title compound. (175 mg, 15%) mp 191–93° C.; Anal calcd. for $C_{24}H_{30}N_4O_2 \cdot 1.2 \cdot H_2O$: C, 67.33; H, 7.63; N, 13.09. Found C, 67.37; H, 7.49; N, 12.99.

Preparation B:

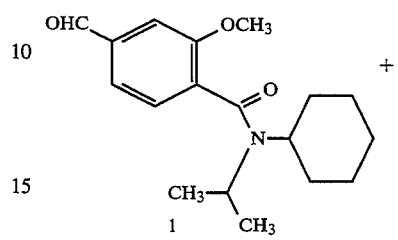

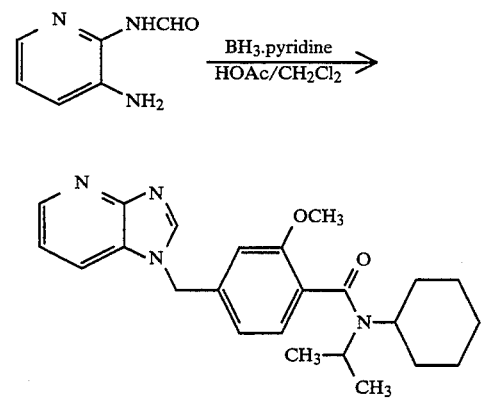

Ex. #4 Title Compound

To a solution of 3-amino-2-formamidopyridine (3.67 g, 26.8 mmol) and aldehyde I (10.0 g, 33.0 mmol) in methylene chloride (50 mL) and acetic acid (50 mL) at room temperature, borane-pyridine complex (2.73 mL, 2.52 g, 27.0 mmol) was added. Some exothermicity was observed. After stirring the reaction solution at room temperature for 1.5 hrs., the reaction was quenched and neutralized to pH 7 with dilute ammonium hydroxide and extracted several times with methylene chloride. The combined organic layers were dried ($Na_2SO_4$), filtered and concentrated in vacuo to give a brown oil. The crude product was chromatographed on silica gel using mixtures of $CH_2Cl_2$:MeOH:$NH_4OH$ as the eluent to yield a crystalline solid: m.p. (capillary) 193–195° C. $^1$H NMR (300 MHz, $CD_3OD$, ppm): 0.08–1.90 (m, 16H); 2.55 (m, 1H); 3.10 (m, 1H); 3.63 (m, 1H); 3.80 (s, 3H); 5.58 (d, J=6 Hz, 2H); 6.90 (d, J=7.5 Hz, 1H); 7.05 (d, J<3 Hz, 1H); 7.10 (d, J=10 Hz, 1H); 7.30 (m, 1H); 7.95 (m, 1H); 8.45 (m, 1H); 8.60 (s, 1H). Anal. Calcd. for $C_{24}H_{30}N_4O_2C$, 70.91; H, 7.44; N, 13.78. Found: C, 70.71; H, 7.51; N, 13.75.

EXAMPLE 5

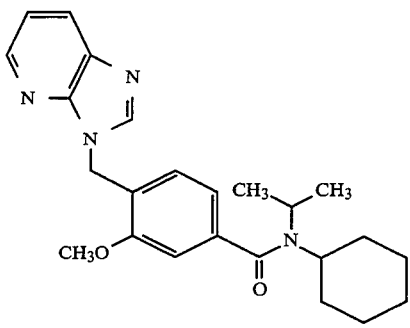

N-cyclohexyl-4-(3H-imidazo[4,5-b]pyridin-3-ylmethyl)-3-methoxy-N-(1-methylethyl)benzamide

Preparation A

To a stirred solution of imidazo[4,5-b]pyridine (350 mg, 2.94 mmol) in N,N-dimethylformamide (25 mL), sodium hydride (120mg, 60% dispersion in mineral oil, 2.94 mmol) was added. After stirring for 2 hr, 4-bromomethyl-3-methoxy-N-isopropyl,N-cyclohexyl benzamide (1.07 g, 2.94 mmol) was added over 15 min. The reaction mixture was stirred under argon at 25° C. After 18 h, the reaction was quenched by adding acetic acid (0.5 mL) and the solvent was removed under reduced pressure at <45° C. The crude mixture (1.58 g) was chromatographed (silica gel, CH$_2$Cl$_2$-MeOH-NH$_4$OH 90-10-1) to give the title compound. (315 mg, 26%) DSC 198° C.; Anal calcd. for C$_{24}$H$_{30}$N$_4$O$_2$·0.4-H$_2$O: C, 69.67; H, 7.50; N, 13.54 Found C, 69.49; H, 7.38; N, 13.37.

Preparation B

3-[4 {-(N-isopropyl, N-cyclohexyl)carboxamido}-2-methoxybenzyl-]imidazo[4,5-b]pyridines

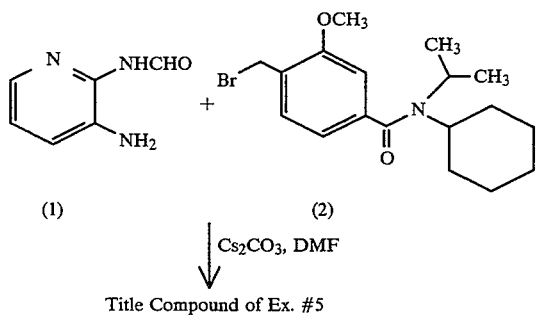

In accordance with General Scheme E and as shown in the specific scheme above, there is provided a regioselective method for making the 3H-regioisomer shown as the title compound. To a stirred solution of N-(3-amino-2-pyridinyl)formamide 1 (300 mg, 2.2 mmol) and 4-bromomethyl-3-methoxy-N-isopropyl, N-cyclohexyl benzamide 2 (803 mg, 2.2 mmol) in N,N-dimethylformamide (10 mL), cesium carbonate (1.58 g, 4.84 mmol) was added. The reaction mixture was stirred under argon at 25° C. After 20 hours, the reaction mixture was filtered and the residue washed with methylene chloride. The combined organic filtrates were concentrated to remove the solvent and then redissolved in methylene chloride. The organic solution was washed with brine, dried (MgSO$_4$), filtered and concentrated. The crude mixture (1.1 g) was chromatographed (silica gel, EtOAc/acetone 98/2) to give the title compound (430 mg, 48%).

EXAMPLE 6

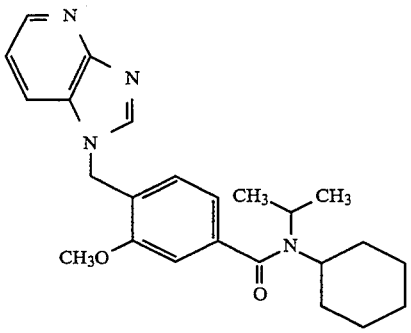

N-cyclohexyl-4-(1H-imidazo[4,5-b]pyridin-1-ylmethyl)-3-methoxy-N-(1-methylethyl)benzamide To a stirred solution of imidazo[4,5-b]pyridine (350 mg, 2.94 mmol) in N,N-dimethylformamide (25 mL), sodium hydride (120mg, 60% dispersion in mineral oil, 2.94 mmol) was added. After stirring for 2 hr, 4-bromomethyl-3-methoxy-N-isopropyl,N-cyclohexyl benzamide (1.07 g, 2.94 mmol) was added over 15 min. The reaction mixture was stirred under argon at 25° C. After 18 h, the reaction was quenched by adding acetic acid (0.5 mL) and the solvent was removed under reduced pressure at <45° C. The crude mixture (1.58 g) was chromatographed (silica gel, CH$_2$Cl$_2$-MeOH-NH$_4$OH 90-10-1) to give the title compound. (190 mg, 16%) mp 189°–91° C.; Anal calcd. for C$_{24}$H$_{30}$N$_4$O$_2$: C, 70.9; H, 7.44; N, 13.78. Found C, 70.5; H, 7.58; N, 13.58.

EXAMPLE 7

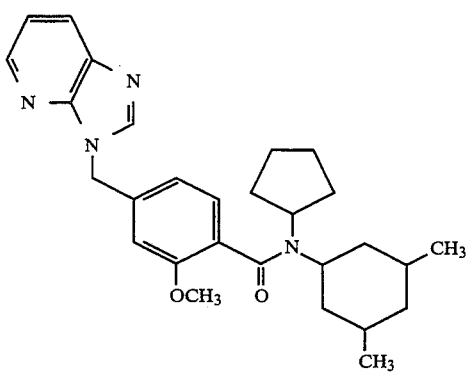

N-cyclopentyl-N-(3,5-dimethylcyclohexyl)-4-(3H-imidazo[4,5-b]pyridin-3-ylmethyl)-2-methoxybenzamide To a stirred solution of imidazo[4,5-b]pyridine (220 mg, 1.84 mmol) in N,N-dimethylformamide (20 mL), sodium hydride (74 mg, 60% dispersion in mineral oil, 1.85 mmol) was added. After stirring for 2 hr, 4-bromomethyl-2-methoxy-N-cyclopentyl, N-3,5-dimethylcyclohexyl benzamide (740 mg, 2.94 mmol) was added over 15 min. The reaction mixture was stirred under argon at 25° C. After 18 h, the reaction was quenched by adding acetic acid (1 mL) and the solvent was removed under reduced pressure at <45° C. The crude mixture (1.2 g) was chromatographed (silica gel, $CH_2Cl_2$-MeOH-$NH_4OH$ 95-5-0.5) to give the title compound. (398 mg, 47%) mp 80-82° C.; Anal calcd. for $C_{28}H_{36}N_4O_2 \cdot 0.4H_2O$: C, 71.89; H, 7.93; N, 11.98. Found C, 71.93; H, 7.90; N, 11.88.

EXAMPLE 8

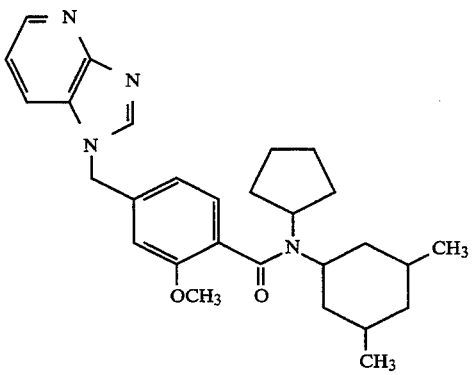

N-cyclopentyl-N-(3,5-dimethylcyclohexyl)-4-(1H-imidazo[4,5-b]pyridin-1-ylmethyl)-2-methoxybenzamide To a stirred solution of imidazo[4,5-b]pyridine (220 mg, 1.84 mmol) in N,N-dimethylformamide (20 mL), sodium hydride (74 mg, 60% dispersion in mineral oil, 1.85 mmol) was added. After stirring for 2 hr, 4-bromomethyl-2-methoxy-N-cyclopentyl,N-3,5-dimethylcyclohexyl benzamide (740 mg, 2.94 mmol) was added over 15 min. The reaction mixture was stirred under argon at 25° C. After 18 h, the reaction was quenched by adding acetic acid (1 mL) and the solvent was removed under reduced pressure at <45° C. The crude mixture (1.2 g) was chromatographed (silica gel, $CH_2Cl_2$-MeOH-$NH_4OH$ 95-5-0.5) to give the title compound. (166 mg, 20%) DSC 185° C.; Anal calcd. for $C_{28}H_{36}N_4O_2$: C, 73.01; H, 7.88; N, 12.16. Found C, 72.87; H, 7.99; N, 12.17.

EXAMPLE 9

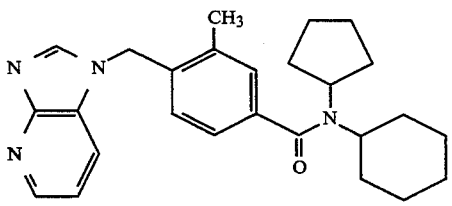

N-cyclohexyl-N-cyclopentyl-4-(1H-imidazo[4,5-b]pyridin-1-ylmethyl)-3-methylbenzamide Step (a): Preparation of 4-formyl-3-methylbenzoic acid N-cyclohexyl-N-cyclopentyl amide To a cold (−70° C.), stirred solution of 4-bromo-3-methylbenzoic acid N-cyclohexyl-N-cyclopentyl amide (4 g, 0.011 mol) in THF (40 mL) was added t-butyl lithium (13 mL of 1.7 M solution) via syringe over 10 min. The originally colorless solution became a dark red. Dimethylformamide (DMF) (884 mg) was added. The cold bath was removed and the reaction allowed to warm to 0°, during the course of which, the reaction became much lighter in color. The reaction was diluted with ethyl acetate, washed with 0.5 N $KHSO_4$ and the organic layer was dried ($Na_2SO_4$). The drying agent was filtered, the filtrate concentrated in vacuo and the crude product purified by chromatography on silica gel using mixtures of ethyl acetate and hexane as eluents to give title compound of Step(a), m.p. 57°-59° C. Anal. Calcd for $C_{20}H_{27}NO_2$: C, 76.64; H, 8.68; N, 4.47. Found: C, 76.21; H, 8.71; N, 4.11.

Step (b): Preparation of 4-hydroxymethyl-3-methylbenzoic acid N-cyclohexyl-N-cyclopentyl amide To a cold (0° C.), stirred solution of the aldehyde intermediate of Step(a) (2.8 g, 9 mmol) in methanol (60 mL) was added solid sodium borohydride (250 mg). The cold bath was removed and the reaction allowed to warm to room temperature. After 30 min., the reaction was poured onto water, extracted with ethyl acetate and the organic layers dried ($Na_2SO_4$). The drying agent was filtered, the filtrate concentrated in vacuo and the crude product chromatographed on silica gel using mixtures of ethyl acetate and hexane as eluents. The pure title compound of Step(b) was obtained as an oil. Anal. Calcd. for $C_{20}H_{29}NO_2$: C, 76.15; H, 9.27; N, 4.44. Found: C, 75.89; H, 9.45; N, 4.20.

Step (c): Preparation of 4-chloromethyl-3-methylbenzoic acid N-cyclohexyl-N-cyclopentyl amide A solution of alcohol intermediate of Step(b) (2.1 g, 6.6 mmol) in thionyl chloride (25 mL) was warmed to 45° for one hr. Excess thionyl chloride was removed in vacuo and the residue dissolved in ethyl acetate. The organic layer was washed with dilute aqueous $NaHCO_3$ solution and dried ($Na_2SO_4$). The drying agent was filtered, the filtrate concentrated in vacuo and the residue chromatographed on silica gel using mixtures of ethyl acetate and hexane as eluents. The pure title compound of Step(c), the "chloride intermediate", was obtained as a crystalline solid, m.p. 106–107°. Anal. Calcd for $C_{20}H_{28}ClNO$: C, 71.94; H, 8.45; N, 4.19; Cl, 10.62. Found: C, 72.22; H, 8.56; N, 4.13; Cl, 10.99.

Step (d): Preparation of N-cyclohexyl-N-cyclopentyl-4-(1H-imidazo[4,5-b]pyridin-1-ylmethyl)-3-methyl benzamide A slurry of cesium carbonate (1.1 g, 3.4 mmol) in a solution of 1(H)-imidazo[4,5-b]pyridine (360 mg, 3 mmol) in DMF (10 ml) was heated at 65° with stirring for 2 hr. The chloride intermediate of Step(c) (1 g, 3 mmol) was added and the reaction was heated for another 2 hrs. The reaction was worked up and the crude product purified by chromatography (silica gel, $CH_2Cl_2$-MeOH-$NH_4OH$ 95-5-0.5 ) to give the title compound (472 mg, 38%) which was obtained as a crystalline solid, m.p. 191°-192° C. Anal. Calc'd for $C_{26}H_{32}N_4O \cdot 0.75 H_2O$: C, 72.61; H, 7.85; N, 13.03. Found: C, 72.30; H, 7.61; N: 12.94.

EXAMPLE 10

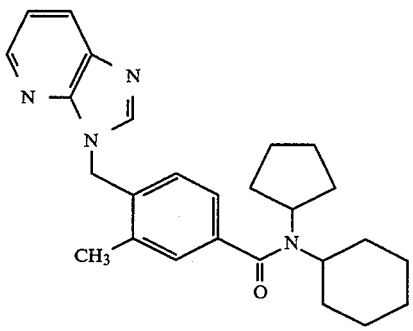

N-cyclohexyl-N-cyclopentyl-4-(3H-imidazo[4,5-b]pyridin-3-ylmethyl)-3-methylbenzamide A slurry of cesium carbonate (1.1 g, 3.4 mmol) in a solution of 1(H)-imidazo[4,5-b]pyridine (360 mg, 3 mmol) in DMF (10 ml) was heated at 65° with stirring for 2 hr. The chloride intermediate prepared in Step(c) of Example #9 (1 g, 3 mmol) was added and the reaction was heated for another 2 hrs. The reaction was worked up and the crude product purified by chromatography (silica gel, $CH_2Cl_2$-MeOH-$NH_4OH$/95-5-0.5) to give the title compound which was obtained as a crystalline solid, m.p. 181°–182° C. Anal. Calcd for $C_{26}H_{32}N_4 \cdot 0.25$ $H_2O$: C, 74.16; H 7.78; N, 13.31. Found: C, 74.34; H, 7.91; N: 13.04.

EXAMPLE 11

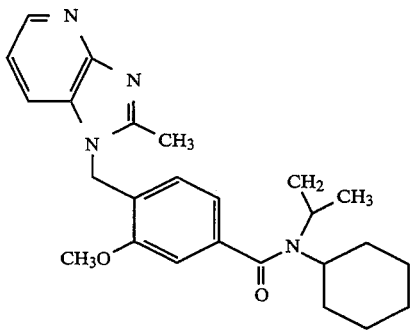

N-cyclohexyl-3-methoxy-N-(1-methylethyl)-4-[(2-methyl-1H-imidazo[4,5-b]pyridin-1-yl)methyl]benzamide 2-Methyl-1-(H)-imidazo[4,5-b]pyridine (1.3 g, 0.010 mol) was stirred with cesium carbonate (3.5 g) in DMF (20 ml) at 60° C. for 2 hours under an argon atmosphere. A solution of 4-bromomethyl-3-methoxy-N-isopropyl, N-cyclohexyl bezamide (3.72 g) in DMF (20 ml) was added and the reaction stirred at 60° C. for 2 hours. The insoluble material was filtered and the reaction concentrated in vacuo on a rotary evaporator using an oil pump. The residue was treated with ethyl acetate and water and the organic layer was dried ($Na_2SO_4$). The drying agent was filtered and the filtrate concentrated in vacuo. The residue was chromatographed on silica gel using mixtures of $CH_2Cl_2$, MeOH and ammonium hydroxide to give the title compound (715 mg, 17%) m.p. 201–203° C. $C_{25}H_{32}N_4O_2 \cdot 0.5H_2O$ Calc: C, 69.90; H, 7.74; N, 13.04. Found: C, 69.78; H, 7.49; N, 12.99.

EXAMPLE 12

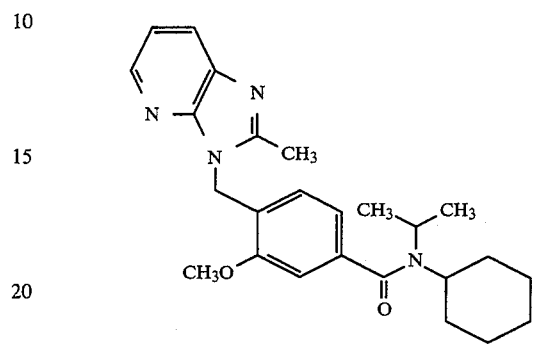

N-cyclohexyl-3-methoxy-N-(1-methylethyl)-4-[(2-methyl-3H-imidazo[4,5-b]pyridin-3-yl)methyl]benzamide 1.3 g (0.010 moles) of 2-methylimidazo-(4,5-b)pyridine was stirred with 3.5 g of $Cs_2CO_3$ in 20 mLs of DMF at 60° C. for 2 hours under argon. 4-Bromomethyl-3-methoxy-N-isopropyl,N-cyclohexyl benzamide (3.72 g, 10.2 mmol) was added at once in 20 mL of warm DMF and stirred at 60° C. for 2 more hours. The solvent was removed after filtration under high vacuum on a rotary evaporator. The residue was treated with ethyl acetate and water. The organic phase was dried over $Na_2SO_4$, filtered, and solvent removed. The residue was chromatographed by flash chromatography eluting with 96 $CH_2Cl_2$/4 MeOH/0.5 $H_2O$ to give the title compound (1.8 g, 35%) m.p. 210-212° C. $C_{25}H_{32}N_4O_2 \cdot 0.5H_2O$ Calc: C, 69.90; H, 7.74; N, 13.04. Found: C, 69.91; H, 7.51; N, 13.00.

EXAMPLE 13

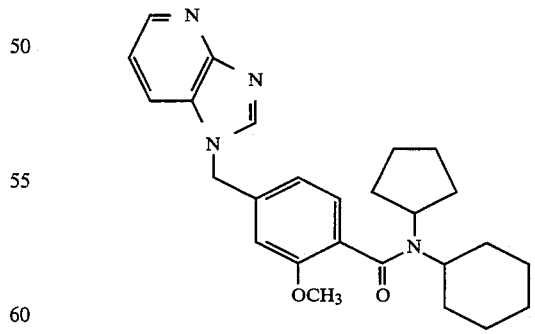

N-cyclohexyl-N-cyclopentyl-4-(1H-imidazo[4,5-b]pyridin-1-ylmethyl)-2-methoxybenzamide The compound of Example 13 was synthesized by the following procedures which refer to the scheme below.

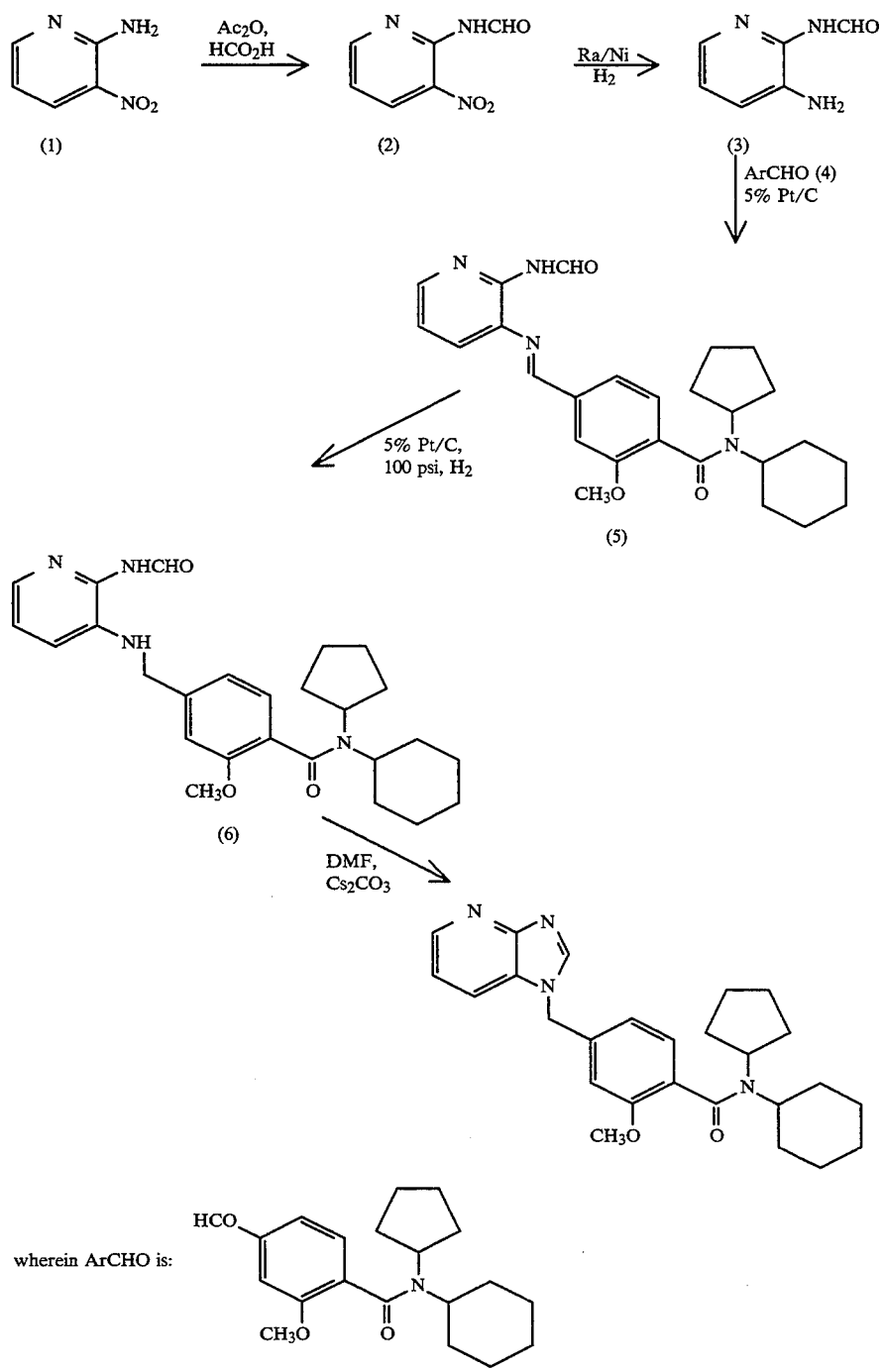

wherein ArCHO is:

Stem (a): Preparation of 2

A solution of acetic anhydride (102 ml) and formic acid (43 ml) were heated at 60° C. for 3 hrs. The reaction was cooled to 20° C. and 2-amino-3-nitropyridine (6.95 g, 0.05 mol) was added over 15 min. After stirring at room temperature for 72 hr, the solvents were removed under reduced pressure at <45° C. and the product obtained (8.5 g, 100%) was used in the next step without further purification. DSC (mp) 143° C.; Anal calcd. for $C_6H_5N_3O_3$: C, 43.12; H, 3.02; N, 25.14 Found C, 43.17; H, 2.99; N, 24.91.

Stem (b): Preparation of 3

To a solution of 2 (4.49 g, 0.027 mol) in distilled tetrahydrofuran (130 ml) in a parr bottle, Raney-nickel in methanol (6 ml) was added. The reaction mixture was flushed with nitrogen and hydrogen several times and then maintained under hydrogen at delivery pressure of 5 psi. After stirring at 20°-25° C. for approximately 4 hrs, the reaction was vented and purged with nitrogen. The contents of the reaction were filtered and concentrated to remove the solvent. The crude product (4.5 g) was chromatographed (silica gel, ethyl acetate/acetone 98/2) to give 3 (2.88 g, 78%). DSC (mp) 152° C.; Anal calcd. for $C_6H_7N_3O$: C, 52.55; H, 5.14; N, 30.64 Found C, 52.53; H, 5.18; N, 30.43.

Step (C): Preparation of 5

To a solution of 3 (167 mg, 1.22 mmol) and 4-formyl-3-methoxybenzoic acid N-cyclohexyl-N-cyclopentyl amide (4; 400 mg, 1.22 mmol) in distilled tetrahydrofuran (30 ml) in a Fisher-Porter bottle, dry 5% Pt on carbon (100 mg) was added. The reaction mixture was flushed with nitrogen and hydrogen several times and then maintained under hydrogen at delivery pressure of 5 psi. After stirring at 20°-25° C. for 20 hrs, more Pt on carbon (100 mg) was added and the reaction vessel was repressurized (5 psi, $H_2$). After additional 40 hrs, the reaction was vented and purged with nitrogen. The contents of the reaction were filtered and concentrated to remove the solvent. The crude liquid (470 mg) was chromatographed (silica gel, ethyl acetate/acetone 98/2) to give recovered aldehyde 4 (85 rag, 21%), title compound 5 (270 mg, 52%) and recovered amine 3 (60 mg, 35%). Title compound 5: $^1$H NMR (CDCl$_3$) 9.56 (d, J=11 Hz, 1H), 8.73 (d, J=11 Hz, 1H), 8.55 (s, 1H), 8.16 (d, J=5 Hz, 1H), 7.53 (d, J=3 Hz, 1H), 7.51 (d, J=8 Hz, 1H), 7.39 (d, J=7.5 Hz, 1H), 7.24 (dd, J=7.5, 3 Hz, 1H), 7.09 (dd, J=8, 5 Hz, 1H), 3.90, 3.91 (s, 3H), 3.74, 3.66 (p, J=8 Hz, 1H), 3.16, 2.93 (tt, J=12, 3 Hz, 1H), 2.68, 0.85 (complex band, 18H).

Step (d): Preparation of 6

To a solution of 5 (460 mg, 1.06 mmol) in distilled tetrahydrofuran (50 ml) in a Fisher-Porter flask, dry 5% Pt on carbon (250 mg) was added. The reaction mixture was flushed with nitrogen & hydrogen several times and then maintained at delivery pressure of 100 psi. After stirring at 20°-25° C. for 28 hrs, the reaction was vented and purged with nitrogen. The contents of the reaction were filtered and concentrated to remove the solvent. The crude liquid (460 mg) was chromatographed (silica gel, ethyl acetate/acetone 98/2) to give 6 (250 mg, 54%). $^1$H NMR (CDCl$_3$) 9.84, 9.80 (broad d, J=10 Hz, 1H), 9.47, 9.30 (d, J=10 Hz, 1H), 7.70, 7.66 (broad d, J=5 Hz, 1H), 7.10, 7.07 (d, J=7 Hz, 1H), 7.03-6.7 (complex band, 4H), 5.62, 5.38 (broad s, 1H), 4.33, 4.27 (broad m, 2H), 3.78, 3.62 (p, J=8 Hz, 1H), 3.70 (s, 3H), 3.16, 2.91 (tt, J=12, 3 Hz, 1H), 2.68, 0.85 (complex band, 18H).

Step (e): Preparation of title compound

To a solution of 6 (250 mg, 0.55 mmol) in dimethylformamide (10 ml), cesium carbonate (100 mg, 0.3 mmol) was added. The mixture was heated at 70° C. under argon. After 18 hr, the solvent was removed and the crude chromatographed (silica gel; CH$_2$Cl$_2$/MeOH/NH$_4$OH 93/7/0.7) to give pure of title compound (170 mg, 75%). mp 189°-91° C. (shrinks) and melts at 198°-200° C.; Anal calcd. for C$_{26}$H$_{32}$N$_4$O$_2$: C, 72.19; H, 7.46; N, 12.95 Found C, 71.89; H, 7.67; N, 12.78.

EXAMPLE 14

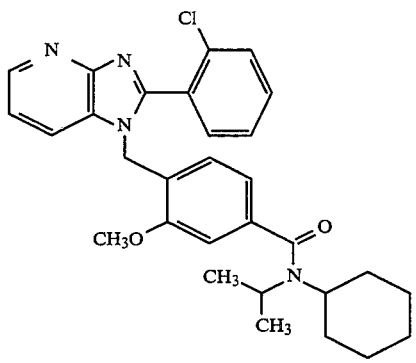

4-[[2-(2-chlorophenyl)-1H-midazo[4,5-b]pyridin-lyl-]methyl]-N-cyclohexyl-3-methoxy-N-(1-methylehyl)benzamide 2-2-Chlorophenyl)-1-(H)-imidazo[4,5-b]pyridine (1.3 g, 5.6 mmol) was added portionwise to a stirred slurry of NaH (prepared by washing 250 mg or 6.25 mmol of a 60% dispersion in silicone oil) in dimethylacetamide (15 mL) under a nitrogen atmosphere. After stirring for one hour at room temperature, 4-bromomethyl-3-methoxybenzoic acid N-isopropl-N-cyclohexylamide (2.1 g) was added in portions over 15 min. and the reaction was stirred at room temperature overnight. The reaction solvent was removed in vacuo using an oil pump. The residue was treated with EtOAc and water, the layers separated, and the organic layer washed with water and dried (Na$_2$SO$_4$). The drying agent was filtered, the filtrate stripped in vacuo and the residue chromatographed on silica gel using mixtures of CH$_2$Cl$_2$, MeOH and NH$_4$OH to give the pure title compound as a crystalline solid: m.p. 121°-123°. $^1$H NMR (300 MHz, CD$_3$OD, ppm): 3.80 ppm (s, 3H, OMe); 5.60 (s, 2H, benzylic CH$_2$); 6.95 (d, 1H, J=8 Hz, H6 of phenyl ring); 7.05 (d, 1H, J=8 Hz, H5 of phenyl ring); 7.30 (dd, 1H, J=5 Hz, H6 of pyridine); 7.55-7.70 (m, 4H, all protons on chlorophenyl); 7.90 (d, 1H, J=5 Hz, H5 on pyridine). Anal. Calcd for C$_{30}$H$_{33}$N$_4$O$_2$Cl.0.25 H$_2$O: C, 69.09; H, 6.47; N, 10.74; Cl, 6.80. Found: C, 68.80; H, 6.45; N, 11.06; Cl, 6.79.

EXAMPLE 15

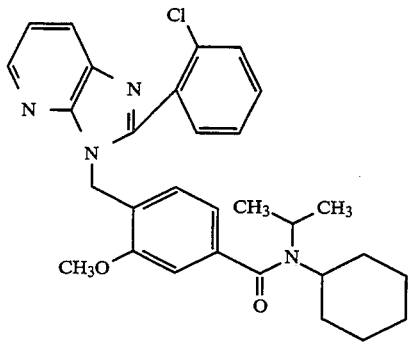

4-[[2-(2-chlorophenyl)-3H-imidazo[4,5-b]pyridin-3yl]methyl]-N-cyclohexyl-3-methoxy-N-(1-methylethyl)benzamide 2-(2-Chlorophenyl)-1(H)-imidazo[4,5-b]pyridine (1.3 g, 5.6 mmol) was added portionwise to a stirred slurry of NaH (prepared by washing 250 mg or 6.25 mmol of a 60% dispersion on silicone oil) in dimethylacetamide (15 mL) under a nitrogen atmosphere. After stirring for one hour at room temperature, 4-bromomethyl-3methoxybenzoic acid N-isopropyl-N-cyclohexylamide (2.1 g,) was added in portions over 15 min. and the reaction was stirred at room temperature overnight. The reaction solvent was removed in vacuo using an oil pump. The residue was treated with EtOAc and water, the layers separated, and the organic layer washed with water and dried (Na$_2$SO$_4$). The drying agent was filtered, the filtrate stripped in vacuo and the residue chromatographed on silica gel using mixtures of CH$_2$Cl$_2$, MeOH and NH$_4$OH to give the pure title compound as a crystalline solid: m.p. 121°-123°. $^1$H NMR (300 MHz, CD$_3$OD, ppm): 3.80 ppm (s, 3H, OMe); 5.60 (s, 2H, benzylic CH$_2$); 6.95 (d, 1H, J=8 Hz, H6 of phenyl ring); 7.05 (d, 1H, J=8 Hz, H5 of phenyl ring);

7.30 (dd, 1H, J=5 Hz, H6 of pyridine); 7.55-7.70 (m, 4H, all protons on chlorophenyl); 7.90 (d, 1H, J=5 Hz, H5 on pyridine). Anal. Calcd for $C_{30}H_{33}N_4O_2Cl.0.25 H_2O$: C, 69.09; H, 6.47; N, 10.74; Cl, 6.80. Found: C, 68.80; H, 6.45; N, 11.06; Cl, 6.79.

EXAMPLE 16

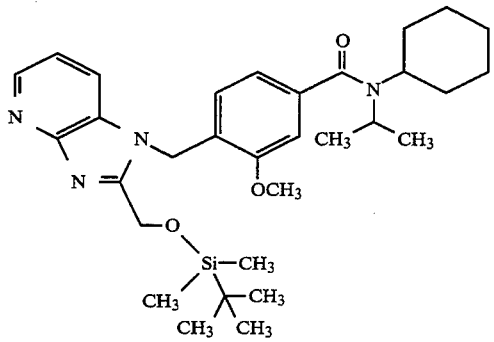

N-cyclohexyl-4-[[2-[[[(1,1-dimethyethyl)dimethylsilyl-]oxy]methyl]-1H-imidazo[4,5-b]pyridin-1-yl]methyl]-3-methoxy-N-(1-methylethyl)benzamide Step (a): Preparation of silyl ether intermediate A solution of 2-hydroxymethyl-1(H)-imidazo[4,5-b]pyridine (1.0 g, 6.7 mmol ), tert. -butyldimethylsilyl chloride (1.1 g, 7.3 mmol) and imidazole (460 mg, 6.76 mmol) in dimethylformamide (10 mL) was stirred for 3 hr. at room temperature under an argon atmosphere. The reaction solvent was removed in vacuo using an oil pump. Dilute ammonium hydroxide was added to the residue and the resulting solid was filtered and air dried to give the pure title compound: m.p. 155°-156°. $^1H$ NMR (300 MHz, $CD_3OD$, ppm): 0.15 (s, 6H, $CH_3$); 0.95 (s, 9H, $(CH_3)_3$); 5.00 (s, 2H, benzylic); 7.30 (dd, 1H, J=5 Hz, H6 of pyridine); 8.00 (d, 1H, J=5 Hz, H7 of pyridine); 8.35 (d, 1H, J=5 Hz, H5 of pyridine). Anal. Calcd. for $C_{13}H_{21}N_3OSi$: C, 59.28; H, 8.04; N, 15.95. Found: C, 59.11; H, 8.25; N, 15.72.

Step (b): Preparation of title compound

The silyl ether synthesized in Step (a), above, (1.75 g, 6.0 mmol) was added portionwise to a stirred slurry of NaH (prepared by washing 250 mg or 6.25 mmol of a 60% dispersion in silicone oil) in dimethylacetamide (15 mL) under a nitrogen atmosphere. After stirring for 15 min. at room temperature, 4-bromomethyl-3-methoxybenzoic acid N-isopropyl-N-cyclohexylamide (2.2 g) was added and the reaction stirred at room temperature overnight. The solvent was removed in vacuo using an oil pump and the residue treated with methylene chloride and dilute NH4OH. The layers were separated and the aqueous was extracted with methylene chloride. The combined organic layers were dried ($Na_2SO_4$), filtered and the filtrate concentrated in vacuo to give the crude product. Pure title compound was obtained by chromatography of the crude product on silica gel using mixtures of EtOAc, MeOH and NH4OH, m.p. 133°-135°. $^1H$ NMR (300 MHz, CDCl3, ppm): 0.15 ppm (s, 6H, dimethylsilyl); 0.85 (s, 9H, t-butyl); 3.85 (s, 3H, OMe); 5.00 (s, 2H, OCH2); 5.50 (s, 2H, CH2Ph); 6.62 and 6.68 (d, 1H each, J=8 Hz, H4 and H5 on phenyl); 6.85 (s, 1H, H3 on phenyl); 7.10, (dd, 1H, J=5 Hz, H6 on pyridine); 7.5 (d, 1H, J=5 Hz, H7 pyridine). Anal.

Calcd. for $C_{31}H_{46}N_4O_3Si.0.5H_2O$: C, 66.51; H, 8.46; N, 10.01. Found: C, 66.59; H, 8.35; N, 10.00.

EXAMPLE 17

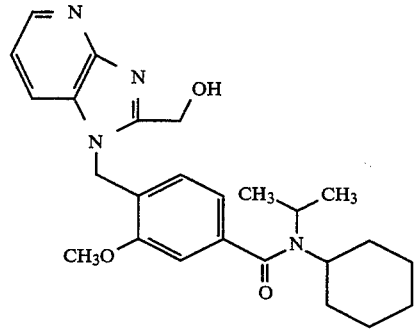

N-cyclohexyl-4-[[2-(hydroxymethyl)-1H-imidazo[4,5-b]pyridin-1-yl]methyl]-3-methoxy-N-(1-methylethyl)benzamide A solution of the silyl ether compound of Example #16 (1.0 g, 1.8 mmol) in tetrahydrofuran (THF) (10 mL) was treated with a solution of tetra-n-butyl ammonium fluoride (3.6 mL of a 1M solution in THF) with stirring for 3 hrs at room temperature. The reaction mixture was poured onto 15 mL of saturated aqueous NaHCO3 solution and extracted twice with $CH_2Cl_2$. The combined organic layers were dried ($Na_2SO_4$), filtered and the filtrate concentrated in vacuo to give the crude product. Purification was effected by chromatography on silica gel using mixtures of EtOAc, MeOH and NH4OH. The purified product was a crystlline solid, m.p. 117°-119°. The NMR (300 MHz, CDCl3) is identical with the silyl ether except the $CH_2O$ singlet is shifted to 5.10 ppm and signals associated with the silyl ether are absent. Anal. Calcd for $C_{25}H_{32}N_4O_3.0.75H_2O$: C, 66.72; H, 7.50; N, 12.45. Found: C, 66.78; H, 7.64; N, 12.35.

EXAMPLE 18

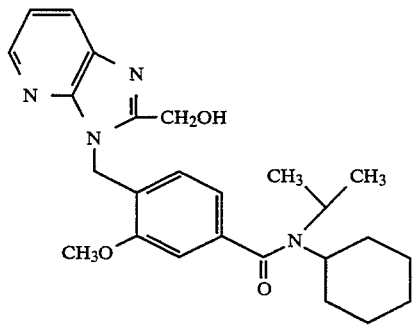

N-cyclohexyl-4-[[2-(hydroxymethyl)-3H-imidazo[4,5-b]pyridin-3-yl]methyl]-3-methoxy-N-(1-methylethyl)benzamide A solution of the silyl ether compound of Example #16 (1.0 g, 1.8 mmol) in THF (10 mL) was treated with a solution of tetra-n-butyl ammonium fluoride (3.6 mL of a 1M solution in THF) with stirring for 3 hrs at room temperature. The reaction mixture was poured onto 15 mL of saturated aqueous NaHCO3 solution and extracted twice with $CH_2Cl_2$. The combined organic layers were dried (Na2SO4), filtered and the filtrate concentrated in vacuo to give the crude product. Purification was effected by chromatography on silica gel using mixtures of EtOAc, MeOH and NH4OH. The purified product was a crystlline solid, m.p. 124°–126° C. Anal. Calcd for C25 H32N4O3.0.5H2O: C, 67.39; H, 7.47; N, 12.57. Found: C, 67.44; H, 7.67; N, 12.36.

EXAMPLE 19

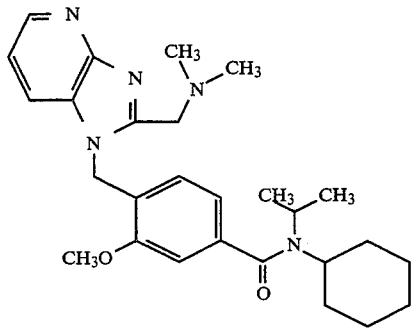

N-cyclohexyl-4-[[2-[(dimethylamino)methyl]-1H-imidazo[4,5-b]pyridin-1-yl]methyl]-3-methoxy-N-(1-methylethyl)benzamide 2-Dimethylaminomethyl-1(H)-imidazo[4,5-b]pyridine was synthesized by procedures analogous to those described in J. Het. Chem., 6, 759–760 (1969) for the synthesis of the di-n-butyl compound. A slurry of cesium carbonate (1.02 g, 3.12 mmol) in a solution of 2-dimethylamino-1(H)-imidazo[4,5-b]pyridine (0.5 g, 2.84 mmol) in dimethylformamide (15 mL) was stirred at 80° for 1 hr. 3-Methoxy-4-bromomethyl-N,N-isopropyl cyclohexyl benzamide was added and the reaction was continued at 80 for 3 hr. The reaction was filtered and the DMF was removed in vacuo using an oil pump. The resulting brown oil was purified first, by chromatography on .silica gel using mixtures of CH2Cl2, MeOH and NH4OH and then recrystallization from Et2O and hexane: m.p. 141°–142°. 1H NMR (CDCl3, ppm): 2.3 (s, 6H); 3.75 (s, 2H); 3.85 (s, 3H); 5.6 (s, 2H); 6.68–6.78 (m, 2H); 6.88 (d, J=2 Hz, 1H); 7.1 (dd, J=7.5 and 5 Hz, 1H); 7.55 (dd, J=7.5 and 2 Hz, 1H); 8.53 (dd, J=5 and 2 Hz, 1H). Anal. Calcd. for C27H37N5O2: C, 69.95; H, 8.04; N, 15.11. Found: C, 70.00; H, 8.26; N, 15.00.

EXAMPLE 20

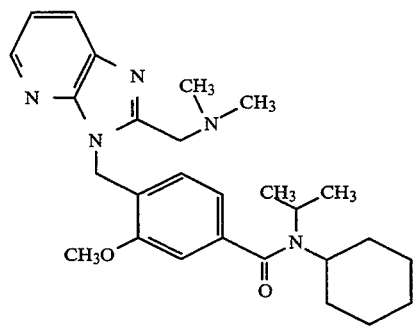

N-cyclohexyl-4-[[2-[(dimethylamino)methyl]-3H-imidazo[4,5-b]pyridin-3-yl]methyl]-3-methoxy-N-(1-methylethyl)-benzamide 2-Dimethylaminomethyl-1(H)-imidazo[4,5-b]pyridine was synthesized by procedures analogous to those described in J. Het. Chem., 6, 759–760 (1969) for the synthesis of the di-n-butyl compound. A slurry of cesium carbonate (1.02 g, 3.12 mmol) in a solution of 2-dimethylamino-1(H)-imidazo[4,5-b]pyridine (0.5 g, 2.84 mmol) in dimethylformamide (15 mL) was stirred at 80° for 1 hr. 3-Methoxy-4-bromomethyl-N,N-isopropyl cyclohexyl benzamide was added and the reaction was continued at 80 for 3 hr. The reaction was filtered and the DMF was removed in vacuo using an oil pump. The resulting brown oil was purified first, by chromatography on silica gel using mixtures of CH2Cl2, MeOH and NH4OH and then recrystallization from Et20 and hexane: m.p. 124°–125°. Anal. Calcd. for C27H37N5O2.0.5H2O: C, 68.62; H, 8.10; N, 14.82. Found: C, 68.70; H, 7.72; N, 14.40.

EXAMPLE 21

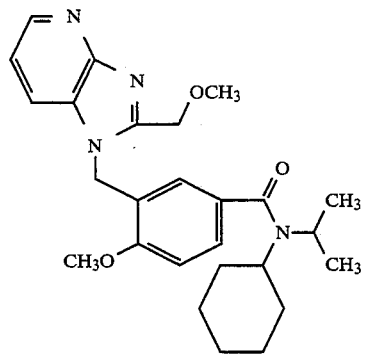

N-cyclohexyl-3-methoxy-4-[[2-(methoxymethyl)-1H-imidazo[4,5-b]pyridin-1-yl]methyl]-N-(1-methylethyl)benzamide Step (a): Preparation of 2-methoxymethyl-1(H)imidazo[4,5-b]pyridine)

Crude 2-chloromethyl-1(H)-imidazo[4,5-b]pyridine (3 g) [synthesis described in J. Het. Chem., 6, 759–760 (1969)](contaminated with 2-hydroxymethyl-1(H)-imidazo[4,5-b]pyridine) was added to a 25% solution of sodium methoxide in methanol (16.8 mL) and the reaction was refluxed with stirring for 8 hr. The reaction was concentrated and the crude product was chromatographed on silica gel using mixtures of CH2Cl2, MeOH, and NH4OH as eluents to give the desired product as a crystalline solid, m.p. 117°–118°. 1H NMR (CDCl3, ppm): 3.5 (3H, s); 4.73 (2H, s); 4.88 (1H, s); 7.30 (1H, dd, J =7.5 and 5 Hz); 7.98 (1H, dd, J=7.5 and 2 Hz); 8.34 (1H, dd, J=5 and 2 Hz ). Anal. Calcd. for C8H9N3O: C, 58.88; H, 5.56; N, 25.75. Found: C, 59.16; H, 5.94; N, 25.31.

Step (b): Preparation of title compound

The imidazopyridine synthesized in Step (a), above, (0.57 g, 3.49 mmol) was added to a stirred slurry of NaH (0.21 g of a 60% dispersion in silicone oil) in DMF (5 mL) at 0°. After warming to room temperature and stirring for 5 hr., the reaction was cooled to 0° and 3-methoxy-4-bromomethyl-N,N-isopropyl cyclohexyl benzamide (1.54 g, 4.19 mmol) was added. The reaction was stirred at room temperature overnight. The reaction was quenched with 1N HCl and DMF removed in vacuo using an oil pump. The residue was dissolved in EtOAc, washed with aqueous NaHCO3, water and dried (Na2SO4). The drying agent was filtered and the filtrate concentrated in vacuo to give a brown oil that was purified by chromatography on silica gel using mixtures of CH2Cl2, MeOH, and NH4OH as eluents. The purified product was a crystalline solid, m.p. 123°–124°. $^1$H NMR (CDCl3, ppm): 3.4 (3H, s); 3.84 (3H, s); 4.8 (2H, s); 5.5 (2H, s); 6.75 (2H, s); 6.8? (1H, s); 7.15 (1H, dd, J=7 and 5 Hz); 7.58 (1H, dd, J=7 and 2 Hz); 8.56 (1H, dd, J=5 and 2 Hz). Anal. Calcd. for C26H34N4O3: C, 69.31; H, 7.61; N, 12.43. Found: C, 69.28; H, 7.60; N, 12.41.

EXAMPLE 22

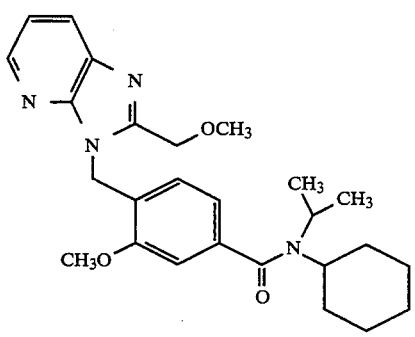

N-cyclohexyl-3-methoxy-4-[[2-(methoxymethyl)-3H-imidazo[4,5-b]pyridin-3-yl]methyl]-N-(1-methylethyl)-benzamide The imidazopyridine synthesized in Step (a) of Example #21, above, (0.57 g, 3.49 mmol) was added to a stirred slurry of NaH (0.21 g of a 60% dispersion on silicone oil) in DMF (5 mL) at 0°. After warming to room temperature and stirring for 5 hr., the reaction was cooled to 0° and 3-methoxy-4-bromomethyl-N,N-isopropyl cyclohexyl benzamide (1.54 g, 4.19 mmol) was added. The reaction was stirred at room temperature overnight. The reaction was quenched with 1N HCl and DMF removed in vacuo using an oil pump. The residue was dissolved in EtOAc, washed with aqueous NaHCO3, water and dried (Na2SO4). The drying agent was filtered and the filtrate concentrated in vacuo to give a brown oil that was purified by chromatography on silica gel using mixtures of CH2Cl2, MeOH, and NH4OH as eluents. The purified product was a crystalline solid, m.p. 126° C. Anal. Calcd. for C26H34N4O3: C, 69.31; H, 7.61; N, 12.43. Found: C, 69.03; H, 7.71; N, 12.35.

EXAMPLE 23

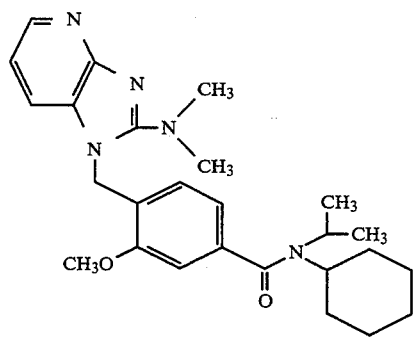

N-cyclohexyl-4-[[2-(dimethylamino)-1H-imidazo[4,5-b]pyridin-1-yl]methyl]-3-methoxy-N-(1-methylethyl)-benzamide The compound of Example #23 was synthesized by the following procedures which refer to the scheme depicted below:

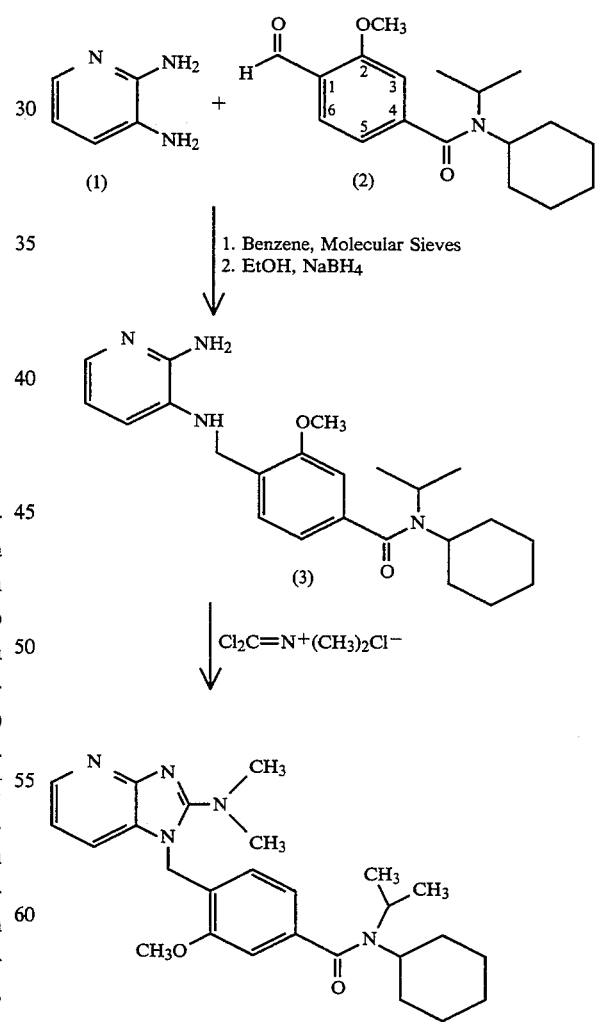

Step (a): Preparation of N-cyclohexyl-3-methoxy-4-[((2-amino-3-pyridinyl)amino)methyl]-N-(1methylethyl)benzamide To a suspension of 2,3-diaminopyridine 1 (550 mg, 5 mmol) in dry tetrahydrofuran (200 ml), dried molecular sieves (5 g, 4A°) and the substituted benzaldehyde 2 (1.82 g, 6 mmol) were added. After refluxing for 4 hours, the mixture was cooled to room temperature and stirred for 18 hours. The reaction was filtered and the residue washed with more ether (200 ml). The combined organic filtrates were concentrated and dried under vaccuum. The crude dried product (1.4 g) was dissolved in ethanol (200 ml) and treated with sodium borohydride (1.4 g). After refluxing for 20 hours, the reaction mixture was cooled to room temperature and quenched with water (200 ml). The aqueous solution was extracted with methylene chloride (2×300), dried (MgSO$_4$) and concentrated. The crude product (1.18 g) was chromatographed (silica gel, methylene chloride/methanol/ammonium hydroxide 90/10/1) to give the intermediate 3 (598 mg, 30%) as white solid; Anal calcd. for $C_{23}H_{32}N_4O_2 \cdot 0.75H_2O$: C, 67.37; H, 8.37; N, 13.66 Found C, 67.20; H, 8.03; N, 13.57.

Step (b): Preparation of Title Compound:

Phosgene dimethyliminium chloride (0.103 g, 0.64 mmol) was added to a stirred suspension of the substituted pyridine 3 (0.194 g, 0.489 mmol) prepared in Step (a), above, in $CH_2Cl_2$ (10 mL). After stirring the reaction at room temperature for 48 hrs, it was quenched with ammonium hydroxide and the solvent removed in vacuo. The residue was chromatographed on silica gel using mixtures of $CH_2Cl_2$, MeOH, and $NH_4OH$ as eluents to give the product as an oil that crystallized on treatment with ether, m.p. (DSC) 166.27° C. $^1$H NMR (CDCl$_3$,ppm); 3.02 (6H, s); 3.92 (3H, s); 5.18 (2H, s); 6.76-6.85 (2H, m); 6.88-6.95 (2H, m); 7.17 (1H, dd, J=7 and 2 Hz); 8.33 (1H, dd, J=5 and 2 Hz). Anal. Calcd. for $C_{26}H_{35}N_5O_2$: C, 68.91; H, 7.78; N, 15.45. Found: C, 68.97; H, 7.81; N, 15.22.

BIOLOGICAL EVALUATION

Assay A: Human Platelet Receptor Binding

Compounds of the invention were evaluated for their ability to inhibit specific binding of [$^3$H]PAF to human platelet membrane preparation. Human packed platelets were obtained from Lifesource, Inc. (Glenview, Ill.) and washed 3 times with 10 mM Trizma pH 7.0, 2 mM EDTA (dipotassium salt), 150 mM KCL and then once with 10 mM Trizma 7.4, 20 mM CaCL$_2$. The platelets were broken by freezing in a dry ice-ethanol bath, followed by thawing in 24° C. water baths. The preparation was centrifugation (40,000 x g, 20 minutes, 4° C.) and the pellet resuspended in 10 mM Trizma 7.4, 20 mM CaCL$_2$, 5 mg/ml human albumin. Protein concentration in the platelet membrane preparation was determined by the Lowry method [ref]. Aliquots of the membrane preparation were stored at −70° C. Each preparation was characterized for PAF receptor number and dissociation constant (Kd). In binding assays 5 μl of test compound, solubilzed in DMSO, was added to polypropylene tubes along with 0.75 nM [$^3$H]PAF and 200 mcl [0.075 nM] of membranes and 95 μl 10 mM Trizma 7.4, 20 mM CaCL$_2$, 5 mg/ml human albumin. Tubes were incubated for 30 minutes at 24° C. The incubation was terminated by adding 4 ml of ice-cold 10 mM Trizma DH 7.4, 20 mM CaCL$_2$ and 20 mg/ml BSA prior to vacuum filtration using Whatman GF/C filters. Filters were prepared and counted for a scintillation counter. All DPM values were corrected for background and isotope decay. Triplicate determinations for single doses were averaged. The amount of non-specific binding was subtracted from all dose averages, giving an amount of specific binding in all cases. The IC$_{50}$ values for compounds of the invention determined by the Allfit program using percent displacement data. Allfit is a 'basic' computer program for simultaneous curve fitting of a family of signoidal dose-response curves using the four parameter logistic equation. Results are shown in Table I.

Assay B: Human Platelet Aggregation Inhibition

Compounds of the invention were evaluated for their ability to inhibit PAF-induced aggregation of human platelets in a human-platelet-rich plasma. Venous blood was collected from donors who fasted for 8 hours and were instructed not to use antiinflammatory drugs for 2 weeks prior to blood draw. Blood was collected into syringes containing 0.1 ml of 3.8% [w/v] citrate and centrifuged in polypropylene tubes at 150xg for 20 minutes at room temperature. The platelet rich plasma [PRP] was collected and let sit for 20 minutes at room temperature. Platelet activating factor [PAF] was diluted in 0.9% NaCl with 0.25% bovine serum albumin. Silicon treated cuvettes with stir bars were placed in the 37° heating block of the platelet aggregometer [Bio-Data Corporation, Platelet Aggregation Profiler, Model PAP-4]. PRP and test compound were added to cuvettes and aggregation monitored for 10-15 seconds at 37° with stirring. PAF was added and aggregation monitored for an additional 3 minutes. Peak aggregation was considered the peak of the first aggregation wave usually 45-60 seconds after PAF addition. Inhibition of aggregation was determined by the following: 1−[(% aggregation in the presence of compound)÷(% maximal aggregation)]. A log/logit transformation was used to determine half maximal inhibitory concentration of a test compound [IC$_{50}$]. Results are shown in Table I.

Assay C: Human Neutrophil Receptor Binding

Compounds of the invention were evaluated for their ability to inhibit PAF-induced specific binding of [$^3$H]PAF to receptors on human neutrophil membrane. Human neutrophils were isolated from venous blood by dextran sedimentation followed by density gradient centrifugation using Ficoll-Hypaque [J. Biol. Chem., 254:7865-7869, 1979]. Residual red blood cells were removed by hypotonic lysis. Neutrophils were suspended in 50 mM Tris-HCl buffer, pH 7.7, and cells disrupted by sonication for 15 seconds on ice. Unbroken cells and nuclei were removed by slow speed centrifugation [1000xg, 10 min. 4°]. The resultant supernatant was centrifuged at 100,000xg for 60 minutes at 4°. The pellet was suspended in 10 mM Tris-HCl, pH 7.4, with 10 mM MgCl$_2$. Protein content was determined by the method of Lowry [J. Biol. Chem., 193:265-275, 1951]. Membranes were characterized for the concentration of binding sites [Bmax] and affinity for the ligand [Kd] using [$^3$H]PAF by Scatchard analysis. Binding assays were conducted by incubating 50 mcg of membranes with 0.9 nM [$^3$H]PAF and test compounds in 10 mM Tris-HCl buffer, pH 7.4, containing 0.1% bovine serum albumin. Nonspecific binding was determined by the addition of 1 μM PAF. Binding assay were done for 30 minutes at 24°. The assay was terminated by filtration-through a Whatman GF/C glass filters and radioactivity determined by liquid scintillation counting. Results are shown in Table I.

TABLE I

Evaluation of PAF Antagonist Activity of Compounds of the Invention

| Example # | Assay A[1] IC$_{50}$ (nM) | Assay B[2] IC$_{50}$ (nM) | Assay C[3] IC$_{50}$ (nM) |
|---|---|---|---|
| 1 | 1031 | — | — |
| 2 | 78 | 227 | — |
| 3 | 2 | 7 | 0.5 |
| 4 | 150 | — | — |
| 5 | 420 | — | — |
| 6 | 6 | 113 | 8 |
| 7 | 73 | — | — |
| 8 | 35 | 7 | 23 |
| 9 | 479 | — | — |
| 10 | 5240 | — | — |
| 11 | 9 | — | — |
| 12 | 1161 | — | — |
| 13 | 206 | — | — |
| 14 | 395 | — | — |
| 15 | 574 | — | — |
| 16 | 51 | — | — |
| 17 | 6 | — | — |
| 18 | 11 | — | — |
| 19 | 3 | — | — |
| 20 | 10* | — | — |
| 21 | 9 | — | — |
| 22 | 88 | — | — |
| 23 | 13 | — | — |

[1] Assay A: Human Platelet Receptor Binding
[2] Assay B: Human Platelet Aggregation Inhibition
[3] Assay C: Human Neutrophil Receptor Binding
*Ex. #20 compound showed 62% inhibition at 10 nM, based on a two-run average.

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient in a range from about 1 to about 1000 mg, preferably from about 1 to about 500 mg, and more preferably from about 10 to about 100 mg. A suitable daily dose for a mammal may vary widely depending on the condition of the patient and other factors. However, a dose in a range from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is in a range from about 0.1 to 100 mg/kg body weight injected per day in multiple doses depending on the disease being treated. A preferred daily dose would be from about 1 to 50 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These subdoses may be administered in unit dosage forms. Typically, a dose or sub-dose may contain from about 1 mg to about 1000 mg of active compound per unit dosage form. A more preferred dosage will contain from about 2 mg to about 500 mg of active compound per unit dosage form. Most preferred is a dosage form containing from about 3 mg to about 400 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I:

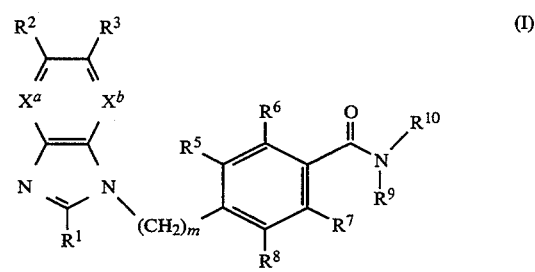

wherein each of $X^a$ and $X^b$ is independently selected from nitrogen atom and $>CR^4$, with the proviso that when one of $X^a$ and $X^b$ is selected as nitrogen atom then the other of $X^a$ and $X^b$ must be selected from $>CR^4$ and with the further proviso that one of $X^a$ and $X^b$ must be a nitrogen atom; wherein m is a number selected from one through six, inclusive; wherein $R^1$ is selected from hydrido, alkyl, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyloxyalkyl, aryl/alkylsilyloxyalkyl, arylsilyloxyalkyl, mercaptoalkyl, alkoxycarbonyloxy, alkylthio, alkylthioalkyl, alkylsulfinylalkyl, alkylsulfonylalkyl, cycloalkylthio, cycloalkylalkylthio, alkylcarbonylthio, arylthio, arylcarbonylthio, aralkylthio and aralkylcarbonylthio;

wherein each of $R^2$, $R^3$ and $R^4$ is independently selected from hydrido, alkyl, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, alkoxyalkyl, alkylcarbonyl, alkylcarbonylalkyl, alkylsilyloxyalkyl, alkoxycarbonyl, cyano, nitro, alkylthio, alkylthioalkyl, alkylsulfinylalkyl, alkylsulfonylalkyl, cycloalkylthio and cycloalkylalkylthio;

wherein each of $R^5$, $R^6$, $R^7$ and $R^8$ is independently selected from hydrido, alkyl, hydroxy, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyloxyalkyl, alkoxycarbonyloxy, alkylthio, alkylthioalkyl, alkylsulfinylalkyl, alkylsulfonylalkyl, cycloalkylthio, cycloalkylalkylthio, alkylcarbonylthio, arylthio, arylcarbonylthio, aralkylthio and aralkylcarbonylthio, with the proviso that at least one of $R^5$, $R^6$, $R^7$ and $R^8$ must be a group other than hydrido;

wherein each of $R^1$, $R^2$, $R^3$, $R^4$, $R^5$, $R^6$, $R^7$ and $R^8$ may be further independently selected from amino and amido radicals of the formulae

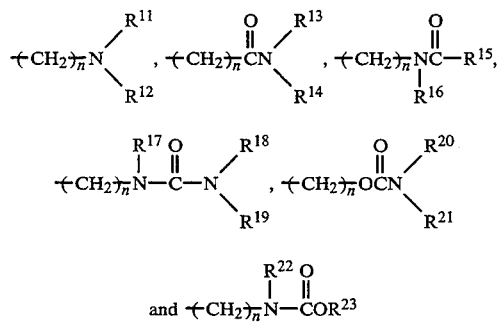

wherein each n is a number independently selected from zero to six, inclusive; wherein each of $R^{11}$ through $R^{23}$ is independently selected from hydrido, alkyl, cycloalkyl, hydroxyalkyl, cycloalkylalkyl, alkoxyalkyl, aralkyl and aryl;

wherein each of $R^9$ and $R^{10}$ is independently selected from hydrido, alkyl, haloalkyl, cycloalkyl, polycycloalkyl, polycycloalkylalkyl, cycloalkylalkyl, aralkyl, aryl, alkenyl and cycloalkenyl; wherein any of said $R^9$ and $R^{10}$ groups may be substituted at one or more substitutable positions by one or more groups selected from alkyl, halo, haloalkyl and alkoxy; or a pharmaceutically-acceptable salt thereof.

2. Compound of claim 1 of Formula IA or Formula IB:

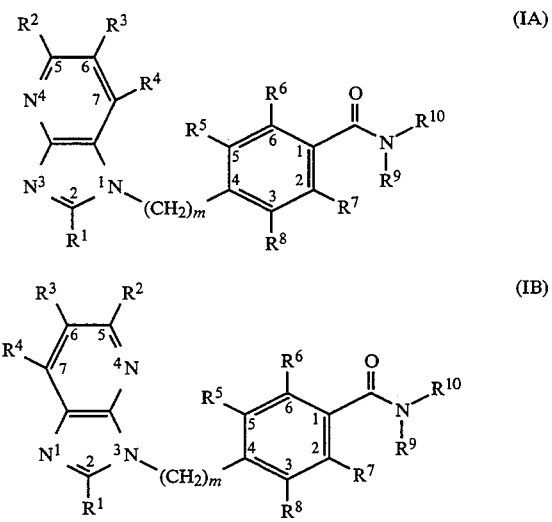

wherein m is a number selected from one through five, inclusive; wherein $R^1$ is selected from hydrido, alkyl, hydroxyalkyl, formyl, halo, haloalkyl, cycloalkyl, alkylcycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, cyano, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyloxyalkyl, aryl/alkylsilyloxyalkyl, arylsilyloxyalkyl, mercaptoalkyl, alkoxycarbonyloxy, alkylthio, alkylthioalkyl, alkylsulfinylalkyl, alkylsulfonylalkyl and arylthio;

wherein each of $R^2$, $R^3$ and $R^4$ is independently selected from hydrido, alkyl, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, alkoxyalkyl, alkylcarbonyl, alkylcarbonylalkyl, alkylsilyloxyalkyl, alkoxycarbonyl, cyano, nitro, alkylthio, alkylthioalkyl, alkylsulfinylalkyl and alkylsulfonylalkyl;

wherein each of $R^5$, $R^6$, $R^7$ and $R^8$ independently selected from hydrido, alkyl, hydroxy, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyloxyalkyl, alkoxycarbonyloxy, alkylthio, alkylthioalkyl, alkylsulfinylalkyl, alkylsulfonylalkyl and arylthio with the proviso that at least one of $R^5$, $R^6$, $R^7$ and $R^8$ may be further independently selected from amino and amido radicals of the formulae

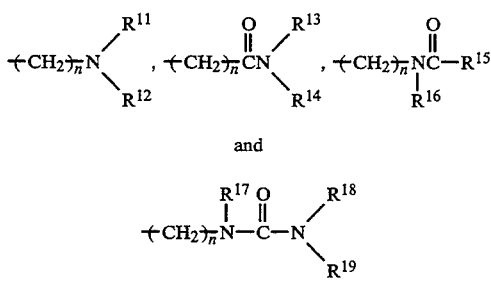

and $$\text{+CH}_2\text{)}_{\overline{n}} \overset{R^{17}}{\underset{|}{N}} - \overset{O}{\underset{||}{C}} - N\overset{R^{18}}{\underset{R^{19}}{\diagdown}}$$

wherein each n is a number independently selected from zero to five, inclusive; wherein each of $R^{11}$ through $R^{19}$ is independently selected from hydrido, alkyl, cycloalkyl, hydroxyalkyl, cycloalkylalkyl, alkoxyalkyl, aralkyl and aryl;
wherein each of $R^9$ and $R^{10}$ is independently selected from hydrido, alkyl, haloalkyl, cycloalkyl, polycycloalkyl, polycycloalkylalkyl, cycloalkylalkyl, aralkyl, aryl, alkenyl and cycloalkenyl; wherein any of said $R^9$ and $R^{10}$ groups may be substituted at one or more substitutable positions by one or more groups selected from alkyl, halo, haloalkyl and alkoxy; or a pharmaceutically-acceptable salt thereof.

3. Compound of claim 2 wherein m is a number selected from one through four, inclusive; wherein $R^1$ is selected from hydrido, alkyl, hydroxyalkyl, halo, haloalkyl, cycloalkyl, alkylcycloalkyl, cycloalkylalkyl, cycloalkylhaloalkyl, alkoxy, aralkyl, aralkylhaloalkyl, aryl, haloaryl, aryloxy, aryloxyalkyl, alkoxyalkyl, alkylcarbonylalkyl, cyano, carboxyalkyl, alkylcarbonyloxyalkyl, alkoxycarbonylalkyl, aralkoxycarbonylalkyl, aralkylcarbonyloxyalkyl, alkylsilyloxyalkyl, aryl/alkylsilyloxyalkyl, arylsilyloxyalkyl, mercaptoalkyl, alkylthio, alkylthioalkyl, alkylsulfinylalkyl, alkylsulfonylalkyl and arylthio;
  wherein each of $R^2$, $R^3$ and $R^4$ is independently selected from hydrido, alkyl, hydroxyalkyl, halo, haloalkyl, cycloalkyl, alkylcycloalkyl, cycloalkylalkyl, cycloalkylhaloalkyl, alkoxy, aralkyl, aralkylhaloalkyl, alkoxyalkyl, alkylcarbonylalkyl, alkylsilyloxyalkyl, cyano, nitro, alkylthio, alkylthioalkyl, alkylsulfinylalkyl and alkylsulfonylalkyl;
  wherein each of $R^5$, $R^6$, $R^7$ and $R^8$ is independently selected from hydrido, alkyl, hydroxy, hydroxyalkyl, halo, haloalkyl, cycloalkyl, alkylcycloalkyl, cycloalkylalkyl, alkoxy, aralkyl, aryl, haloaryl, aryloxy, aryloxyalkyl, aralkoxy, alkoxyalkyl, cyano, nitro, carboxyl, carboxyalkyl, alkylcarbonyloxy, alkylsilyloxyalkyl, alkoxycarbonyloxy, alkylthio, alkylthioalkyl, alkylsulfinylalkyl, alkylsulfonylalkyl and arylthio, with the proviso that at least one of $R^5$, $R^6$, and $R^7$ and $R^8$ must be a group other than hydrido;
  wherein each of $R^1$, $R^2$, $R^3$, $R^4$, $R^5$, $R^6$, $R^7$ and $R^8$ may be further independently selected from amino and amido radicals of the formulae

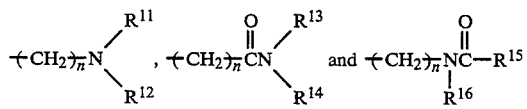

wherein each n is a number independently selected from zero to four, inclusive; wherein each of $R^{11}$ through $R^{16}$ is independently selected from hydrido, alkyl, cycloalkyl, hydroxyalkyl, cycloalkylalkyl, alkoxyalkyl, aralkyl and aryl;
wherein each of $R^9$ and $R^{10}$ is independently selected from hydrido, alkyl, haloalkyl, cycloalkyl, polycycloalkyl, polycycloalkylalkyl, cycloalkylalkyl, aralkyl, aryl, alkenyl and cycloalkenyl; wherein any of said $R^9$ and $R^{10}$ groups may be substituted at one or more substitutable positions by one or more groups selected from alkyl, halo, haloalkyl and alkoxy, with the proviso that when $R^9$ and $R^{10}$ is an alkenyl or a cycloalkenyl group, then the double bond of such group cannot be adjacent to the nitrogen atom of the amido group of Formula I; or a pharmaceutically-acceptable salt thereof.

4. Compound of claim 3 wherein m is a number selected from one through three, inclusive; wherein $R^1$ is selected from hydrido, alkyl, hydroxyalkyl, halo, haloalkyl, cycloalkyl, alkylcycloalkyl, cycloalkylalkyl, cycloalkylhaloalkyl, alkoxy, phenylalkyl, phenyl, halophenyl, phenoxy, phenoxyalkyl, alkoxyalkyl, cyano, alkylsilyloxyalkyl, phenyl/alkylsilyloxyalkyl, phenylsilyloxyalkyl, alkylthio and phenylthio;
  wherein each of $R^2$, $R^3$ and $R^4$ is independently selected from hydrido, alkyl, hydroxyalkyl, halo, haloalkyl, cycloalkyl, alkylcycloalkyl, cycloalkylalkyl, alkoxy, phenylalkyl, alkoxyalkyl, alkylcarbonylalkyl, alkylsilyloxyalkyl, cyano, nitro and alkylthio;
  wherein each of $R^5$, $R^6$, $R^7$ and $R^8$ is independently selected from hydrido, alkyl, hydroxy, hydroxyalkyl, halo, haloalkyl, cycloalkyl, alkylcycloalkyl, cycloalkylalkyl, alkoxy, phenylalkyl, phenyl, halophenyl, phenoxy, phenoxyalkyl, alkoxyalkyl, cyano, nitro, carboxyalkyl, alkylsilyloxyalkyl, alkylthio and phenylthio, with the proviso that at least one of $R^5$, $R^6$, $R^7$ and $R^8$ must be a group other than hydrido;
  wherein each of $R^1$, $R^2$, $R^3$, $R^4$, $R^5$, $R^6$, $R^7$ and $R^8$ may be further independently selected from amino and amido radicals of the formulae

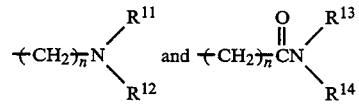

wherein each n is a number independently selected from zero to four, inclusive; wherein each of $R^{11}$ through $R^{14}$ is independently selected from hydrido, alkyl, cycloalkyl, hydroxyalkyl, cycloalkylalkyl, alkoxyalkyl, phenylalkyl and phenyl;
wherein each of $R^9$ and $R^{10}$ is independently selected from hydrido, alkyl, haloalkyl, cycloalkyl, polycycloalkyl, bicycloalkylalkyl, cycloalkylalkyl, phenylalkyl, phenyl, alkenyl and cycloalkenyl; wherein any of said $R^9$ and $R^{10}$ groups may be substituted at one or more substitutable positions by one or more groups selected from alkyl, halo, haloalkyl and alkoxy, with the proviso that when $R^9$ and $R^{10}$ is an alkenyl or a cycloalkenyl group, then the double bond of such group cannot be adjacent to the nitrogen atom of the amido group of Formula I; or a pharmaceutically-acceptable salt thereof.

5. Compound of claim 4 wherein m is one or two; wherein $R^1$ is selected from hydrido, alkyl, hydroxyalkyl, halo, haloalkyl, cycloalkyl, alkylcycloalkyl, cycloalkylalkyl, cycloalkylhaloalkyl, alkoxy, benzyl, phenyl, halophenyl, alkoxyalkyl, alkylsilyloxyalkyl, phenyl/alkylsilyloxyalkyl, phenylsilyloxyalkyl and alkylthio;

wherein each of $R^2$, $R^3$ and $R^4$ is independently selected from hydrido, alkyl, hydroxyalkyl, halo, haloalkyl, cycloalkyl, alkylcycloalkyl, cycloalkylalkyl, alkoxy, benzyl, alkoxyalkyl, alkylsilyloxyalkyl and alkylthio;

wherein each of $R^5$, $R^6$, $R^7$ and $R^8$ is independently selected from hydrido, alkyl, hydroxy, hydroxylalkyl, formyl, halo, haloalkyl, cycloalkyl, alkylcycloalkyl, cycloalkylalkyl, alkoxy, alkoxyalkyl, alkylsilyloxyalkyl and alkylthio, with the proviso that at least one of $R^5$, $R^6$, $R^7$ and $R^8$ must be a group other than hydrido;

wherein each of $R^1$, $R^2$, $R^3$, $R^4$, $R^5$, $R^6$, $R^7$ and $R^8$ may be further independently selected from amino radicals of the formula

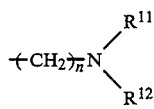

wherein each n is a number independently selected from zero to four, inclusive; wherein each of $R^{11}$ and $R^{12}$ is independently selected from hydrido, alkyl, cycloalkyl, hydroxyalkyl, cycloalkylalkyl, alkoxyalkyl, benzyl and phenyl;

wherein each of $R^9$ and $R^{10}$ is independently selected from hydrido, alkyl, haloalkyl, cycloalkyl, polycycloalkyl, bicycloalkylalkyl, cycloalkylalkyl, phenylalkyl, phenyl, alkenyl and cycloalkenyl; wherein any of said $R^9$ and $R^{10}$ groups may be substituted at one or more substitutable positions by one or more groups selected from alkyl, halo, haloalkyl and alkoxy, with the proviso that when $R^9$ and $R^{10}$ is an alkenyl or a cycloalkenyl group, then the double bond of such group cannot be adjacent to the nitrogen atom of the amido group of Formula I; or a pharmaceutically-acceptable salt thereof.

6. Compound of claim 5 wherein m is one; wherein $R^1$ is selected from hydrido, alkyl, hydroxyalkyl, alkoxyalkyl, phenyl, halophenyl, alkylsilyloxyalkyl, amino, monoalkylamino, dialkylamino, aminoalkyl, monoalkylaminoalkyl and dialkylaminoalkyl, wherein when $R^1$ is alkyl or is a group containing alkyl, then such alkyl has one to about six carbon atoms and may have a linear or branched configuration;

wherein each of $R^2$, $R^3$ and $R^4$ is hydrido;

wherein each of $R^5$, $R^6$, $R^7$ and $R^8$ is independently selected from hydrido, hydroxy, alkyl, alkoxy, fluoro, chloro, bromo, haloalkyl, alkylthio, alkoxyalkyl, hydroxyalkyl, alkylthioalkyl, cyano, amino, monoalkylamino, dialkylamino, aminoalkyl, monoalkylaminoalkyl and dialkylaminoalkyl, with the proviso that at least one of $R^5$, $R^6$, $R^7$ and $R^8$ must be a group other than hydrido; wherein when any of the foregoing $R^5$, $R^6$, $R^7$ and $R^8$ is alkyl or is a group containing alkyl, such alkyl has one to about six carbon atoms and may have a linear or branched configuration;

wherein each of $R^9$ and $R^{10}$ is independently selected from hydrido, linear or branched chain alkyl having 1 to about 15 carbon atoms, cycloalkyl having 3 to about 8 carbon atoms, bicycloalkyl having 3 to about 8 carbon atoms in each ring, phenyl, linear or branched alkenyl having 3 to about 15 carbon atoms with the proviso that the double bond of the alkenyl group cannot be adjacent to the nitrogen, cycloalkenyl having 5 to about 8 carbon atoms with the proviso that the double bond cannot be adjacent to the nitrogen of the amido group of Formula I, and wherein any of said $R^9$ and $R^{10}$ substituents may be further substituted with one or more groups selected from linear or branched lower alkyl, loweralkoxy, chloro and bromo; or a pharmaceutically-acceptable salt thereof.

7. Compound of claim 6 wherein m is one; wherein $R^1$ is selected from hydrido, methyl, ethyl, n-propyl, isopropyl, n-butyl, isobutyl, sec-butyl, tert-butyl, n-pentyl, isopentyl, neopentyl, hexyl, hydroxymethyl, hydroxyethyl, hydroxypropyl, hydroxybutyl, methoxymethyl, ethoxymethyl, propoxymethyl, butoxymethyl, methoxyethyl, methoxypropyl, methoxybutyl, ethoxyethyl, ethoxypropyl, ethoxybutyl, propoxymethyl, propoxyethyl, propoxypropyl, propoxybutyl, butoxymethyl, butoxyethyl, butoxypropyl, butoxybutyl, phenyl, monofluorophenyl, difluorophenyl, monochlorophenyl, dichlorophenyl, monobromophenyl, dibromophenyl, methylsilyloxymethyl, trimethylsilyloxyethyl, trimethylsilyloxyethyl, trimethylsilyloxybutyl, triethylsilyloxymethyl, triethylsilyloxyethyl, triethylsilyloxypropyl, triethylsilyloxybutyl, tripropylsilyloxymethyl, tripropylsilyloxyethyl, tripropylsilyloxypropyl, tripropylsilyloxybutyl, tert-butyl(dimethyl) silyloxymethyl, tert-butyl(dimethyl)silyloxyethyl, tert-butyl(dimethyl)silyloxypropyl, tert-butyl(dimethyl) silyloxybutyl, amino, N-methylamino, N,N'-dimethylamino, N-ethylamino, N,N'-diethylamino, N-propylamino, N,N'-dipropylamino, N-butylamino, N-N'-dibutylamino, N-methylaminomethyl, N-methylaminoethyl, N-methylaminopropyl, N-methylaminobutyl, N,N'-dimethylaminomethyl, N,N'-dimethylaminoethyl, N,N'-dimethylaminopropyl, N,N'-dimethylaminobutyl, N,N'-diethylaminomethyl, N,N'-diethylaminoethyl, N,N'-diethylaminopropyl, N,N'-diethylaminobutyl, N,N'-dipropylaminomethyl, N,N'-dipropylaminoethyl, N,N'-dipropylaminopropyl, N,N'-dipropylaminobutyl, N,N'-dibutylaminomethyl, N,N'-dibutylaminoethyl, N,N'-dibutylaminopropyl and N,N'-dibutylaminobutyl, wherein when $R^1$ is alkyl group or is one of the foregoing groups containing an alkyl group, such alkyl group may be linear or branched in configuration;

wherein each of $R^2$, $R^3$ and $R^4$ is hydrido;

wherein each of $R^5$, $R^6$, $R^7$ and $r^8$ is independently selected from hydrido, methyl, ethyl, n-propyl, isopropyl, n-butyl, isobutyl, sec-butyl, tert-butyl, n-pentyl, isopentyl, neopentyl, hexyl, fluoro, chloro, bromo, hydroxy, methoxy, ethoxy, propoxy, butoxy, pentoxy, trifluoromethyl, perfluoroethyl, dichloromethyl, methylthio, ethylthio, propylthio, butylthio, pentylthio, hydroxymethyl, hydroxyethyl, hydroxypropyl, hydroxybutyl, methoxymethyl, ethoxymethyl, propoxymethyl, butoxymethyl, methoxyethyl, methoxypropyl, methoxybutyl, ethoxyethyl, ethoxypropyl, ethoxybutyl, propoxymethyl, propoxyethyl, propoxypropyl, propoxybutyl, butoxymethyl, butoxyethyl, butoxypropyl, butoxybutyl, methylthiomethyl, methylthioethyl, methylthiopropyl, methylthiobutyl, ethylthiomethyl, ethylthioethyl, ethylthiopropyl, ethylthiobutyl, propylthiomethyl, propylthioethyl, propylthiopropyl, propylthiobutyl, butylthiomethyl, butylthioethyl, butylthiopropyl, butylthiobutyl, cyano, amino, N-methylamino, N,N'-dimethylamino, N-ethylamino, N,N'-diethylamino, N-propylamino, N,N'-dipropylamino, N-butylamino, N-N'-dibutylamino, N-methylaminomethyl, N-methylaminoethyl, N-methylaminopropyl, N-methylaminobutyl, N,N'-dimethylaminomethyl, N,N'-dimethylaminoethyl, N,N'-dimethylaminopropyl, N,N'-dimethylaminobutyl, N,N'-diethylaminomethyl, N,N'-diethylaminoethyl, N,N'-diethylaminopropyl, N,N'-diethylaminobutyl, N,N'-dipropylaminomethyl, N,N'-dipropylaminoethyl, N,N'-dipropylaminopropyl, N,N'-dipropylaminobutyl, N,N'-dibutylaminomethyl, N,N'-dibutylaminoethyl, N,N'-dibutylaminopropyl and N,N'-dibutylaminobutyl, with the proviso that at least one of $R^5$, $R^6$, $R^7$ and $R^8$ must be a group other than hydrido; wherein when any of $R^5$, $R^6$, $R^7$ and $R^8$ is alkyl or is a group containing alkyl, such alkyl group may be linear or branched in configuration.

wherein each of $R^9$ and $R^{10}$ is independently selected from hydrido, methyl, ethyl, n-propyl, isopropyl, isobutyl, sec-butyl, tert-butyl, n-pentyl, isopentyl, neopentyl, n-hexyl, n-heptyl, n-octyl, n-nonyl, n-decyl, 1,1,3,3-tetramethylbutyl, 2,2-dimethylethyl, 1,1-diethylmethyl, cyclopropyl, cyclobutyl, cyclohexyl, cycloheptyl, cyclooctyl, methylcyclopentyl, ethylcyclopentyl, 2-methylcyclohexyl, 3-methylcyclohexyl, 4-methylcyclohexyl, 3,5-dimethylcyclohexyl, ethylcyclohexyl, 3,5-diethylcyclohexyl, norbornyl, decalin, 2,2,1-bicycloheptyl, 2,2,1-bicycloheptylmethyl and phenyl; or a pharmaceutically-acceptable salt thereof.

8. Compound of claim 7 selected from compounds, and their pharmaceutically-acceptable salts, of the group of compounds consisting of N,N-dicyclopentyl-4-(3H-imidazo[4,5-b]pyridin-1-ylmethyl)-3-methoxybenzamide;

N,N-dicyclopentyl-4-(1H-imidazo[4,5-b]pyridin-1-ylmethyl)-3-methoxybenzamide;

N-cyclohexyl-4-(3H-imidazo[4,5-b]pyridin-3-ylmethyl)-2-methoxy-N-(1-methylethyl)benzamide;

N-cyclohexyl-4-(1H-imidazo[4,5-b]pyridin-1-ylmethyl)-2-methoxy-N-(1-methylethyl)benzamide;

N-cyclohexyl-4-(3H-imidazo[4,5-b]pyridin-3-ylmethyl)-3-methoxy-N-(1-methylethyl)benzamide;

N-cyclohexyl-4-(1H-imidazo[4,5-b]pyridin-1-ylmethyl)-3-methoxy-N-(1-methylethyl)benzamide;

N-cyclopentyl-N-(3,5-dimethylcyclohexyl)-4-(3H-imidazo[4,5-b]pyridin-3-ylmethyl)-2-methoxybenzamide;

N-cyclopentyl-N-(3,5-dimethylcyclohexyl)-4-(1H-imidazo[4,5-b]pyridin-1-ylmethyl)-2-methoxybenzamide;

N-cyclohexyl-N-cyclopentyl-4-(1H-imidazo[4,5-b]pyridin-1-ylmethyl)-3-methylbenzamide;

N-cyclohexyl-N-cyclopentyl-4-(3H-imidazo[4,5-b]pyridin-3-ylmethyl)-3-methylbenzamide;

N-cyclohexyl-3-methoxy-N-(1-methylethyl)-4-[(2-methyl-1H-imidazo[4,5-b]pyridin-1-yl)methyl]benzamide;

N-cyclohexyl-3-methoxy-N-(1-methylethyl)-4-[(2-methyl-3H-imidazo[4,5-b]pyridin-3-yl)methyl]benzamide;

N-cyclohexyl-N-cyclopentyl-4-(1H-imidazo[4,5-b]pyridin-1-ylmethyl)-2-methoxybenzamide;

4-[[2-(2-chlorophenyl)-1H-imidazo[4,5-b]pyridin-1-yl]methyl]-N-cyclohexyl-3-methoxy-N-(1-methylethyl)benzamide;

4-[[2-(2-chlorophenyl)-3H-imidazo[4,5-b]pyridin-3-yl]methyl]-N-cyclohexyl-3-methoxy-N-(1-methylethyl)benzamide;

N-cyclohexyl-4-[[2-[[[(1,1-dimethylethyl)dimethylsilyl]oxy]methyl]-1H-imidazo[4,5-b]pyridin-1-yl]methyl]-3-methoxy-N-(1-methylethyl)benzamide;

N-cyclohexyl-4-[[2-(hydroxymethyl)-1H-imidazo[4,5-b]pyridin-1-yl]methyl]-3-methoxy-N-(1-methylethyl)benzamide;

N-cyclohexyl-4-[[2-(hydroxymethyl)-3H-imidazo[4,5-b]pyridin-3-yl]methyl]-3-methoxy-N-(1-methylethyl)benzamide;

N-cyclohexyl-4-[[2-[(dimethylamino)methyl]-1H-imidazo[4,5-b]pyridin-1-yl]methyl]-3-methoxy-N-(1-methylethyl)benzamide;

N-cyclohexyl-4-[[2-[(dimethylamino)methyl]-3H-imidazo[4,5-b]pyridin-3-yl]methyl]-3-methoxy-N-(1-methylethyl)benzamide;

N-cyclohexyl-3-methoxy-4-[[2-(methoxymethyl)-1H-imidazo[4,5-b]pyridin-1-yl]methyl]-N-(1-methylethyl)benzamide;

N-cyclohexyl-3-methoxy-4-[[2-(methoxymethyl)-3H-imidazo[4,5-b]pyridin-3-yl]methyl]-N-(1-methylethyl)benzamide; and N-cyclohexyl-4-[[2-(dimethylamino)-1H-imidazo[4,5-b]pyridin-1-yl]methyl]-3-methoxy-N-(1-methylethyl)benzamide.

9. Compound of claim 8 which is N-cyclohexyl-4-(1H-imidazo[4,5-b]pyridin-1-ylmethyl)-2-methoxy-N-(1-methylethyl)benzamide or a pharmaceutically-acceptable salt thereof.

10. Compound of claim 8 which is N-cyclohexyl-4-[[2-(hydroxymethyl)-1H-imidazo[4,5-b]pyridin-1yl]methyl]-3-methoxy-N-(1-methylethyl)benzamide or a pharmaceutically-acceptable salt thereof.

11. Compound of claim 8 which is N-cyclohexyl-4-[[2-[(dimethylamino)methyl]-1H-imidazo[4,5-b ]pyridin-1-yl]methyl]-3-methoxy-N-(1-methylethyl)benzamide or a pharmaceutically-acceptable salt thereof.

12. Compound of claim 8 which is N-cyclohexyl-3-methoxy-4-[[2-(methoxymethyl)-1H-imidazo[4,5-b]pyridin-1-yl]methyl]-N-(1-methylethyl)benzamide or a pharmaceutically-acceptable salt thereof.

13. A pharmaceutical composition comprising at least one pharmaceutically-acceptable carrier or diluent and a therapeutically-effective amount of an active compound selected from compounds of Formula I:

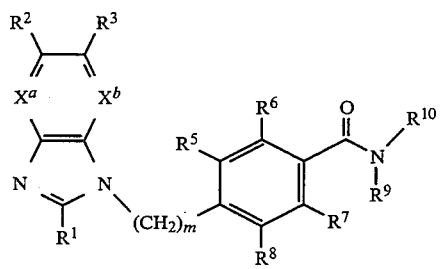

(I)

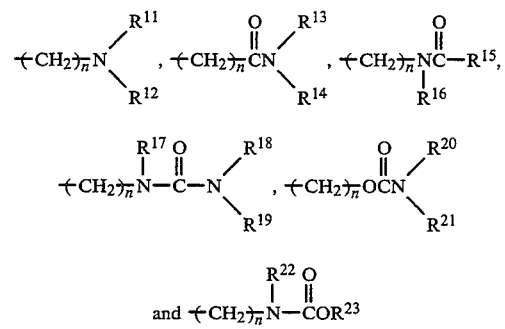

wherein each of $X^a$ and $X^b$ is independently selected from nitrogen atom and $>CR^4$, with the proviso that when one of $X^a$ and $X^b$ is selected as nitrogen atom then the other of $X^a$ and $X^b$ must be selected from $>CR^4$ and with the further proviso that one of $X^a$ and $X^b$ must be a nitrogen atom; wherein m is a number selected from one through six, inclusive;

wherein $R^1$ is selected from hydrido, alkyl, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyloxyalkyl, aryl/alkylsilyloxyalkyl, arylsilyloxyalkyl, mercaptoalkyl, alkoxycarbonyloxy, alkylthio, alkylthioalkyl, alkylsulfinylalkyl, alkylsulfonylalkyl, cycloalkylthio, cycloalkylalkylthio, alkylcarbonylthio, arylthio, arylcarbonylthio, aralkylthio and aralkylcarbonylthio;

wherein each of $R^2$, $R^3$ and $R^4$ is independently selected from hydrido, alkyl, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, alkoxyalkyl, alkylcarbonyl, alkylcarbonylalkyl, alkylsilyloxyalkyl, alkoxycarbonyl, cyano, nitro, alkylthio, alkylthioalkyl, alkylsulfinylalkyl, alkylsulfonylalkyl, cycloalkylthio and cycloalkylalkylthio;

wherein each of $R^5$, $R^6$, $R^7$ and $R^8$ is independently selected from hydrido, alkyl, hydroxy, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyloxyalkyl, alkoxycarbonyloxy, alkylthio, alkylthioalkyl, alkylsulfinylalkyl, alkylsulfonylalkyl, cycloalkylthio, cycloalkylalkylthio, alkylcarbonylthio, arylthio, arylcarbonylthio, aralkylthio and aralkylcarbonylthio, with the proviso that at least one $R^5$, $R^6$, $R^7$ and $R^8$ must be a group other than hydrido;

wherein each of $R^1$, $R^2$, $R^3$, $R^4$, $R^5$, $R^6$, $R^7$ and $R^8$ may be further independently selected from amino and amido radicals of the formulae wherein each n is a number independently selected from zero to six, inclusive; wherein each of $R^{11}$ through $R^{23}$ is independently selected from hydrido, alkyl, cycloalkyl, hydroxyalkyl, cycloalkylalkyl, alkoxyalkyl, aralkyl and aryl;

wherein each of $R^9$ and $R^{10}$ is independently selected from hydrido, alkyl, haloalkyl, cycloalkyl, polycycloalkyl, polycycloalkylalkyl, cycloalkylalkyl, aralkyl, aryl, alkenyl and cycloalkenyl, wherein any of said $R^9$ and $R^{10}$ groups may be substituted at one or more substitutable positions by one or more groups selected from alkyl, halo, haloalkyl and alkoxy; or a pharmaceutically-acceptable salt thereof.

14. The composition of claim 13 wherein said therapeutically-effective compound is of Formula IA or Formula IB:

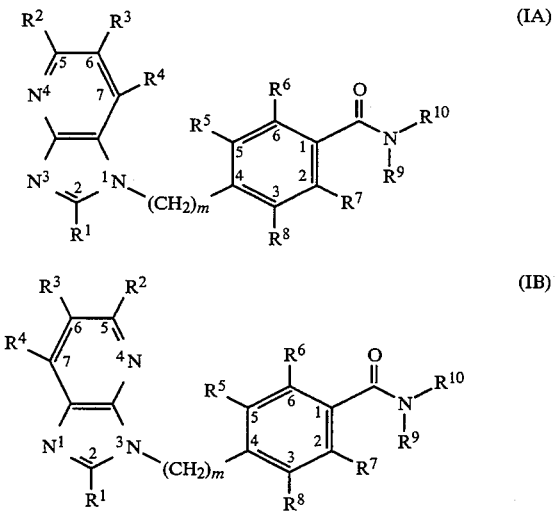

wherein m is a number selected from one through five, inclusive; wherein $R^1$ is selected from hydrido, alkyl, hydroxyalkyl, formyl, halo, haloalkyl, cycloalkyl, alkylcycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, cyano, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyloxyalkyl, aryl/alkylsilyloxyalkyl, arylsilyloxyalkyl, mercaptoalkyl, alkoxycarbonyloxy, alkylthio, alkylthioalkyl, alkylsulfinylalkyl, alkylsulfonylalkyl and arylthio;

wherein each of R², R³ and R⁴ is independently selected from hydrido, alkyl, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, alkoxyalkyl, alkylcarbonyl, alkylcarbonylalkyl, alkylsilyloxyalkyl, alkoxycarbonyl, cyano, nitro, alkylthio, alkylthioalkyl, alkylsulfinylalkyl and alkylsulfonylalkyl;

wherein each of $R^5$, $R^6$, $R^7$ and $R^8$ is independently selected from hydrido, alkyl, hydroxy, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyloxyalkyl, alkoxycarbonyloxy, alkylthio, alkylthioalkyl, alkylsulfinylalkyl, alkylsulfonylalkyl and arylthio, with the proviso that at least one of $R^5$, $R^6$, $R^7$ and $R^8$ must be a group other than hydrido;

wherein each of $R^1$, $R^2$, $R^3$, $R^4$m $R^5$, $R^6$, $R^7$ and $R^8$ may be further independently selected from amino and amido radicals of the formulae

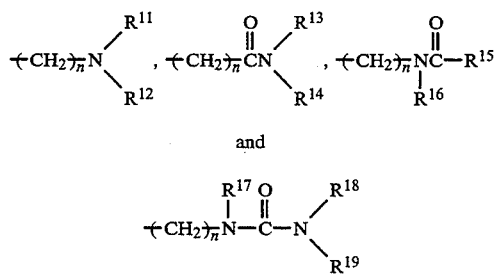

and $$\text{-}(\text{CH}_2)_n\text{N}-\overset{R^{17}}{\underset{|}{}}\overset{O}{\underset{\|}{\text{C}}}-\text{N}\overset{R^{18}}{\underset{R^{19}}{\diagdown}}$$

wherein each n is a number independently selected from zero to five, inclusive; wherein each of $R^{11}$ through $R^{19}$ is independently selected from hydrido, alkyl, cycloalkyl, hydroxyalkyl, cycloalkylalkyl, alkoxyalkyl, aralkyl and aryl;

wherein each of $R^9$ and $R^{10}$ is independently selected from hydrido, alkyl, haloalkyl, cycloalkyl, polycycloalkyl, polycycloalkylalkyl, cycloalkylalkyl, aralkyl, aryl, alkenyl and cycloalkenyl; wherein any of said $R^9$ and $R^{10}$ groups may be substituted at one or more substitutable positions by one or more groups selected from alkyl, halo, haloalkyl and alkoxy; or a pharmaceutically-acceptable salt thereof.

15. The composition of claim 14 wherein m is a number selected from one through four, inclusive; wherein $R^1$ is selected from hydrido, alkyl, hydroxyalkyl, halo, haloalkyl, cycloalkyl, alkylcycloalkyl, cycloalkylalkyl, cycloalkylhaloalkyl, alkoxy, aralkyl, aralkylhaloalkyl, aryl, haloaryl, aryloxy, aryloxyalkyl, alkoxyalkyl, alkylcarbonylalkyl, cyano, carboxyalkyl, alkylcarbonyloxyalkyl, alkoxycarbonylalkyl, aralkoxycarbonylalkyl, aralkylcarbonyloxyalkyl, alkylsilyloxyalkyl, aryl/alkylsilyloxyalkyl, arylsilyloxyalkyl, mercaptoalkyl, alkylthio, alkylthioalkyl, alkylsulfinylalkyl, alkylsulfonylalkyl and arylthio;

wherein each of R², R³ and R⁴ is independently selected from hydrido, alkyl, hydroxyalkyl, halo, haloalkyl, cycloalkyl, alkylcycloalkyl, cycloalkylalkyl, cycloalkylhaloalkyl, alkoxy, aralkyl, aralkylhaloalkyl, alkoxyalkyl, alkylcarbonylalkyl, alkylsilyloxyalkyl, cyano, nitro, alkylthio, alkylthioalkyl, alkylsulfinylalkyl and alkylsulfonylalkyl;

wherein each $R^5$, $R^6$, $R^7$ and $R^8$ is independently selected from hydrido, alkyl, hydroxy, hydroxyalkyl, halo, haloalkyl, cycloalkyl, alkylcycloalkyl, cycloalkylalkyl, alkoxy, aralkyl, aryl, haloaryl, aryloxy, aryloxyalkyl, aralkoxy, alkoxyalkyl, cyano, nitro, carboxyl, carboxyalkyl, alkylcarbonyloxy, alkylsilyloxyalkyl, alkoxycarbonyloxy, alkylthio, alkylthioalkyl, alkylsulfinylalkyl, alkylsulfonylalkyl and arylthio, with the proviso that at least one of $R^5$, $R^6$, $R^7$ and $R^8$ must be a group other than hydrido;

wherein each of $R^1$, $R^2$, $R^3$, $R^4$m $R^5$, $R^6$, $R^7$ and $R^8$ may be further independently selected from amino and amido radicals of the formulae

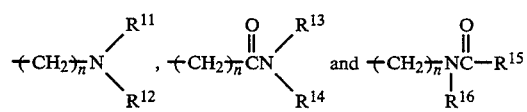

wherein each n is a number independently selected from zero to five, inclusive; wherein each of $R^{11}$ through $R^{16}$ is independently selected from hydrido, alkyl, cycloalkyl, hydroxyalkyl, cycloalkylalkyl, alkoxyalkyl, aralkyl and aryl;

wherein each of $R^9$ and $R^{10}$ is independently selected from hydrido, alkyl, haloalkyl, cycloalkyl, polycycloalkyl, polycycloalkylalkyl, cycloalkylalkyl, aralkyl, aryl, alkenyl and cycloalkenyl; wherein any of said $R^9$ and $R^{10}$ groups may be substituted at one or more substitutable positions by one or more groups selected from alkyl, halo, haloalkyl and alkoxy, with the proviso that when $R^9$ or $R^{10}$ is an alkenyl or a cycloalkenyl group, then the double bond of such group cannot be adjacent to the nitrogen atom of the amido group of Formula I; or a pharmaceutically-acceptable salt thereof.

16. The composition of claim 15 wherein m is a number selected from one through three, inclusive; wherein $R^1$ is selected from hydrido, alkyl, hydroxyalkyl, halo, haloalkyl, cycloalkyl, alkylcycloalkyl, cycloalkylalkyl, cycloalkylhaloalkyl, alkoxy, phenylalkyl, phenyl, halophenyl, phenoxy, phenoxyalkyl, alkoxyalkyl, cyano, alkylsilyloxyalkyl, phenyl/alkylsilyloxyalkyl, phenylsilyloxyalkyl, alkylthio and phenylthio;

wherein each of R², R³ and R⁴ is independently selected from hydrido, alkyl, hydroxyalkyl, halo, haloalkyl, cycloalkyl, alkylcycloalkyl, cycloalkylalkyl, alkoxy, phenylalkyl, alkoxyalkyl, alkylcarbonylalkyl, alkylsilyloxyalkyl, cyano, nitro and alkylthio;

wherein each of $R^5$, $R^6$, $R^7$ and $R^8$ is independently selected from hydrido, alkyl, hydroxy, hydroxyalkyl, halo, haloalkyl, cycloalkyl, alkylcycloalkyl, cycloalkylalkyl, alkoxy, phenylalkyl, phenyl, halophenyl, phenyloxy, phenyloxyalkyl, alkoxyalkyl, cyano, nitro, carboxyalkyl, alkylsilyloxyalkyl, alkylthio and phenylthio, with the proviso that at least one of $R^5$, $R^6$, $R^7$ nd $R^8$ must be a group other than hydrido;

wherein each of $R^1$, $R^2$, $R^3$, $R^4$m $R^5$, $R^6$, $R^7$ and $R^8$ may be further independently selected from amino and amido radicals of the formulae

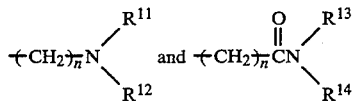

wherein each n is a number independently selected from zero to five, inclusive; wherein each of $R^{11}$ through $R^{14}$ is independently selected from hydrido, alkyl, cycloalkyl, hydroxyalkyl, cycloalkylalkyl, alkoxyalkyl, phenylalkyl and phenyl;

wherein each of $R^9$ and $R^{10}$ is independently selected from hydrido, alkyl, haloalkyl, cycloalkyl, bicycloalkyl, bicycloalkylalkyl, cycloalkylalkyl, phenylalkyl, phenyl, alkenyl and cycloalkenyl; wherein any of said $R^9$ and $R^{10}$ groups may be substituted at one or more substitutable positions by one or more groups selected from alkyl, halo, haloalkyl and alkoxy, with the proviso that when $R^9$ or $R^{10}$ is an alkenyl or a cycloalkenyl group, then the double bond of such group cannot be adjacent to the nitrogen atom of the amido group of Formula I; or a pharmaceutically-acceptable salt thereof.

17. The composition of claim 16 wherein m is one or two; wherein $R^1$ is selected from hydrido, alkyl, hydroxyalkyl, halo, haloalkyl, cycloalkyl, alkylcycloalkyl, cycloalkylalkyl, cycloalkylhaloalkyl, alkoxy, benzyl, phenyl, halophenyl, alkoxyalkyl, alkylsilyloxyalkyl, phenyl/alkylsilyloxyalkyl, phenylsilyloxyalkyl and alkylthio;

wherein each of $R^2$, $R^3$ and $R^4$ is independently selected from hydrido, alkyl, hydroxyalkyl, halo, haloalkyl, cycloalkyl, alkylcycloalkyl, cycloalkylalkyl, alkoxy, benzyl, alkoxyalkyl, alkylsilyloxyalkyl and alkylthio;

wherein each of $R^5$, $R^6$, $R^7$ and $R^8$ is independently selected from hydrido, alkyl, hydroxy, hydroxyalkyl, formyl, halo, haloalkyl, cycloalkyl, alkylcycloalkyl, cycloalkylalkyl, alkoxy, alkoxyalkyl, alkylsilyloxyalkyl and alkylthio, with the proviso that at least one of $R^5$, $R^6$, $R^7$ and $R^8$ must be a group other than hydrido;

wherein each of $R^1$, $R^2$, $R^3$, $R^4$, $R^5$, $R^6$, $R^7$ and $R^8$ may be further independently selected from amino radicals of the formula

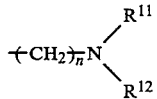

wherein each n is a number independently selected from zero to four, inclusive; wherein each of $R^{11}$ and $R^{12}$ is independently selected from hydrido, alkyl, cycloalkyl, hydroxyalkyl, cycloalkylalkyl, alkoxyalkyl, benzyl and phenyl;

wherein each of $R^9$ and $R^{10}$ is independently selected from hydrido, alkyl, haloalkyl, cycloalkyl, bicycloalkyl, bicycloalkylalkyl, cycloalkylalkyl, phenylalkyl, phenyl, alkenyl and cycloalkenyl; wherein any of said $R^9$ and $R^{10}$ groups may be substituted at one or more substitutable positions by one or more groups selected from alkyl, halo, haloalkyl and alkoxy, with the proviso that when $R^9$ or $R^{10}$ is an alkenyl or a cycloalkenyl group, then the double bond of such group cannot be adjacent to the nitrogen atom of the amido group of Formula I; or a pharmaceutically-acceptable salt thereof.

18. The composition of claim 17 wherein m is one; wherein $R^1$ is selected from hydrido, alkyl, hydroxyalkyl, alkoxyalkyl, phenyl, halophenyl, alkylsilyloxyalkyl, amino, monoalkylamino, dialkylamino, aminoalkyl, monoalkylaminoalkyl and dialkylaminoalkyl, wherein when $R^1$ is alkyl or is a group containing alkyl, then such alkyl has one to about six carbon atoms and may have a linear or branched configuration;

wherein each of $R^2$, $R^3$ and $R^4$ is hydrido;

wherein each of $R^5$, $R^6$, $R^7$ and $R^8$ is independently selected from hydrido, hydroxy, alkyl, alkoxy, fluoro, chloro, bromo, haloalkyl, alkylthio, alkoxyalkyl, hydroxyalkyl, alkylthioalkyl, cyano, amino, monoalkylamino, dialkylamino, aminoalkyl, monoalkylaminoalkyl and dialkylaminoalkyl, with the proviso that at least one of $R^5$, $R^6$, $R^7$ and $R^8$ must be a group other than hydrido; wherein when any of the foregoing $R^5$, $R^6$, $R^7$ and $R^8$ is alkyl or is a group containing alkyl, such alkyl has one to about six carbon atoms and may have a linear or branched configuration;

wherein each of $R^9$ and $R^{10}$ is independently selected from hydrido, linear or branched chain alkyl having 1 to about 15 carbon atoms, cycloalkyl having 3 to about 8 carbon atoms, bicycloalkyl having 3 to about 8 carbon atoms in each ring, phenyl, linear or branched alkenyl having 3 to about 15 carbon atoms with the proviso that the double bond of the alkenyl group cannot be adjacent to the nitrogen, cycloalkenyl having 5 to about 8 carbon atoms with the proviso that the double bond cannot be adjacent to the nitrogen of the amido group of Formula I, and wherein any of said $R^9$ and $R^{10}$ substituents may be further substituted with one or more groups selected from linear or branched lower alkyl, loweralkoxy, chloro and bromo; or a pharmaceutically-acceptable salt thereof.

19. The composition of claim 18 wherein m is one; wherein $R^1$ is selected from hydrido, methyl, ethyl, n-propyl, isopropyl, n-butyl, isobutyl, sec-butyl, tert-butyl, n-pentyl, isopentyl, neopentyl, hexyl, hydroxymethyl, hydroxyethyl, hydroxypropyl, hydroxybutyl, methoxymethyl, ethoxymethyl, propoxymethyl, butoxymethyl, methoxyethyl, methoxypropyl, methoxybutyl, ethoxyethyl, ethoxypropyl, ethoxybutyl, propoxymethyl, propoxyethyl, propoxypropyl, propoxybutyl, butoxymethyl, butoxyethyl, butoxypropyl, butoxybutyl, phenyl, monofluorophenyl, difluorophenyl, monochlorophenyl, dichlorophenyl, monobromophenyl, dibromophenyl, methylsilyloxymethyl, trimethylsilyloxyethyl, trimethylsilyloxypropyl, trimethylsilyloxybutyl, triethylsilyloxymethyl, triethylsilyloxyethyl, triethylsilyloxypropyl, triethylsilyloxybutyl, tripropylsilyloxymethyl, tripropylsilyloxyethyl, tripropylsilyloxypropyl, tripropylsilyloxybutyl, tert-butyl(dimethyl) silyloxymethyl, tert-butyl(dimethyl)silyloxyethyl, tert-butyl(dimethyl)silyloxypropyl, tert-butyl(dimethyl silyloxybutyl, amino, N-methylamino, N,N'-dimethylamino, N-ethylamino, N,N'-diethylamino, N-propylamino, N,N'-dipropylamino, N-butylamino, N-N'-dibutylamino, N-methylaminomethyl, N-methylaminoethyl, N-methylaminopropyl, N-methylaminobutyl, N,N'-dimethylaminomethyl, N,N'-dimethylaminoethyl, N,N'-dimethylaminopropyl, N,N'-dimethylaminobutyl, N,N'-diethylaminomethyl, N,N'-diethylaminoethyl, N,N'-diethylaminopropyl, N,N'-diethylaminobutyl, N,N'-dipropylaminomethyl, N,N'-dipropylaminoethyl, N,N'-dipropylaminopropyl, N,N'-dipropylaminobutyl, N,N'-dibutylaminomethyl, N,N'-dibutylaminoethyl, N,N'-dibutylaminopropyl and N,N'-dibutylaminobutyl, wherein when $R^1$ is alkyl group or is one of the foregoing groups containing an alkyl group, such alkyl group may be linear or branched in configuration;

wherein each of $R^2$, $R^3$ and $R^4$ is hydrido;

wherein each of $R^5$, $R^6$, $R^7$ and $R^8$ is independently selected from hydrido, methyl, ethyl, n-propyl, isopropyl, n-butyl, isobutyl, sec-butyl, tert-butyl, n-pentyl, isopentyl, neopentyl, hexyl, fluoro, chloro, bromo, hydroxy, methoxy, ethoxy, propoxy, butoxy, pentoxy, trifluoromethyl, perfluoroethyl, dichloromethyl, methylthio, ethylthio, propylthio, butylthio, pentylthio, hydroxymethyl, hydroxyethyl, hydroxypropyl, hydroxybutyl, methoxymethyl, ethoxymethyl, propoxymethyl, butoxymethyl, methoxyethyl, methoxypropyl, methoxybutyl, ethoxyethyl, ethoxypropyl, ethoxybutyl, propoxymethyl, propoxyethyl, propoxypropyl, propoxybutyl, butoxymethyl, butoxyethyl, butoxypropyl, butoxybutyl, methylthiomethyl, methylthioethyl, methylthiopropyl, methylthiobutyl, ethylthiomethyl, ethylthioethyl, ethylthiopropyl, ethylthiobutyl, propylthiomethyl, propylthioethyl, propylthiopropyl, propylthiobutyl, butylthiomethyl, butylthioethyl, butylthiopropyl, butylthiobutyl, cyano, amino, N-methylamino, N,N'-dimethylamino, N-ethylamino, N,N'-diethylamino, N-propylamino, N,N'-dipropylamino, N-butylamino, N-N'-butylamino, N-methylaminomethyl, N-methylaminoethyl, N-methylaminopropyl, N-methylaminobutyl, N,N'-dimethylaminomethyl, N,N'-dimethylaminoethyl, N,N'-dimethylaminopropyl, N,N'-dimethylaminobutyl, N,N'-diethylaminomethyl, N,N'-diethylaminoethyl, N,N'-diethylaminopropyl, N,N'-diethylaminobutyl, N,N'-dipropylaminomethyl, N,N'-dipropylaminoethyl, N,N'-dipropylaminopropyl, N,N'-dipropylaminobutyl, N,N'-dibutylaminomethyl, N,N'-dibutylaminoethyl, N,N'-dibutylaminopropyl and N,N'-dibutylaminobutyl, with the provision that at least one of $R^5$, $R^6$, $R^7$ and $R^8$ must be a group other than hydrido; wherein when any of $R^5$, $R^6$, $R^7$ and $R^8$ is alkyl or is a group containing alkyl, such alkyl group may be linear or branched in configuration;

wherein each of $R^9$ and $R^{10}$ is independently selected from hydrido, methyl, ethyl, n-propyl, isopropyl, isobutyl, sec-butyl, tert-butyl, n-pentyl, isopentyl, neopentyl, n-hexyl, n-heptyl, n-octyl, n-nonyl, n-decyl, 1,1,3,3-tetramethylbutyl, 2,2-dimethylethyl, 1,1-diethylmethyl, cyclopropyl, cyclobutyl, cyclohexyl, cycloheptyl, cyclooctyl, methylcyclopentyl, ethylcyclopentyl, 2-methylcyclohexyl, 3-methylcyclohexyl, 4-methylcyclohexyl, 3,5-dimethylcyclohexyl, ethylcyclohexyl, 3,5-diethylcyclohexyl, norbornyl, decalin, 2,2,1-bicycloheptyl, 2,2,1-bicycloheptylmethyl and phenyl; or a pharmaceutically-acceptable salt thereof.

20. The composition of claim 19 wherein said therapeutically-effective compound is selected from compounds, and their pharmaceutically-acceptable salts, of the group of compounds consisting of N,N-dicyclopentyl-4-(3H-imidazo[4,5-b]pyridin-1-ylmethyl)-3-methoxybenzamide;

N,N-dicyclopentyl-4-(1H-imidazo[4,5-b]pyridin-1-ylmethyl)-3-methoxybenzamide;

N-cyclohexyl-4-(3H-imidazo[4,5-b]pyridin-3-ylmethyl)-2-methoxy-N-(1-methylethyl)benzamide;

N-cyclohexyl-4-(1H-imidazo[4,5-b]pyridin-1-ylmethyl)-2-methoxy-N-(1-methylethyl)benzamide;

N-cyclohexyl-4-(3H-imidazo[4,5-b]pyridin-3-ylmethyl)-3-methoxy-N-(1-methylethyl)benzamide;

N-cyclohexyl-4-(1H-imidazo[4,5-b]pyridin-1-ylmethyl)-3-methoxy-N-(1-methylethyl)benzamide;

N-cyclopentyl-N-(3,5-dimethylcyclohexyl)-4-(3H-imidazo[4,5-b]pyridin-3-ylmethyl)-2-methoxybenzamide;

N-cyclopentyl-N-(3,5-dimethylcyclohexyl)-4-(1H-imidazo[4,5-b]pyridin-1-ylmethyl)-2-methoxybenzamide;

N-cyclohexyl-N-cyclopentyl-4-(1H-imidazo[4,5-b]pyridin-1-ylmethyl)-3-methylbenzamide;

N-cyclohexyl-N-cyclopentyl-4-(3H-imidazo[4,5-b]pyridin-3-ylmethyl)-3-methylbenzamide;

N-cyclohexyl-3-methoxy-N-(1-methylethyl)-4-[(2-methyl-1H-imidazo[4,5-b]pyridin-1-yl)methyl]benzamide;

N-cyclohexyl-3-methoxy-N-(1-methylethyl)-4-[(2-methyl-3H-imidazo[4,5-b]pyridin-3-yl)methyl]benzamide;

N-cyclohexyl-N-cyclopentyl-4-(1H-imidazo[4,5-b]pyridin-1-ylmethyl)-2-methoxybenzamide;

4-[[2-(2-chlorophenyl)-1H-imidazo[4,5-b]pyridin-1-yl]methyl]-N-cyclohexyl-3-methoxy-N-(1-methylethyl)benzamide;

4-[[2-(2-chlorophenyl)-3H-imidazo[4,5-b]pyridin-3-yl]methyl]-N-cyclohexyl-3-methoxy-N-(1-methylethyl)benzamide;

N-cyclohexyl-4-[[2-[[[(1,1-dimethylethyl)dimethylsilyl]oxy]methyl]-1H-imidazo[4,5-b]pyridin-1-yl]methyl]-3-methoxy-N-(1-methylethyl)benzamide;

N-cyclohexyl-4-[[2-(hydroxymethyl)-1H-imidazo[4,5-b]pyridin-1-yl]methyl]-3-methoxy-N-(1-methoxyethyl)benzamide;

N-cyclohexyl-4-[[2(hydroxymethyl)-3H-imidazo[4,5-b]pyridin-3-yl]methyl]-3-methoxy-N-(1-methylethyl)benzamide;

N-cyclohexyl-4-[[2-[(dimethylamino)methyl]-1H-imidazo[4,5-b]pyridin-1-yl]methyl]-3-methoxy-N-(1-methylethyl)benzamide;

N-cyclohexyl-4-[[2-[(dimethylamino)methyl]-3H-imidazo[4,5-b]pyridin-3-yl]methyl]-3-methoxy-N-(1-methylethyl)benzamide;

N-cyclohexyl-3-methoxy-4-[[2-(methoxymethyl)-1H-imidazo[4,5-b]pyridin-1-yl]methyl]-N-(1-methylethyl)benzamide;

N-cyclohexyl-3-methoxy-4-[[2-(methoxymethyl)-3H-imidazo[4,5-b]pyridin-3-yl]methyl]-N-(1-methylethyl)benzamide; and N-cyclohexyl-4-[[2-(dimethylamino)-1H-imidazo[4,5-b]pyridin-1-yl]methyl]-3-methoxy-N-(1-methylethyl)benzamide.

21. The composition of claim 20 wherein said compound which is N-cyclohexyl-4-(1H-imidazo[4,5-b]pyridin-1-ylmethyl)-2-methoxy-N-(1-methylethyl)-benzamide or a pharmaceutically-acceptable salt thereof.

22. The composition of claim 20 wherein said compound which is N-cyclohexyl-4-[[2-(hydroxymethyl)-1H-imidazo[4,5-b]pyridin-1-yl]methyl]-3-methoxy-N-(1-methylethyl)benzamide or a pharmaceutically-acceptable salt thereof.

23. The composition of claim 20 wherein said compound which is N-cyclohexyl-4-[[2-[(dimethylamino)methyl]-1H-imidazo[4,5-b]pyridin-1-yl]methyl]-3-methoxy-N-(1-methylethyl)benzamide or a pharmaceutically-acceptable salt thereof.

24. The composition of claim 20 wherein said compound which is N-cyclohexyl-3-methoxy-4-[[2-(methoxymethyl)-1H-imidazo[4,5-b]pyridin-1-yl]methyl]-N-(1-methylethyl)benzamide or a pharmaceutically-acceptable salt thereof.

25. A method for treating an asthmatic condition, said method comprising administering to a subject susceptible to or afflicted with said asthmatic condition, a therapeutically-effective amount of a compound of of Formula I:

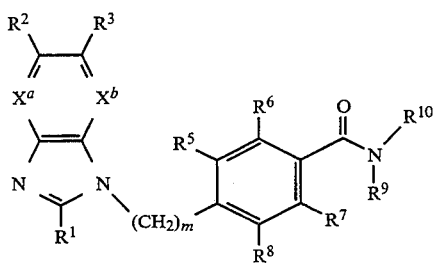

wherein each of $X^a$ and $X^b$ is independently selected from nitrogen atom and $>CR^4$, with the proviso that when one of $X^a$ and $X^b$ is selected as nitrogen atom then the other of $X^a$ and $X^b$ must be selected from $>CR^4$ and with the further proviso that one of $X^a$ and $X^b$ must be a nitrogen atom; wherein m is a number selected from one through six, inclusive; wherein $R^1$ is selected from hydrido, alkyl, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyloxyalkyl, aryl/alkylsilyloxyalkyl, arylsilyloxyalkyl, mercaptoalkyl, alkoxycarbonyloxy, alkylthio, alkylthioalkyl, alkylsulfinylalkyl, alkylsulfonylalkyl, cycloalkylthio, cycloalkylalkylthio, alkylcarbonylthio, arylthio, arylcarbonylthio, aralkylthio and aralkylcarbonylthio;

wherein each of $R^2$, $R^3$ and $R^4$ is independently selected from hydrido, alkyl, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, alkoxyalkyl, alkylcarbonyl, alkylcarbonylalkyl, alkylsilyloxyalkyl, alkoxycarbonyl, cyano, nitro, alkylthio, alkylthioalkyl, alkylsulfinylalkyl, alkylsulfonylalkyl, cycloalkylthio and cycloalkylalkylthio;

wherein each of $R^5$, $R^6$, $R^7$ and $R^8$ is independently selected from hydrido, alkyl, hydroxy, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyloxyalkyl, alkoxycarbonyloxy, alkylthio, alkylthioalkyl, alkylsulfinylalkyl, alkylsulfonylalkyl, cycloalkylthio, cycloalkylalkylthio, alkylcarbonylthio, arylthio, arylcarbonylthio, aralkylthio and aralkylcarbonylthio, with the proviso that at least one of $R^5$, $R^6$, $R^7$ and $R^8$ must be a group other than hydrido;

wherein each of $R^1$, $R^2$, $R^3$, $R^4$, $R^5$, $R^6$, $R^7$ and $R^8$ may be further independently selected from amino and amido radicals of the formulae

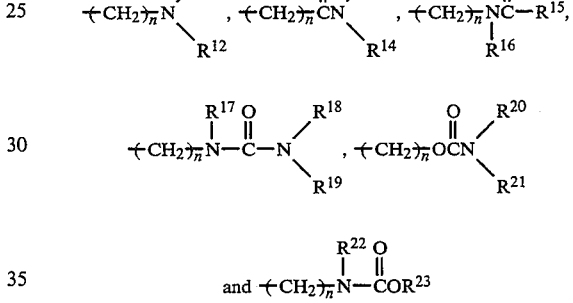

wherein each n is a number independently selected from zero to six, inclusive; wherein each of $R^{11}$ through $R^{23}$ is independently selected from hydrido, alkyl, cycloalkyl, hydroxyalkyl, cycloalkylalkyl, alkoxyalkyl, aralkyl and aryl;

wherein each of $R^9$ and $R^{10}$ is independently selected from hydrido, alkyl, haloalkyl, cycloalkyl, polycycloalkyl, polycycloalkyl, cycloalkylalkyl, aralkyl, aryl, alkenyl and cycloalkenyl, wherein any of said $R^9$ and $R^{10}$ groups may be substituted at one or more substitutable positions by one or more groups selected from alkyl, halo, haloalkyl and alkoxy; or a pharmaceutically-acceptable salt thereof.

26. The method of claim 26 wherein said therapeutically-effective compound is of Formula IA or Formula IB:

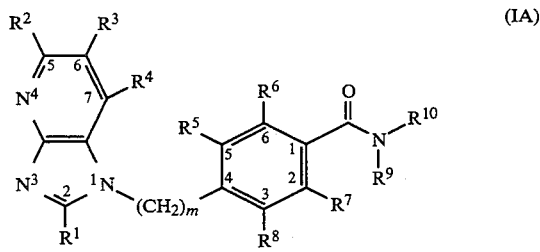

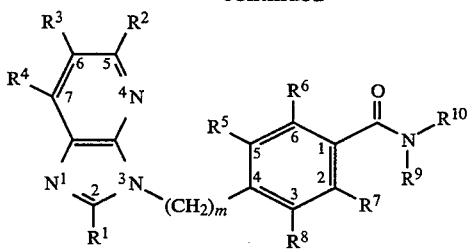

wherein m is a number selected from one through five, inclusive; wherein $R^1$ is selected from hydrido, alkyl, hydroxyalkyl, formyl, halo, haloalkyl, cycloalkyl, alkylcycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, cyano, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyloxyalkyl, arylsilyloxyalkyl, mercaptoalkyl, alkoxycarbonyloxy, alkylthio, alkylthioalkyl, alkylsulfinylalkyl, alkylsulfonylalkyl and arylthio;

wherein each of $R^2$, $R^3$ and $R^4$ is independently selected from hydrido, alkyl, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, alkoxyalkyl, alkylcarbonyl, alkylcarbonylalkyl, alkylsilyloxyalkyl, alkoxycarbonyl, cyano, nitro, alkylthio, alkylthioalkyl, alkylsulfinylalkyl and alkylsulfonylalkyl;

wherein each of $R^5$, $R^6$, $R^7$ and $R^8$ is independently selected from hydrido, alkyl, hydroxy, hydroxyalkyl, formyl, halo, haloalkyl, cycloalkyl, alkylcycloalkyl, cycloalkylalkyl, cycloalkylhaloalkyl, cycloalkylcarbonyl, alkoxy, aralkyl, aralkylhaloalkyl, aryl, haloaryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, alkylsilyloxyalkyl, alkoxycarbonyloxy, alkylthio, alkylthioalkyl, alkylsulfinylalkyl, alkylsulfonylalkyl and arylthio, with the proviso that at least one of $R^5$, $R^6$, $R^7$ and $R^8$ must be a group other than hydrido;

wherein each of $R^1$, $R^2$, $R^3$, $R^4$, $R^5$, $R^6$, $R^7$ and $R^8$ may be further independently selected from amino and amido radicals of the formulae

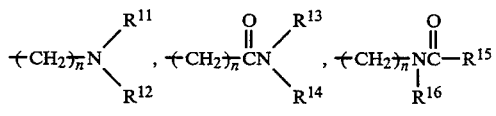

and

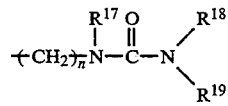

wherein each n is a number independently selected from zero to five inclusive; wherein each of $R^{11}$ through $R^{19}$ is independently selected from hydrido, alkyl, cycloalkyl, hydroxyalkyl, cycloalkylalkyl, alkoxyalkyl, aralkyl and aryl;

wherein each of $R^9$ and $R^{10}$ is independently selected from hydrido, alkyl, haloalkyl, cycloalkyl, polycycloalkyl, polycycloalkyl, cycloalkylalkyl, aralkyl, aryl, alkenyl and cycloalkenyl, wherein any of said $R^9$ and $R^{10}$ groups may be substituted at one or more substitutable positions by one or more groups selected from alkyl, halo, haloalkyl and alkoxy; or a pharmaceutically-acceptable salt thereof.

27. The method of claim 26 wherein m is a number selected from one through four, inclusive; wherein $R^1$ is selected from hydrido, alkyl, hydroxyalkyl, halo, haloalkyl, cycloalkyl, alkylcycloalkyl, cycloalkylalkyl, cycloalkylhaloalkyl, alkoxy, aralkyl, aralkylhaloalkyl, aryl, haloaryl, aryloxy, aryloxyalkyl, alkoxyalkyl, alkylcarbonylalkyl, cyano, carboxyalkyl, alkylcarbonyloxyalkyl, alkoxycarbonylalkyl, aralkoxycarbonylalkyl, aralkylcarbonyloxyalkyl, alkylsilyloxyalkyl, aryl/alkylsilyloxyalkyl, arylsilyloxyalkyl, mercaptoalkyl, alkylthio, alkylthioalkyl, alkylsulfinylalkyl, alkylsulfonylalkyl and arylthio;

wherein each of $R^2$, $R^3$, $R^4$, $R^5$, $R^6$, $R^7$ and $R^8$ is independently selected from hydrido, alkyl, hydroxyalkyl, halo, haloalkyl, cycloalkyl, alkylcycloalkyl, cycloalkylalkyl, cycloalkylhaloalkyl, alkoxy, aralkyl, aralkylhaloalkyl, alkoxyalkyl, alkylcarbonylalkyl, alkylsilyloxyalkyl, cyano, nitro, alkylthio, alkylthioalkyl, alkylsulfinylalkyl and alkylsulfonylalkyl;

wherein each of $R^5$, $R^6$, $R^7$ and $R^8$ is independently selected from hydrido, alkyl, hydroxy, hydroxyalkyl, halo, haloalkyl, cycloalkyl, alkylcycloalkyl, cycloalkylalkyl, alkoxy, aralkyl, aryl, haloaryl, aryloxy, aryloxyalkyl, aralkoxy, alkoxyalkyl, cyano, nitro, carboxyl, carboxyalkyl, alkylcarbonyloxy, alkylsilyloxyalkyl, alkoxycarbonyloxy, alkylthio, alkylthioalkyl, alkylsulfinylalkyl, alkylsulfonylalkyl and arylthio, with the proviso that at least one of $R^5$, $R^6$, $R^7$ and $R^8$ must be a group other than hydrido;

wherein each of $R^1$, $R^2$, $R^3$, $R^4$, $R^5$, $R^6$, $R^7$ and $R^8$ may be further independently selected from amino and amido radicals of the formulae

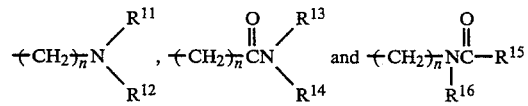

wherein each n is a number independently selected from zero to four, inclusive; wherein each of $R^{11}$ through $R^{16}$ is independently selected from hydrido, alkyl, cycloalkyl, hydroxyalkyl, cycloalkylalkyl, alkoxyalkyl, aralkyl and aryl;

wherein each of $R^9$ and $R^{10}$ is independently selected from hydrido, alkyl, haloalkyl, cycloalkyl, polycycloalkyl, polycycloalkyl, cycloalkylalkyl, aralkyl, aryl, alkenyl and cycloalkenyl, wherein any of said $R^9$ and $R^{10}$ groups may be substituted at one or more substitutable positions by one or more groups selected from alkyl, halo, haloalkyl and alkoxy, with the proviso that when $R^9$ or $R^{10}$ is an alkenyl or a cycloalkenyl group, then the double bond of such group cannot be adjacent to the nitrogen atom of the amido group of Formula I; or a pharmaceutically-acceptable salt thereof.

28. The method of claim 27 wherein m is a number selected from one through three, inclusive; wherein $R^1$ is selected from hydrido, alkyl, hydroxyalkyl, halo, haloalkyl, cycloalkyl, alkylcycloalkyl, cycloalkylalkyl, cycloalkylhaloalkyl, alkoxy, phenylalkyl, phenyl, halophenyl, phenoxy, phenoxyalkyl, alkoxyalkyl, cyano, alkylsilyloxyalkyl, phenyl/alkylsilyloxyalkyl, phenylsilyloxyalkyl, alkylthio and phenylthio;

wherein each of $R^2$, $R^3$ and $R^4$ is independently selected from hydrido, alkyl, hydroxyalkyl, halo, haloalkyl, cycloalkyl, alkylcycloalkyl, cycloalkylalkyl, alkoxy, phenylalkyl, alkoxyalkyl, alkylcarbonylalkyl, alkylsilyloxyalkyl, cyano, nitro and alkylthio;

wherein each of $R^5$, $R^6$, $R^7$ and $R^8$ is independently selected from hydrido, alkyl, hydroxy, hydroxyalkyl, halo, haloalkyl, cycloalkyl, alkylcycloalkyl, cycloalkylalkyl, alkoxy, phenylalkyl, phenyl, halophenyl, phenyloxy, phenyloxyalkyl, alkoxyalkyl, cyano, nitro, carboxyalkyl, alkylsilyloxyalkyl, alkylthio and phenylthio, with the proviso that at least one of $R^5$, $R^6$, $R^7$ and $R^8$ must be a group other than hydrido;

wherein each of $R^1$, $R^2$, $R^3$, $R^4$, $R^5$, $R^6$, $R^7$ and $R^8$ may be further independently selected from amino and amido radicals of the formulae

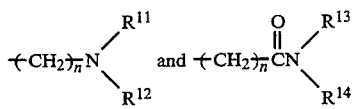

wherein each n is a number independently selected from zero to four, inclusive; wherein each of $R^{11}$ through $R^{14}$ is independently selected from hydrido, alkyl, cycloalkyl, hydroxyalkyl, cycloalkylalkyl, alkoxyalkyl, phenylalkyl and phenyl;

wherein each of $R^9$ and $R^{10}$ is independently selected from hydrido, alkyl, haloalkyl, cycloalkyl, bicycloalkyl, bicycloalkylalkyl, cycloalkylalkyl, phenylalkyl, phenyl, alkenyl and cycloalkenyl; wherein any of said $R^9$ and $R^{10}$ groups may be substituted at one or more substitutable positions by one or more groups selected from alkyl, halo, haloalkyl and alkoxy, with the proviso that when $R^9$ or $R^{10}$ is an alkenyl or a cycloalkenyl group, then the double bond of such group cannot be adjacent to the nitrogen atom or the amido group of Formula I; or a pharmaceutically-acceptable salt thereof.

29. The method of claim 28 wherein m is one or two; wherein $R^1$ is selected from hydrido, alkyl, hydroxyalkyl, halo, haloalkyl, cycloalkyl, alkylcycloalkyl, cycloalkylalkyl, cycloalkylhaloalkyl, alkoxy, benzyl, phenyl, halophenyl, alkoxyalkyl, alkylsilyloxyalkyl, phenyl/alkylsilyloxyalkyl, phenylsilyloxyalkyl and alkylthio;

wherein each of $R^2$, $R^3$ and $R^4$ is independently selected from hydrido, alkyl, hydroxyalkyl, halo, haloalkyl, cycloalkyl, alkylcycloalkyl, cycloalkylalkyl, alkoxy, benzyl, alkoxyalkyl, alkylsilyloxyalkyl and alkylthio;

wherein each of $R^5$, $R^6$, $R^7$ and $R^8$ is independently selected from hydrido, alkyl, hydroxy, hydroxyalkyl, formyl, halo, haloalkyl, cycloalkyl, alkylcycloalkyl, cycloalkylalkyl, alkoxy, alkoxyalkyl, alkylsilyloxyalkyl and alkylthio, with the proviso that at least one of $R^5$, $R^6$, $R^7$ and $R^8$ must be a group other than hydrido;

wherein each of $R^1$, $R^2$, $R^3$, $R^4$, $R^5$, $R^6$, $R^7$ and $R^8$ may be further independently selected from amino radicals of the formula

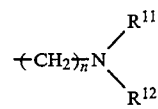

wherein each n is a number independently selected from zero to four, inclusive; wherein each of $R^{11}$ and $R^{12}$ is independently selected from hydrido, alkyl, cycloalkyl, hydroxyalkyl, cycloalkylalkyl, alkoxyalkyl, benzyl and phenyl;

wherein each of $R^9$ and $R^{10}$ is independently selected from hydrido, alkyl, haloalkyl, cycloalkyl, bicycloalkyl, bicycloalkylalkyl, cycloalkylalkyl, phenylalkyl, phenyl, alkenyl and cycloalkenyl; wherein any of said $R^9$ and $R^{10}$ groups may be substituted at one or more substitutable positions by one or more groups selected from alkyl, halo, haloalkyl and alkoxy, with the proviso that when $R^9$ or $R^{10}$ is an alkenyl or a cycloalkenyl group, then the double bond of such group cannot be adjacent to the nitrogen atom or the amido group of Formula I; or a pharmaceutically-acceptable salt thereof.

30. The method of claim 29 wherein m is one; wherein $R^1$ is selected from hydrido, alkyl, hydroxyalkyl, alkoxyalkyl, phenyl, halophenyl, alkylsilyloxyalkyl, amino, monoalkylamino, dialkylamino, aminoalkyl, monoalkylaminoalkyl and dialkylaminoalkyl, wherein when $R^1$ is alkyl or is a group containing alkyl, then such alkyl has one to about six carbon atoms and may have a linear or branched configuration;

wherein each of $R^2$, $R^3$ and $R^4$ is hydrido;

wherein each of $R^5$, $R^6$, $R^7$ and $R^8$ is independently selected from hydrido, hydroxy, alkyl, alkoxy, fluoro, chloro, bromo, haloalkyl, alkylthio, alkoxyalkyl, hydroxyalkyl, alkylthioalkyl, cyano, amino, monoalkylamino, dialkylamino, aminoalkyl, monoalkylaminoalkyl and dialkylaminoalkyl, with the proviso that at least one of $R^5$, $R^6$, $R^7$ and $R^8$ must be a group other than hydrido; wherein when any of the foregoing $R^5$, $R^6$, $R^7$ and $R^8$ is alkyl or is a group containing alkyl, such alkyl has one to about six carbon atoms and may have a linear or branched configuration;

wherein each of $R^9$ and $R^{10}$ is independently selected from hydrido, linear or branched chain alkyl having 1 to about 15 carbon atoms, cycloalkyl having 3 to about 8 carbon atoms, bicycloalkyl having 3 to about 8 carbon atoms in each ring, phenyl, linear or branched alkenyl having 3 to about 15 carbon atoms with the proviso that the double bond of the alkenyl group cannot be adjacent to the nitrogen, cycloalkenyl having 5 to about 8 carbon atoms with the proviso that the double bond cannot be adjacent to the nitrogen of the amido group of Formula I, and wherein any of said $R^9$ and $R^{10}$ substituents may be further substituted with one or more groups selected from linear or branched lower alkyl, loweralkoxy, chloro and bromo; or a pharmaceutically-acceptable salt thereof.

31. The method of claim 30 wherein m is one; wherein $R^1$ is selected from hydrido, methyl, ethyl, n-propyl, isopropyl, n-butyl, isobutyl, sec-butyl, tert-butyl, n-pentyl, isopentyl, neopentyl, hexyl, hydroxymethyl, hydroxyethyl, hydroxypropyl, hydroxybutyl, methoxymethyl, ethoxymethyl, propoxymethyl, butoxymethyl, methoxyethyl, methoxypropyl, methoxybutyl, ethoxyethyl, ethoxypropyl, ethoxybutyl, propoxymethyl, propoxyethyl, propoxypropyl, propoxybutyl, butoxymethyl, butoxyethyl, butoxypropyl, butoxybutyl, phenyl, monofluorophenyl, difluorophenyl, monochlorophenyl, dichlorophenyl, monobromophenyl, dibromophenyl, methylsilyloxymethyl, trimethylsilyloxyethyl, trimethylsilyloxypropyl, trimethylsilyloxybutyl, triethylsilyloxymethyl, triethylsilyloxyethyl, triethylsilyloxypropyl, triethylsilyloxybutyl, tripropylsilyloxymethyl, tripropylsilyloxyethyl, tripropylsilyloxypropyl, tripropylsilyloxybutyl, tert-butyl(dimethyl) silyloxybutyl, amino, N-methylamino, N,N'-dimethylamino, N-ethylamino, N,N'-diethylamino, N-propylamino, N,N'-dipropylamino, N-butylamino, N-N'-dibutylamino, N-methylaminomethyl, N-methylaminoethyl, N-methylaminopropyl, N-methylaminobutyl, N,N'-dimethylaminomethyl, N,N'-dimethylaminoethyl, N,N'-dimethylaminopropyl, N,N'-dimethylaminobutyl, N,N'-diethylaminomethyl, N,N'-diethylaminoethyl, N,N'-diethylaminopropyl, N,N'-diethylaminobutyl, N,N'-dipropylaminomethyl, N,N'-dipropylaminoethyl, N,N'-dipropylaminopropyl, N,N'-dipropylaminobutyl, N,N'-dibutylaminomethyl, N,N'-dibutylaminoethyl, N,N'-dibutylaminopropyl and N,N'-dibutylaminobutyl, wherein when $R^1$ is alkyl group or is one of the foregoing groups containing an alkyl group, such alkyl group may be linear or branched in configuration;

wherein each of $R^2$, $R^3$ and $R^4$ is hydrido;

wherein each of $R^5$, $R^6$, $R^7$ and $R^8$ is independently selected from hydrido, methyl, ethyl, n-propyl, isopropyl, n-butyl, isobutyl, sec-butyl, tert-butyl, n-pentyl, isopentyl, neopentyl, hexyl, fluoro, chloro, bromo, hydroxy, methoxy, ethoxy, propoxy, butoxy, pentoxy, trifluoromethyl, perfluoroethyl, dichloromethyl, methylthio, ethylthio, propylthio, butylthio, pentylthio, hydroxymethyl, hydroxyethyl, hydroxypropyl, hydroxybutyl, methoxymethyl, ethoxymethyl, propoxymethyl, butoxymethyl, methoxyethyl, methoxypropyl, methoxybutyl, ethoxyethyl, ethoxypropyl, ethoxybutyl, propoxymethyl, propoxyethyl, propoxypropyl, propoxybutyl, butoxymethyl, butoxyethyl, butoxypropyl, butoxybutyl, methylthiomethyl, methylthioethyl, methylthiopropyl, methylthiobutyl, ethylthiomethyl, ethylthioethyl, ethylthiopropyl, ethylthiobutyl, propylthiomethyl, propylthioethyl, propylthiopropyl, propylthiobutyl, butylthiomethyl, butylthioethyl, butylthiopropyl, butylthiobutyl, cyano, amino, N-methylamino, N,N'-dimethylamino, N-ethylamino, N,N'-diethylamino, N-propylamino, N,N'-dipropylamino, N-butylamino, N-N'-dibutylamino, N-methylaminomethyl, N-methylaminoethyl, N-methylaminopropyl, N-methylaminobutyl, N,N'-dimethylaminomethyl, N,N'-dimethylaminoethyl, N,N'-dimethylaminopropyl, N,N'-dimethylaminobutyl, N,N'-diethylaminomethyl, N,N'-diethylaminoethyl, N,N'-diethylaminopropyl, N,N'-diethylaminobutyl, N,N'-dipropylaminomethyl, N,N'-dipropylaminoethyl, N,N'-dipropylaminopropyl, N,N'-dipropylaminobutyl, N,N'-dibutylaminomethyl, N,N'-dibutylaminoethyl, N,N'-dibutylaminopropyl and N,N'-dibutylaminobutyl, with the proviso that at least one of $R^5$, $R^6 R^7$ and $R^8$ must be a group other than hydrido; wherein when any of $R^5$, $R^6$, $R^7$ and $R^8$ is alkyl or is a group containing alkyl, such alkyl group may be linear or branched in configuration;

wherein each of $R^9$ and $R^{10}$ independently selected from hydrido, methyl, ethyl, n-propyl, isopropyl, isobutyl, sec-butyl, tert-butyl, n-pentyl, isopentyl, neopentyl, n-hexyl, n-heptyl, n-octyl, n-nonyl, n-decyl, 1,1,3,3-tetramethylbutyl, 2,2-dimethylethyl, 1,1-diethylmethyl, cyclopropyl, cyclobutyl, cyclohexyl, cycloheptyl, cyclooctyl, methylcyclopentyl, ethylcyclopentyl, 2-methylcyclohexyl, 3-methylcyclohexyl, 4-methylcyclohexyl, 3,5-dimethylcyclohexyl, ethylcyclohexyl, 3,5-diethylcyclohexyl, norbornyl, decalin, 2,2,1-bicycloheptyl, 2,2,1-bicycloheptylmethyl and phenyl; or a pharmaceutically-acceptable salt thereof.

32. The method of claim 31 wherein said therapeutically-effective compound is selected from compounds, and their pharmaceutically-acceptable salts, of the group of compounds consisting of N,N-dicyclopentyl-4-(3H-imidazo[4,5-b]pyridin-1-ylmethyl)-3-methoxybenzamide;

N,N-dicyclopentyl-4-(1H-imidazo[4,5-b]pyridin-1-ylmethyl)-3-methoxybenzamide;

N-cyclohexyl-4-(3H-imidazo[4,5-b]pyridin-3-ylmethyl)-2-methoxy-N-(1-methylethyl)benzamide;

N-cyclohexyl-4-(1H-imidazo[4,5-b]pyridin-1-ylmethyl)-2-methoxy-N-(1-methylethyl)benzamide;

N-cyclohexyl-4-(3H-imidazo[4,5-b]pyridin-3-ylmethyl)-3-methoxy-N-(1-methylethyl)benzamide;

N-cyclohexyl-4-(1H-imidazo[4,5-b]pyridin-1-ylmethyl)-3-methoxy-N-(1-methylethyl)benzamide;

N-cyclopentyl-N-(3,5-dimethylcyclohexyl)-4-(3H-imidazo[4,5-b]pyridin-3-ylmethyl)-2-methoxybenzamide;

N-cyclopentyl-N-(3,5-dimethylcyclohexyl)-4-(1H-imidazo[4,5-b]pyridin-1-ylmethyl)-2-methoxybenzamide;

N-cyclohexyl-N-cyclopentyl-4-(1H-imidazo[4,5-b]pyridin-1-ylmethyl)-3-methylbenzamide;

N-cyclohexyl-N-cyclopentyl-4-(3H-imidazo[4,5-b]pyridin-3-ylmethyl)-3-methylbenzamide;

N-cyclohexyl-3-methoxy-N-(1-methylethyl)-4-[(2-methyl-1H-imidazo[4,5-b]pyridin-1-yl)methyl]benzamide;

N-cyclohexyl-3-methoxy-N-(1-methylethyl)-4-[(2-methyl-3H-imidazo[4,5-b]pyridin-3-yl)methyl]benzamide;

N-cyclohexyl-N-cyclopentyl-4-(1H-imidazo[4,5-b]pyridin-1-ylmethyl)-2-methoxybenzamide;

b-[[2-(2-chlorophenyl)-1H-imidazo[4,5-b]pyridin-1-yl]methyl]-N-cyclohexyl-3-methoxy-N-(1-methylethyl)benzamide;

4[[2-(2-chlorophenyl)-1H-imidazo[4,5-b]pyridin-1-yl]methyl]-N-cyclohexyl-3-methoxy-N-(1-methylethyl)benzamide;

4[[2-(2-chlorophenyl)-3H-imidazo[4,5-b]pyridin-3-yl]methyl]-N-cyclohexyl-3-methoxy-N-(1-methylethyl)benzamide;

N-cyclohexyl-4-[[2[[[(1,1-dimethylethyl)dimethylsilyl]oxy]methyl]-1H-imidazo[4,5-b]pyridin-1-yl]methyl]-3-methoxy-N-(1-methylethyl)benzamide;

N-cyclohexyl-4-[[2-(hydroxymethyl)-1H-imidazo[4,5-b]pyridin-1-yl]methyl]-3-methoxy-N-(1-methylethyl)benzamide;

N-cyclohexyl-4-[[2-(hydroxymethyl)-3H-imidazo[4,5-b]pyridin-1-3-yl]methyl]-3-methoxy-N-(1-methylethyl)benzamide;

N-cyclohexyl-4-[[2-[(dimethylamino)methyl]-1H-imidazo[4,5-b]pyridin-1-yl]methyl]-3-methoxy-N-(1-methylethyl)benzamide;

N-cyclohexyl-4-[[2-[(dimethylamino)methyl]-3H-imidazo[4,5-b]pyridin-3-yl]methyl]-3-methoxy-N-(1-methylethyl)benzamide;

N-cyclohexyl-3-methoxy-4-[[2-(methoxymethyl)-1H-imidazo4,5-b]pyridin-1-yl]methyl]-N-(1-methylethyl)benzamide;

N-cyclohexyl-3-methoxy-4-[[2-(methoxymethyl)-3H-imidazo[4,5-b]pyridin-3-yl]methyl]-N-(1-methylethyl)benzamide; and N-cyclohexyl-4-[[2-(dimethylamino)-1H-imidazo[4,5-b]pyridin-1-yl]methyl]-3-methoxy-N-(1-methylethyl)benzamide.

33. The method of claim 32 wherein said compound is N-cyclohexyl-4-(1H-imidazo[4,50b]-pyridin-1-ylmethyl)-2-methoxy-N-(1-methylethyl)benzamide or a pharmaceutically-acceptable salt thereof.

34. The method of claim 32 wherein said compound is N-cyclohexyl-4-[[2-(hydroxymethyl)-1H-imidazo[4,5-b]pyridin-1-yl]methyl]-3-methoxy-N-(1-methylethyl)-benzamide or a pharmaceutically-acceptable salt thereof.

35. The method of claim 32 wherein said compound is N-cyclohexyl-4-[[2-[(dimethylamino)methyl]-1H-imidazo[4,5-b]pyridin-1-yl]methyl]-3-methoxy-N-(1-methylethyl)benzamide or a pharmaceutically-acceptable salt thereof.

36. The method of claim 32 wherein said compound is N-cyclohexyl-3-methoxy-4-[[2-(methoxymethyl)-1H-imidazo4,5-b]pyridin-1-yl]methyl]-N-(1-methylethyl)-benzamide or a pharmaceutically-acceptable salt thereof.

* * * * *